US005783386A

United States Patent [19]
Jacobs, Jr. et al.

[11] Patent Number: 5,783,386
[45] Date of Patent: Jul. 21, 1998

[54] MYCOBACTERIA VIRULENCE FACTORS AND A NOVEL METHOD FOR THEIR IDENTIFICATION

[75] Inventors: William R. Jacobs, Jr., City Island; Barry R. Bloom, Hastings-on-Hudson, both of N.Y.; Desmond Michael Collins; Geoffrey W. de Lisle, both of Wellington, New Zealand; Lisa Pascopella, Hamilton, Mont.; Riku Pamela Kawakami, Wellington, New Zealand

[73] Assignees: Agresearch, New Zealand Pastoral Agriculture Research Institute Ltd., New Zealand; Albert Einstein College of Medicine of Yeshiva University, Bronx, N.Y.

[21] Appl. No.: 363,255

[22] Filed: Dec. 23, 1994

Related U.S. Application Data

[63] Continuation-in-part of Ser. No. 292,695, Aug. 18, 1994, abandoned, which is a continuation-in-part of Ser. No. 265,579, Jun. 24, 1994, abandoned, which is a continuation-in-part of Ser. No. 201,880, Feb. 24, 1994, abandoned.

[51] Int. Cl.[6] .............................. C12Q 1/68; C12P 19/34; C12N 15/00
[52] U.S. Cl. ........................ 435/6; 435/91.2; 435/172.1; 424/248.1
[58] Field of Search .................... 435/6, 91.2, 172.1; 424/248.1

[56] References Cited

PUBLICATIONS

Belisle et al., "Isolation and expression of a gene cluster responsible for biosynthesis of the glycopeptidolipid antigens if *Mycobacterium avium*, " *J. Bacteriol.* (1991) 173:6991–6997.

Boyer et al., "A complementation analysis of the restriction and modification of DNA in *Escherichia coli*," *J. Mol. Biol.* (1969) 41:459–472.

Collins et al., "DNA restriction endonuclease analysis of *Mycobacterium tuberculosis* and *Mycobacterium bovis* BCG," *J. Gen. Microbiol.* (1984) 130:1019–1021.

Collins et al., " *A comparative study of the virulence of Mycobacterium tuberculosis* measured in mice and guinea pigs." *American Review of Respiratory Disease* (1969) 100:631–639.

Collins et al., "DNA fingerprinting of *Mycobacterium bovis* strains by restriction fragment analysis and hybridization with insertion elements IS1081 and IS6110." *J. Clin. Microbiol.* (1993) 31:1143–1147.

Dannenberg, A.M., Jr., "Delayed–type hypersensitivity and cell–mediated immunity in the pathogenesis of tuberculosis." *Immunity Today* (1991) 12:228–233.

Gallagher et al., "A selective oleic acid albumin agar medium for the cultivation of *Mycobacterium bovis*," (1977) *j. Hvq. Camb.* 79:155–160.

Grange et al., "What is BCG?" *Tubercle* (1983) 64:129–139.

Grosskinsky et al., "Genetic relationships among *Mycrobacterium leprae*, *Mycobacterium tuberculosis*, and candidate leprosy vaccine strains determined by DNA hybridization: Identification of an *M. leprae*–specific repetitive sequence." *Infect. Immun.* (1989) 57:1535–1541.

Jacobs et al., "In vivo repackaging of recombinant cosmid molecules for analyses of *Salmonella typhimurium*, *Streptococcus mutans*, and mycobacterial genomic libraries." *Infect. Immun.* (1986) 52:101–109.

Jacobs et al., "Genetic systems for mycobacteria." *Meth. Enzymol.* (1991) 204:537–555.

Jacobs et al., "Introduction of foreign DNA into mycobacteria using a shuttle plasmid." *Nature* (1987) 327:523–535.

Kalpana et al., "Insertional mutagenesis and illegitimate recombination in mycobacteria." *Proc. Natl. Acad. Sci. USA*, (1991) 88:5433–5437.

Kochi, A., "The global tuberculosis situation and the new control strategy of the World Heath Organization." *Tubercle*(1991) 72:1–6.

Lee et al., "Site–specific integration of mycobacteriophage L5: Integration–proficient vectors for *Mycobacterium smegmatis*, *Mycobacterium tuberculosis*, and bacille CalmetteGuérin." *Proc. Natl. Acad. Sci. U.S.A.* (1991) 88:3111–3115.

Mackaness et al., "The growth of intracellular tubercle bacilli in relation to their virulence." *Am. Rev. Tuberc.* (1954) 69:479–494.

North et al., "Mycobacterial virulence. Virulent strains of *Mycobacteria tuberculosis* have faster in vivo doubling times and are better equipped to resist growth–inhibiting functions of macrophages in the presence and absence of specific immunity." *J. Exp. Med.* (1993) 177:1723–1733.

Oatway et al., "The pathogenesis and fate of tubercle produced by dissociated variants of tubercle bacilli." *J. Inf. Dis.* (1936) 59:306–325.

Pascopella et al., "Use of in vivo complementation in *Mycobacterium tuberculosis* to identify a genomic fragment associated with virulence." *Infection and Immunity* (1994) 62:1313–1319.

Pierce et al., "Multiplication and survival of tubercle bacilli in the organs of mice." *J. Exp. Med.* (1953) 97:189206.

(List continued on next page.)

*Primary Examiner*—James C. Housel
*Assistant Examiner*—Rodney P. Swartz
*Attorney, Agent, or Firm*—Morrison & Foerster LLP

[57] ABSTRACT

Polynucleotides associated with virulence in mycobacteria, and particularly a fragment of DNA isolated from *M. bovis* that contains a region encoding a putative sigma factor. Also provided are methods for a DNA sequence or sequences associated with virulence determinants in mycobacteria, and particularly in *M. tuberculosis* and *M. bovis*. The invention also provides corresponding polynucleotides associated with avirulence in mycobacteria. In addition, the invention provides a method for producing strains with altered virulence or other properties which can themselves be used to identify and manipulate individual genes.

3 Claims, 32 Drawing Sheets

OTHER PUBLICATIONS

Steenken et al., "History of H37 strains of tubercle bacillus." *Amer. Rev. Tuberc.* (1946) 54:62–66.

Steenken et al., "Biological studies of the tubercle bacillus. III. Dissociation and pathogenicity of the R and S variants of the human tubercle bacillus ($H_{37}$)." *J. Exp. Med.* (1934) 60:515–540, Plates 31–33.

Stover et al., "New use of BCG for recombinant vaccines," *Nature* (1991) 351:456–460.

van Soolingen et al., "Occurrence and stability of insertion sequences in *Mycobacterium tuberculosis* complex strains: evaluation of an insertion sequence-dependent DNA polymorphism as a tool in the epidemiology of tuberculosis," *J. Clin. Microbiol.* (1991) 29:2578–2S86.

Young et al., "Leprosy, tuberculosis, and the new genetics," *J. Bacteriol.* (1993) 175:1–6.

Bloch et al., "Viability and multiplication of vaccines in immunization against tuberculosis" *Am. Rev. Tuberc. Pulm. Dis.* (1954) 71:228–248.

Fang et al., "The alternative σ factor KatF (RpoS) regulates Salmonella virulence" *Proc. Natl. Acad. Sci. USA* (1992) 89:11978–11982.

Deretic et al., "Conversion of *Pseudomonas aeruginosa* to mucoidy in cystic fibrosis: environmental stress and regulation of bacterial virulence by alternative sigma factors" *J. Bacteriol.* (1994) 176:2773–2780.

Buttner et al., "Cloning, disruption, and transcriptional analysis of three RNA polymerase sigma factor genes of streptomyces coelicolor A3(2)" *J. Bacteriol.* (1990) 173:3367–3378.

Predich et al., "Characterization of RNA polymerase and two sigma–factor genes from *Mycobacterium smegmatis*, " *Mol. Microbiol.* (1995) 15:355–366.

Rosner, J.L., "Susceptibilities of oxyR regulon mutants of *Escherichia coli* and *Salmonella typhimurium* to isoniazid," *Antimicrobial Agents and Chemotherapy* (1993) 37:2251–2253.

Pascopella et al., "Identification of a genomic fragment of Mycobacterium tuberculosis responsible for in vivo advantage," *Infectious Agents and Disease* (1993) 2:282–284.

Gardella et al., "A mutant Escherichia coli sigma70 subunit of RNA polymerase with altered promoter specificity," *Journal of Mol. Biology* (1989) 206:579–590.

Jacobs et al., "Molecular genetic stratgies for identifying virulence determinants of Mycobacterium tuberculosis," *Tuberculosis: Pathogenesis, protection, and control*, Bloom, B.R., ed., (1994) pp. 253–268.

Skamene, Emil "Genetic Control of Suspectibility to Mycobacterial Infections" Rev. Inf. Dis. (11): 5394–399.

Smith et al, "What Animals Models can Teach us about the Pathogenesis of TB in Humans" Rev. Inf. Dis. vol. 11:385–393.

```
  1  GATCAAGCTG CTGACCCCGC AACCGGCCAC TCCGTTGGCG GTCGCCAAAA
 51  CCATCGCCGA GGTCGTCAAC GGTTTCGGCT GGCGGGGTCC GCTGGGGGTG
101  ACCTATCCCG GCGTCGTCAC TCACGGCGTC GTCCGGACCG CGGCTAACGT
151  GGACAAGTCC TGGATAGGGA CCAACGCACG CGACACTATC GGCGCCGAGC
201  TGGGCGGTCA GCAGGTCACC ATCCTCAACG ACGCTGATGC CGCCGGGCTG
251  GCCGAGACAC GCTACGGGGC CGGCAAGAAC AACCCTGGCT TAGTGGTACT
301  GCTCACATTC GGAACCGGGA TCGGGTCCGC GGTCATCCAC AACGGGACGT
351  TGATACCCAA CACCGAGTTC GGACATCTTG AGGTCGGGCGG CAAGGAAGCG
401  GAGGAAAGGG CCGCCTCCTC GGTAAAGGAA AAGAACGACT GGACCTATCC
451  AAAGTGGGCC AAGCAGGTGA CACGCGTGCT CATCGCCATC GAGAACGCGA
501  TCTGGCCTGA CCTGTTCATC GCCGCGGGCG GCATCAGCCG CAAGGCCGAC
551  AAATGGGTGC CGCTACTGGA AAACCGCACA CCAGTAGTGC CCGGGCCCT
601  GCAGAACACC GCCGGAATTG TCGGTGCGGC CATGGCCTCT GTCGCAGATA
651  CGACGCACTG AAACTTGCCC GCTCGGGCTG TACTCGTGCG CAGTAAAGTT
701  ACAATGGTCA GCGGCGGGCG CCCGACCGAT AGCGGCGCGAG TATTCACGCT
751  GATATCAACG CCGACATTCG ACATAGCAGA CACTTTCGGT TACGCACGCC
801  CAGACCCAAC CGGAAGTGAG TAACGACCGA AGGGGTGTAT GTGGCAGGGA
851  CCAAAGCAAG CACGGGGACC GATGAGCCGG TAAAACGCAC CGCCACCAAG
901  TCGCCCGCGG CTTCCGCGTC CGGGGCCAAG ACCGGCCCCA AGCGAACAGC
```

FIGURE 9 - 1

```
 951  GGGGAAGTCC GCTAGTGGCT CCCCACCCGC GAAGCGGGCT ACCAAGCCCG
1001  CGGCCCGGTC CGTCAAGCCC GCCTCGGCAC CCCAGGACAC TACGACCAGC
1051  ACCATCCCGA AAAGGAAGAC CCGCGCCGCG GCCAAATCCG CCGCCGCGAA
1101  GGCACCGTCG GCCCGCGGCC ACGCGACCAA GCCACGGGCG CCCAAGGATG
1151  CCCAGCACGA AGCGCAACG GATCCCGAGG ACGCCCTGGA CTCCGTCGAG
1201  GAGCTCGACG CTGAACCAGA CCTCGACGTC GAGCCCGGCG AGGACCTCGA
1251  CCTTGACGCC GCCGACCTCA ACCTCGATGA CCTCGAGGAC GACGTGGCGC
1301  CGGACGCCGA CGACGACCTC GACTCGGGCG ACGACGAAGA CCACGAAGAC
1351  CTCGAAGCTG AGGCGGCCGT CGCGCCCGGC CAGACCGCCG ATGACGACGA
1401  GGAGATCGCT GAACCCACCG AAAAGGACAA GGCCTCCGGT GATTTCGTCT
1451  GGGATGAAGA CGAGTCGGAG GCCCTGCGTC AAGCACGCAA GGACGCCGAA
1501  CTCACCGCAT CCGCCGACTC GGTTCGCGCC TACCTCAAAC AGATCGGCAA
1551  GGTAGCGCTG CTCAACGCCG AGGAAGAGGT CGAGCTAGCC AAGCGGGATCG
1601  AGGCTGGCCT GTACGCCACG CAGCTGATGA CCGAGCTTAG CGAGGCGGGC
1651  GAAAAGCTGC CTGCCGCCCA GCGCCGGGAC ATGATGTGGA TCTGCCGCGA
1701  CGGCGATCGC GCGAAAAACC ATCTGCTGGA AGCCAACCTG CGCCTGGTGG
1751  TTTCGCTAGC CAAGCGCTAC ACCGGCCGGG GCATGGCGTT TCTCGACCTG
1801  ATCCAGGAAG GCAACCTGGG GCTGATCCGC GCGGTGGAGA AGTTCGACTA
1851  CACCAAGGGG TACAAGTTCT CCACCTACGC TACGTGGTGG ATTCGCCAGG
```

FIGURE 9 - 2

```
1901  CCATCACCCG CGCCATGGCC GACCAGGCCC GCACCATCCG CATCCCGGTG
1951  CACATGGTCG AGGTGATCAA CAAGCTGGGC CGCATTCAAC GCGAGCTGCT
2001  GCAGGACCTG GGCCGCGAGC CCACGCCCGA GGAGCTGGCC AAAGAGATGG
2051  ACATCACCCC GGAGAAGGTG CTGGAAATCC AGCAATACGC CCGCGAGCCG
2101  ATCTCGTTGG ACCAGACCAT CGGCGACGAG GGCGACAGCC AGCTTGGCGA
2151  TTTCATCGAA GACAGGAGG  CGGTGGTGGC CGTCGACGCG GTGTCCTTCA
2201  CTTTGCTGCA GGATCAACTG CAGTCGGTGC TGGACACGCT CTCCGAGCGT
2251  GAGGCGGGCG TGGTGCGGCT ACGCTTCGGC CTTACCGACG GCCAGCCGCG
2301  CACCCTTGAC GAGATCGGCC AGGTCTACGG CGTGACCCGG GAACGCATCC
2351  GCCAGATCGA ATCCAAGACT ATGTCGAAGT TGCGCCATCC GAGCCGCTCA
2401  CAGGTCCTGC GCGACTACCT GGACTGAGAG CGCCCGCCGA GGCGACCAAC
2451  GTAGCGGGCC CCCATGTCAG CTAGCCGCAC CATGGTCTCG TCCGGATCGG
2501  AGTTCGAATC AGCCGTCGGC TACTCGCGCG CGGTACGCAT CGGGCCACTC
2551  GTGGTGGTGG CCGGAACGAC CGGCAGCGGC GATGATATCG TCGCTCAGAC
2601  GCGAGACGCT CTGCGCCGCA TCGAGATTGC GCTCGGACAG GCCGGGCAA
2651  CTCTGGCCGA CGTGGTCCGT ACCCGCATCT ATGTGACCGA TATTTCCCGC
2701  TGGGCGAGG  TCGGCGAAGT GCATGCACAG GCTTTCGGCA AGATC
```

FIGURE 9 - 3

```
  1  GATCAAGCTGCTGACCCCGCAACGGCCACTCCGTTGGCGGTCGCCAAAACCATCGCCGA    60
 61  GGTCGTCAACGGTTTCGGCTGGGCGGGTCCGCTGGGGTGACCTATCCCGGCGTCGTCAC   120
121  TCACGGCGTCGTCCGGACGCGGCTAAGCGTGGACAAGTCCTGGATAGGGACCAACGCACG   180
181  CGACACTATCGGCGCCGAGCTGGGGCGGTCAGCAGGTCACCATCCTCAAGCGACGCTGATGC   240
241  CGCCGGGCTGGCCGAGACACGCTGGGATCGGGGCCGGCAAGAACAACCCTGGCTTAGTGGTACT   300
301  GCTCACATTCGGAACCGGGATCGGGTCCGCGGTCATCCACAACGGGACGTTGATACCCAA   360
361  CACCGAGTTCGGACATCTTGAGGTCGGCGGACCTATCCAAAGTGGGCAAGGAAGGCCGCCTCTC   420
421  GGTAAAGGAAAAAGAACTGAGAACGCGATCTGCCTGACCTGTTCATCGCCGGCATCAGCCG   480
481  CATCGCCATCGAGAACGCGATCTGCCTACTGGAAAACCGCACACCAGTAGTGCCCGGGCCCT   540
541  CAAGGCCGACAAATGGGTGCCGCTACTGCGTGCCCTCTGTGCCAGATACGACGCACTG   600
601  GCAGAACACCGCCGGAATTGTCGCGAGTATTCACGCTGATATCAACCGAAGTTACAATGGTCAGGGGCCG   660
661  AAACTTGCCCGCTCGGGCTGTACTCGTGCGCAGTAAAGTTACAATGGTCAGGGGCCG   720
721  CCCGACCGATAGCGCGGCGAGTATTCACGCTGATATCAACCGACATTCGACATAGCAGA   780
781  CACTTTCGGTTACGCCACGCCCAGACCCAACCGGAGTGAGTAACGACCGAAGGGGTGTAT   840
                                                              V  Y
841  GTGGCAGGAGGACCAAAGCAAGCACGGACCGATGAGCGGGTAAAACGCACCGCCACCAAG   900
     V  A  A  T  K  A  S  T  A  T  D  E  P  V  K  R  T  A  T  K
901  TCGCCCGCGGCTTCCGGCGTCCGGGGCCAAGACCGGCCCCAAGCGGAACAGCGGCGAAGTCC   960
     S  P  A  A  S  A  S  G  A  K  T  G  P  K  R  T  A  A  K  S
```

FIGURE 9A - 1

```
 961  GCTAGTGGCTCCCCACCCGGGAAGGGGCTACCAAGCCCGGCCCGGTCCGTCAAGCCC 1020
       A  S  G  S  P  P  A  K  R  A  T  K  P  A  A  R  S  V  K  P
1021  GCCTCGGCACCCCAGGACACTACGACACCATCCGAAAAGGAAGACCCGGCCGGCG 1080
       A  S  A  P  Q  D  T  T  T  S  T  I  P  K  R  K  T  R  A  A
1081  GCCAAATCCGCCGCGGAAGCACCGGTCGGCCCGCCCAAGCCACGGGCG 1140
       A  K  S  A  A  K  A  P  S  A  R  G  H  A  T  K  P  R  A
1141  CCCAAGGATGCCCAGCACGAAGCCGACAACGGATCCCGAGGACGCCCTGGACTCCGTCGAG 1200
       P  K  D  A  Q  H  E  A  A  T  D  P  E  D  A  L  D  S  V  E
1201  GAGCTCGACGCTGAACCAGACCTCGACGTCGAGCCCGGCGAGGAGGACCTCGACCTTGACGCC 1260
       E  L  D  A  E  P  D  L  D  V  E  P  G  E  D  L  D  L  D  A
1261  GCCGACCTCAACCTCGATGACCTCGAGGACGACGAAGACCTCGAAGCTCGAGGGCCGTCGGCCCCGGC 1320
       A  D  L  N  L  D  D  L  E  D  D  V  A  P  D  A  D  D  D  L
1321  GACTCGGGGCGACGAAGACGAGGAGATCGCTGAACCCACCGAAAAGGACAAGGCCTCCGGT 1380
       D  S  G  D  D  E  D  H  E  D  L  E  A  E  A  A  V  A  P  G
1381  CAGACCGCCGATGACGAAGACGAGGAGATCGCTGAACCCACCGAAAAGGACAAGGCCTCCGGT 1440
       Q  T  A  D  D  E  E  I  A  E  P  T  E  K  D  K  A  S  G
1441  GATTTCGTCTGGGATGAAGACGAGTCGGAGGCCCTGCGTCAAGCACGAGCAGAAGGCCGAA 1500
       D  F  V  W  D  E  D  E  S  E  A  L  R  Q  A  R  K  D  A  E
1501  CTCACCGCCATCGCCGACTCGGTTCGGCGCTACCTCAAACAGATCGGGAAGGTAGGCGCTG 1560
       L  T  A  S  A  D  S  V  R  A  Y  L  K  Q  I  G  K  V  A  L
```

FIGURE 9A - 2

```
1561  CTCAACGCCGAGGAAGAGGTCGAGCTAGCCAAGCGGATCGAGGCTGGCCTGTACGCCACG  1620
       L  N  A  E  E  E  V  E  L  A  K  R  I  E  A  G  L  Y  A  T

1621  CAGCTGATGACCGAGCTTAGCGAGCGGGCGGAGAAAGCTGCTGCCCAGCGCCGCGAC     1680
       Q  L  M  T  E  L  S  E  R  G  E  K  L  P  A  A  Q  R  R  D

1681  ATGATGTGGATCTGCCGCGACGGCGATCGCGCGAAAAACCATCTGCTGGAAGCCAACCTG  1740
       M  M  W  I  C  R  D  G  D  R  A  K  N  H  L  L  E  A  N  L

1741  CGGCTGGTGGTTTCGCTAGCCAAGCGCTACACCGGCGGGCATGGCGTTTCTGACCTG     1800
       R  L  V  V  S  L  A  K  R  Y  T  G  R  G  M  A  F  L  D  L

1801  ATCCAGGAAGGCAACCTGGGGCTGATCCGCGCGGTGGAGAAGTTCGACTACACCAAGGGG  1860
       I  Q  E  G  N  L  G  L  I  R  A  V  E  K  F  D  Y  T  K  G

1861  TACAAGTTCTCCACCTACGCTACGTGGTGGATTCGCCAGGCCATCACCCGGCCATGGCC  1920
       Y  K  F  S  T  Y  A  T  W  W  I  R  Q  A  I  T  R  A  M  A

1921  GACCAGGCCCGCACCATCCGGATTCCCGGTGCACATGGTTCGAGGTGATCAACAAGCTGGGC  1980
       D  Q  A  R  T  I  R  I  P  V  H  M  V  E  V  I  N  K  L  G

1981  CGGCATTCAACGGAGACATCACCCCCGGAGAACCTGGGCCGGGAGACCCCGGAGGAGCTGGCC  2840
       R  I  Q  R  E  L  L  Q  D  L  G  R  E  P  T  P  E  E  L  A

2041  AAAGAGATGGACATCACCCCGGAGAAGGTGCTGGAAATCCAGCAATACGCCCGGAGCCG   2100
       K  E  M  D  I  T  P  E  K  V  L  E  I  Q  Q  Y  A  R  E  P

2101  ATCTCGTTGGACCAGACCATCGGGGACGAGGGGCGACAGCCAGCTTGGCGATTTCATCGAA  2160
       I  S  L  D  Q  T  I  G  D  E  G  D  S  Q  L  G  D  F  I  E
```

FIGURE 9A - 3

```
2161  GACAGGCGAGGCGGTGGTGGCCGTCGACGCGGTGTCCTTCACTTTGCTGCAGGATCAACTG  2220
       D  S  E  A  V  V  A  V  D  A  V  S  F  T  L  L  Q  D  Q  L
2221  CAGTCGGTGCTGGACACGCTCTCCGAGCGTGAGGCGGGGCGTGGTGCGCTACGCTTCGGC  2280
       Q  S  V  L  D  T  L  S  E  R  E  A  G  V  V  R  L  R  F  G
2281  CTTACCGACGGCCAGGCCCGGCACCCTTGACGAGATCGGGCCAGGTCTACGGGTGACCCGG  2340
       L  T  D  G  Q  P  R  T  L  D  E  I  G  Q  V  Y  G  V  T  R
2341  GAACGCATCCGCCAGATCGAATCCAAGACTATGTCGAAGTTGCGCCATCCGAGCCGCTCA  2400
       E  R  I  R  Q  I  E  S  K  T  M  S  K  L  R  H  P  S  R  S
2401  CAGGTCCTGCGCGACTACCTGGACTGAGAGGCCCGCCGAGGCGACCAACGTAGCGGGCC  2460
       Q  V  L  R  D  Y  L  D  *
2461  CCCATGTCAGCTAGCCGCCACCATGGTCTCGTCCGGATCGGAGTTCGAATCAGCCGTCGGC  2520
2521  TACTCGCGCGGGTACGCATCGGGCCACTCGTGGTGGCCGGAACGACCGGAGCGGC  2580
2581  GATGATATCGTCGCTCAGACGCGGAGAGCTCTGCGCCATCGAGATTGCGCTCGGACACAG  2640
2641  GCCGGGCAACTCTGGCCGACGTGGTCCGTACCCGCATCTATGTGACCGATATTTCCCGC  2700
2701  TGGCGCGAGGTCGGGGAAGTGCATGCACAGGCTTTCGGCAAGATC              2745
```

FIGURE 9A - 4

```
                    1                                                   50
M.bovis rpoV        VYVAA..... TKASTATDEP VKRTATKSPA ASASGAKTGP KRTAAKSASG
S.coelicolor hrdB   MVSAAE.PKR TRKSVAAKSP AKRTATKAVA ANPVTSRKA. .......TAP
S.griseus hrdB      MVSAAESPKR ARKSVAAKSP VKRTATKTVA AKTTVTRTV. .......AAT 51                                                 100
M.bovis rpoV        SPPAKRATKP AARSVKPASA PQDTTTSTIP KRKTRAAAKS AAAKAPSARG
S.coelicolor hrdB   AAPAAPATEP AAVE.EEAPA K......... ........KA AAKKTTAKKA
S.griseus hrdB      AAPAVESADA ADDAVAAAPA K......... ........KT AAKKATAKKA 101                                                150
M.bovis rpoV        HATKPRAPKD AQHEAATDPE DALDSVEELD AEPDLDVEPG EDLDLDAADL
S.coelicolor hrdB   TAKKTTAKKA AAKKTTAKKE DGELLEDEAT EEPKA..ATE EPEGTENAGF
S.griseus hrdB      AAKKTTAKKT AAKK.SGKQD DEILDGDEAA EEVKAGKGEE EEGEGENKGF 151                                                200
M.bovis rpoV        NLDDLEDDVA PDADDDLDSG DDEDHEDLEA EAAVAPGQTA DDDEEIAEPT
S.coelicolor hrdB   VLSDEDEDDA P......... .......... .......... ..........
S.griseus hrdB      VLSDDDEDDA P......... .......... .......... ..........
```

FIGURE 10A - 1

```
                   201                                                250
M.bovis rpoV       EKDKASGDFV WDEDESEALR QARKDAELTA SADSVRAYLK QIGKVALLNA
S.coelicolor hrdB  .......... .......... .AQQVAAAGA TADPVKDYLK QIGKVPLLNA
S.griseus hrdB     .......... .......... .AQQVAVAGA TADPVKDYLK QIGKVPLLNA 251                                                300
M.bovis rpoV       EEEVELAKRI EAGLYATQLM TELSERGEKL PAAQRRDMMW ICRDGDRAKN
S.coelicolor hrdB  EQEVELAKRI EAGLFAEDKL AN....SDKL APKLKRELEI IAEDGRRAKN
S.griseus hrdB     EQEVELAKRI EAGLFAEDKL AN....ADKL APKLKRELEI IAEDGRRAKN 301                                                350
M.bovis rpoV       HLLEANLRLV VSLAKRYTGR GMAFLDLIQE GNLGLIRAVE KFDYTKGYKF
S.coelicolor hrdB  HLLEANLRLV VSLAKRYTGR GMLFLDLIQE GNLGLIRAVE KFDYTKGYKF
S.griseus hrdB     HLLEANLRLV VSLAKRYTGR GMLFLDLIQE GNLGLIRAVE KFDYTKGYKF 351                                                400
M.bovis rpoV       STYATWWIRQ AITRAMADQA RTIRIPVHMV EVINKLGRIQ RELLQDLGRE
S.coelicolor hrdB  STYATWWIRQ AITRAMADQA RTIRIPVHMV EVINKLARVQ RQMLQDLGRE
S.griseus hrdB     STYATWWIRQ AITRAMADQA RTIRIPVHMV EVINKLARVQ RQMLQDLGRE
```

FIGURE 10A - 2

```
                      401                                                    450
M.bovis rpoV          PTPEELAKEM DITPEKVLEI QQYAREPISL DQTIGDEGDS QLGDFIEDSE
S.coelicolor hrdB     PTPEELAKEL DMTPEKVIEV QKYGREPISL HTPLGEDGDS EFGDLIEDSE
S.griseus hrdB        PTPEELAKEL DMTPEKVIEV QKYGREPISL HTPLGEDGDS EFGDLIEDSE 451                                                    500
M.bovis rpoV          AVVAVDAVSF TLLQDQLQSV LDTLSEREAG VVRLRFGLTD GQPRTLDEIG
S.coelicolor hrdB     AVVPADAVSF TLLQEQLHSV LDTLSEREAG VVSMRFGLTD GQPKTLDEIG
S.griseus hrdB        AVVPADAVSF TLLQEQLHSV LDTLSEREAG VVSMRFGLTD GQPKTLDEIG 501                                 536
M.bovis rpoV          QVYGVTRERI RQIESKTMSK LRHPSRSQVL RDYLD*
S.coelicolor hrdB     KVYGVTRERI RQIESKTMSK LRHPSRSQVL RDYLD*
S.griseus hrdB        KVYGVTRERI RQIESKTMSK LRHPSRSQVL RDYLD*
```

FIGURE 10A - 3

```
Gap Weight:    3.000        Average Match:     0.540
Length Weight: 0.100        Average Mismatch: -0.396

Quality: 262.3              Length:  536
         Ratio: 0.699                Gaps:    8
Percent Similarity: 72.632   Percent Identity: 59.649

108071.pep x cont.pepf     May 30, 1994  12:52  ..

1 MVSAAESPKRARKSVAAKSPVKRTATKTVA.....AKTTVTRTVA..... 40
     : ||. : |.|...||||||||.|   |||...||.|
  1 VYVAATXA.....STATDEPVKRTATKSPAASASGAKTGPKRTAAKSASG 45

41 ........ATAAPAVESADAADDAVAAAPAK...KTAAKKATAKKAAAKK 79
            ||.|..|.|:|:|.......:|  :..|||.|.|| :.|:
 46 SPPAKRATKPAARSVKPASAPQDTTTSTIPKRKTRAAAKSAAAKAPSARG 95

80 TTAKKTAAKK................................... 89
    ..|. |:|.
 96 HATKPRAPKDAQHEAATDPEDALDSVEELDAEPDLDFEPGEDLDLDAADL 145

90 .................SGKQDDEILDGDEAAEEVKAGKGEEEEGEGE 120
                     ::.:|.| |:::.|     |..::||.:|.
146 NLDDLEDDVAPDADDDLDSGDDEDHEDLEAEAAVAPGQTADDDEEIAEPT 195

121 NK....GFVLSDDDEDDA..PAQQVAVAGATADPVKDYLKQIGKVPLLNA 164
    :|    |.|:.||.:.|    .|   |.|||.|:.|||||||||:|||
196 EKDKASGDFVWDEDESEALRQARKDAELTASADSVRAYLKQIGKVALLNA 245

165 EQEVELAKRIEAGLFAEDKLAN....ADKLAPKLKRELEIIAEDGRRAKN 210
    |:||||||||||||:|   ...    ::||:: :|:: |. || ||||
246 EEEVELAKRIEAGLYATQLMTELSERGEKLPAAQRRDMMWICRDGDRAKN 295

211 HLLEANLRLVVSLAKRYTGRGMLFLDLIQEGNLGLIRAVEKFDYTKGYKF 260
    |||||||||||||||||||||| ||||||||||||||||||||||||||
296 HLLEANLRLVVSLAKRYTGRGMAFLDLIQEGNLGLIRAVEKFDYTKGYKF 345

261 STYATWWIRQAITRAMADQARTIRIPVHMVEVINKLARVQRQMLQDLGRE 310
    |||||||||||||||||||||||||||||
346 STYATWWIRQAITRAMADQARTIRIPVHMV..................... 375
```

FIGURE 11

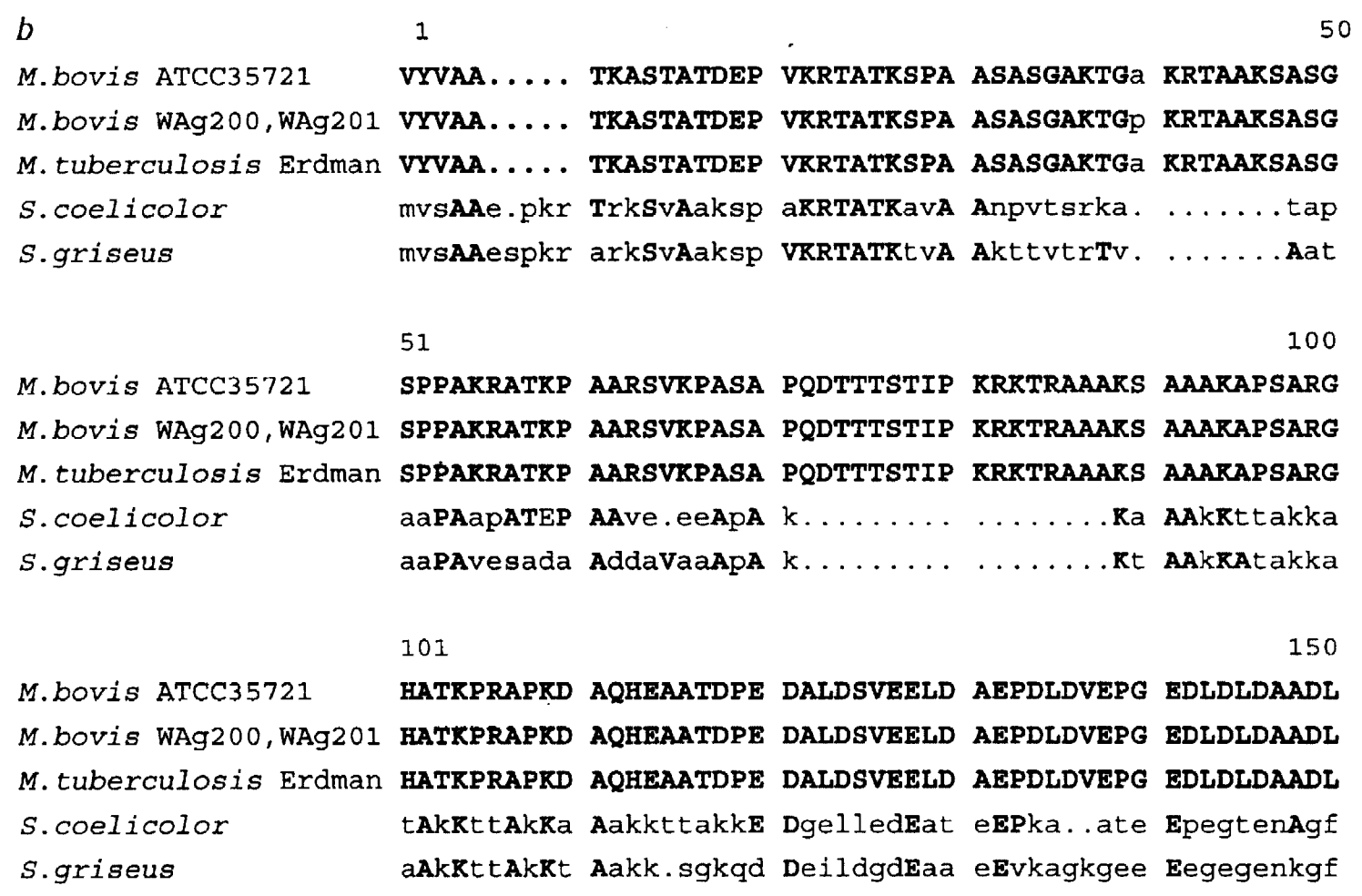

```
                    1
M.bovis ATCC35721    VYVAA.....  TKAS

```
                              151                                                        200
M.bovis ATCC35721             NLDDLEDDVA PDADDDLDSG DDEDHEDLEA EAAV

```
                       301                                                           350
M.bovis ATCC35721      HLLEANLRLV VSLAKRYTGR GMAFLDLIQE GNLGLIRAVE KFDYTKGYKF
M.bovis WAg200,WAg201  HLLEANLRLV VSLAKRYTGR GMAFLDLIQE GNLGLIRAVE KFDYTKGYKF
M.tuberculosis Erdman  HLLEANLRLV VSLAKRYTGR GMAFLDLIQE GNLGLIRAVE KFDYTKGYKF
S.coelicolor           HLLEANLRLV VSLAKRYTGR GMiFLDLIQE GNLGLIRAVE KFDYTKGYKF
S.griseus              HLLEANLRLV VSLAKRYTGR GMiFLDLIQE GNLGLIRAVE KFDYTKGYKF 351                                                           400
M.bovis ATCC35721      STYATWWIRQ AITRAMADQA RTIRIPVHMV EVINKLGRIQ RELLQDLGRE
M.bovis WAg200,WAg201  STYATWWIRQ AITRAMADQA RTIRIPVHMV EVINKLGRIQ RELLQDLGRE
M.tuberculosis Erdman  STYATWWIRQ AITRAMADQA RTIRIPVHMV EVINKLGRIQ RELLQDLGRE
S.coelicolor           STYATWWIRQ AITRAMADQA RTIRIPVHMV EVINKLaRvQ RqmLQDLGRE
S.griseus              STYATWWIRQ AITRAMADQA RTIRIPVHMV EVINKLaRvQ RqmLQDLGRE 401                                                           450
M.bovis ATCC35721      PTPEELAKEM DITPEKVLEI QQYAREPISL DQTIGDEGDS QLGDFIEDSE
M.bovis WAg200,WAg201  PTPEELAKEM DITPEKVLEI QQYAREPISL DQTIGDEGDS QLGDFIEDSE
M.tuberculosis Erdman  PTPEELAKEM DITPEKVLEI QQYAREPISL DQTIGDEGDS QLGDFIEDSE
S.coelicolor           PTPEELAKEl DmTPEKViEv QkYgREPISL htplGedGDS efGDIIEDSE
S.griseus              PTPEELAKEl DmTPEKViEv QkYgREPISL htplGedGDS efGDIIEDSE
```

FIGURE 12 - 3

| | 451 | | | | 500 |
|---|---|---|---|---|---|
| *M.bovis* ATCC35721 | AVVAVDAVSF | TLLQDQLQSV | LDTLSEREAG | VVRLRFGLTD | GQPRTLDEIG |
| *M.bovis* WAg200,WAg201 | AVVAVDAVSF | TLLQDQLQSV | LDTLSEREAG | VVRLRFGLTD | GQPRTLDEIG |
| *M.tuberculosis* Erdman | AVVAVDAVSF | TLLQDQLQSV | LDTLSEREAG | VVRLRFGLTD | GQPRTLDEIG |
| *S.coelicolor* | AVVpaDAVSF | TLLQeQLhSV | LDTLSEREAG | VVsmRFGLTD | GQPkTLDEIG |
| *S.griseus* | AVVpaDAVSF | TLLQeQLhSV | LDTLSEREAG | VVsmRFGLTD | GQPkTLDEIG |

| | 501 | | ↓ | 536 |
|---|---|---|---|---|
| *M.bovis* ATCC35721 | QVYGVTRERI | RQIESKTMSK | LhHPSRSQVL | RDYLD* |
| *M.bovis* WAg200,WAg201 | QVYGVTRERI | RQIESKTMSK | LRHPSRSQVL | RDYLD* |
| *M.tuberculosis* Erdman | QVYGVTRERI | RQIESKTMSK | LRHPSRSQVL | RDYLD* |
| *S.coelicolor* | kVYGVTRERI | RQIESKTMSK | LRHPSRSQVL | RDYLD* |
| *S.griseus* | kVYGVTRERI | RQIESKTMSK | LRHPSRSQVL | RDYLD* |

FIGURE 12 - 4

```
GATCAAGCTGCTGACCCCGCAACCGGCCACTCCGTTGGGCGGTCGCCAAAACCATCGCCGA    60
GGTCGTCAACGGTTTCGGCTGGCGGGTTCCGCTGGGGGTTGACCTATCCCGGCGTCGTCAC   120
TCACGGGCGTCGTCCGGACCGCGGCTAACGTGGACAAGTCCTGGATAGGACCAACGCACG    180
CGACACTATCGGGCGCCGAGCTGGGCGGTCAGCAGGTCACCATCCTCAACGACGCTGATGC   240
CGCCGGGCTGGCCGAGACACGCTACGGGCCGGCAAGAACAACCCTGGCTTAGTGGTACT     300
GCTCACATTCGGAACCGGGATCGGGTCCGCGGTCATCCACAACGGGACGTTGATACCCAA    360
CACCGAGTTCGGACATCTTGAGGTCGGACCTATCCAAAGTGGCCAAGCAGGTGACACGCTGCT 420
GGTAAAGGAAAAGAACGACTGGACCTATCCAAAGTGGCCAAGCAGGTGACACGCGTGCT     480
CATCGCCATCGAGAACGCGATCTGCCTGACCTGTTCATCGCCGGCGGCATCAGCCG        540
CAAGGCCGACAAATGGGTGCCGCTACTGGAAAACCGCACACCAGTGCCGGGCCCT         600
GCAGAACACCGCCGGAATTGTCGGTGCGCCATGGCCTCTGTCGCAGATACGACGCACTG     660
AAACTTGCCCGCTCGGGCTGTACTCGTGCGCAGTAAAGTTACAATGGTCAGCGGCCG       720
CCCGACCGATAGCGCGGAGTATTCACGCTGATATCAACGCCGACATTCGACATAGCAGA    780
CACTTTCGGTTACGCACGCCCAACCGGAAGTGAGTAACGACCGAAGGGGTGTAT          840

GTGGCAGGCAGCCAAAGCAAGCACGGGACCGATGAGCCGGTAAAACGCACCGCCACCAAG    900
 V  A  A  T  K  A  S  T  A  T  D  E  P  V  K  R  T  A  T  K
```

FIGURE 12a - 1

G (35721 and Erdman)

```
TCGCCCGGGCTTCCGCGTCCGGGGCCAAGACGGCCCCAAGGCGAACAGCGGGAAGTCC  960
 S  P  A  A  S  A  S  G  A  K  T  G  P  K  R  T  A  A  K  S
                                                       A
GCTAGTGGCTCCCCACCCGCGAAGCGGGCTACCAAGCCCGCGGCCCGGTCCGTCAAGCCC 1020
 A  S  G  S  P  P  A  K  R  A  T  K  P  A  A  R  S  V  K  P
GCCTCGGCACCCCAGGACACTACGACCAGCACCATCCCGAAAAGGAAGACCCGCGCCGCG 1080
 A  S  A  P  Q  D  T  T  T  S  T  I  P  K  R  K  T  R  A  A
GCCAAAATCCGCGCCGGAAGGCACCGTCGGCCGCGGACCAAGCCACGGGCG 1140
 A  K  S  A  A  A  K  A  P  S  A  R  G  H  A  T  K  P  R  A
CCCAAGGATGCCCAGCACGAAGCCGCAACGGATCCCGAGGACGCCCTGGACTCCGTCGAG 1200
 P  K  D  A  Q  H  E  A  A  T  D  P  E  D  A  L  D  S  V  E
GAGCTCGACGCTGAACCAGACCTCGACGTCGAGCCCGGCGAGGACCTCGACCTTGACGCC 1260
 E  L  D  A  E  P  D  L  D  V  E  P  G  E  D  L  D  L  D  A
GCCGACCTCAACCTCGATGACCTCGAGGACGACGAAGCCGACGTGGCGCCGGACGCCGACGACCTC 1320
 A  D  L  N  L  D  D  L  E  D  D  V  A  P  D  A  D  D  D  L
GACTCGGGCGACGACGAAGACCACGAAGACCTCGAAGCTGAGGCGGCCGTCGCGCCGGC 1380
 D  S  G  D  D  E  D  H  E  D  L  E  A  E  A  A  V  A  P  G
CAGACCGCCGATGACGACGAGGAGATCGCTGAACCCACCGAAAAGGACAAGGCCTCCGGT 1440
 Q  T  A  D  D  D  E  E  I  A  E  P  T  E  K  D  K  A  S  G
```

FIGURE 12a - 2

```
GATTTCGTCTGGGATGAAGAGACGAGTCGGAGGCCCTGCGTCAAGCACGCAAGGACGCCGAA 1500
 D  F  V  W  D  E  D  E  S  E  A  L  R  Q  A  R  K  D  A  E
CTCACCGCATCCGCCGACTCGGTTCGGCCTACCTCAAACAGATCGGCAAGGTAGGCGCTG 1560
 L  T  A  S  A  D  S  V  R  A  Y  L  K  Q  I  G  K  V  A  L
CTCAACGCCGAGGAAGAGGTCGAGCTAGCCAAGCGGATCGAGGCTGCCTGTACGCCACG 1620
 L  N  A  E  E  V  E  L  A  K  R  I  E  A  G  L  Y  A  T
CAGCTGATGACCGAGCTTAGCGAGCGGCGGGAAAAGCTGCCTGCCCCAGGCGCCGGAC 1680
 Q  L  M  T  E  L  S  E  R  G  E  K  L  P  A  A  Q  R  R  D
ATGATGTGGATCTGCCGCGACGGCGATCGCGCGGCGGAAAAACCATCTGCTGGAAGCCAACCTG 1740
 M  M  W  I  C  R  D  G  D  R  A  K  N  H  L  L  E  A  N  L
CGGCCTGGTGGTTTCGCTAGCCAAGCGCTACACCGGCCGGGGCATGGCGTTTCTCGACCTG 1800
 R  L  V  S  L  A  K  R  Y  T  G  R  G  M  A  F  L  D  L
ATCCAGGAAGGCAACCTGGGGCTGATCCGCGCGGTGGAGAAGTTCGACTACACCAAGGGG 1860
 I  Q  E  G  N  L  G  L  I  R  A  V  E  K  F  D  Y  T  K  G
TACAAGTTCTCCACCTACGCTGGTGGATTCGCCAGGCCATCACCCGGCCATGGCC 1920
 Y  K  F  S  T  Y  A  T  W  I  R  Q  A  I  T  R  A  M  A
GACCAGGCCCGCACCATCCGGTGCACATGGTCGAGGTGATCAACAAGCTGGGC 1980
 D  Q  A  R  T  I  R  I  P  V  H  M  V  E  V  I  N  K  L  G
CGGCATTCAACGGAGCTGCTGCAGGACCTGGGCCGCGAGCCCACGCCCGAGGAGAGCTGGCC 2040
 R  I  Q  R  E  L  L  Q  D  L  G  R  E  P  T  P  E  E  L  A
```

FIGURE 12a - 3

```
AAAGAGATGGACATCACCCCGGAGAAGGTGCTGGAAATCCAGCAATACGCCCGGGAGCCG 2100
 K  E  M  D  I  T  P  E  K  V  L  E  I  Q  Q  Y  A  R  E  P
ATCTCGTTGGACCAGACCATCGGCGACGAGGGCGACAGCCAGCTTGGCGATTTCATCGAA 2160
 I  S  L  D  Q  T  I  G  D  E  G  D  S  Q  L  G  D  F  I  E
GACAGCGAGGCGGTGGCCGTGCAGCGGGTGTCCTTCACTTTGCTGCAGGATCAACTG 2220
 D  S  E  A  V  V  A  V  D  A  V  S  F  T  L  L  Q  D  Q  L
CAGTCGGTGCTGGACACGCTCTCCGAGCGTGAGGCGGTGGTGCGGCTACGCTTCGGC 2280
 Q  S  V  L  D  T  L  S  E  R  E  A  G  V  V  R  L  R  F  G
CTTACGGACGGCCAGCCGCGCACCCTTGACGAGATCGGCCAGGTCTACGGCGTGACCCGG 2340
 L  T  D  G  Q  P  R  T  L  D  E  I  G  Q  V  Y  G  V  T  R
                                              A (35721)
GAACGCATCCGCCAGATCGAATCCAAGACTATGTCGAAGTTGCGCCATCCGAGCCGCTCA 2400
 E  R  I  R  Q  I  E  S  K  T  M  S  K  L  R  H  P  S  R  S
                                               H
CAGGTCCTGCGCGACTACCTGGACTGAGAGGCCCGCGAGGGGACCAACGTAGCGGGCC 2460
 Q  V  L  R  D  Y  L  D  *
CCCATGTCAGCTAGCCGCACCATGGTCTCGTCCGGATCGGAGTTCGAATCAGCCGTCGGC 2520
TACTCGCGCGGGTACGCATCGGGCCACTCGTGGTGGCCGGAACGACCGGCAGCGGGC 2580
   C (WAg201, 35721 and Erdman)
GATGATATCGTCGCTCAGACGCGAGACGCTCTGCGCCGCATCGAGATTGCGCTCGGACAG 2640
```

FIGURE 12a - 4

GCCGGGCGCAACTCTGGCCGACGTGGTCCGTACCCGCATCTATGTGACCGATATTTCCCGC 2700
TGGCGCGAGGTCGGGGAAGTGCATGCACAGGCTTTCGGCAAGATC 2745

FIGURE 12a - 5

MYCOBACTERIA VIRULENCE FACTORS AND A NOVEL METHOD FOR THEIR IDENTIFICATION

CROSS-REFERENCE TO RELATED APPLICATIONS

This application is a continuation-in-part of U.S. Ser. No. 08/292,695 (attorney docket no. 252372000221) filed Aug. 18, 1994, now abandoned, which is a continuation-in-part of U.S. Ser. No. 08/265,579 (attorney docket no. 252372000220) filed Jun. 24, 1994, now abandoned, which is a continuation-in-part of U.S. application Ser. No. 08/201,880 (attorney docket no. 252372000200) filed Feb. 24, 1994, now abandoned, all of which are hereby incorporated herein in their entirety.

TECHNICAL FIELD

This invention relates to polynucleotide sequence(s) associated with virulence in mycobacteria, methods for isolating such sequence(s), and the use of such sequence(s) in human and animal medical practice. It also relates to polypeptides encoded in the sequences.

BACKGROUND ART

The mycobacteria are rod-shaped, acid-fast, aerobic bacilli that do not form spores. Several species of mycobacteria are pathogenic to humans and/or animals, and determining factors associated with their virulence are of prime importance. For example, tuberculosis is a worldwide health problem which causes approximately 3 million deaths each year (17), yet little is known about the molecular basis of tuberculosis pathogenesis. The disease is caused by infection with *Mycobacterium tuberculosis*; tubercle bacilli are inhaled and then ingested by alveolar macrophages. As is the case with most pathogens, infection with *M. tuberculosis* does not always result in disease. The infection is often arrested by a developing cell-mediated immunity (CMI) resulting in the formation of microscopic lesions, or tubercles, in the lung. If CMI does not limit the spread of *M. tuberculosis*, caseous necrosis, bronchial wall erosion, and pulmonary cavitation may occur. The factors that determine whether infection with *M. tuberculosis* results in disease are incompletely understood.

The tuberculosis complex is a group of four mycobacterial species that are so closely related genetically that it has been proposed that they be combined into a single species. Three important members of the complex are *Mycobacterium tuberculosis*, the major cause of human tuberculosis; *Mycobacterium africanum*, a major cause of human tuberculosis in some populations; and *Mycobacterium bovis*, the cause of bovine tuberculosis. None of these mycobacteria is restricted to being pathogenic for a single host species. For example, *M. bovis* causes tuberculosis in a wide range of animals including humans in which it causes a disease that is clinically indistinguishable from that caused by *M. tuberculosis*. Human tuberculosis is a major cause of mortality throughout the world, particularly in less developed countries. It accounts for approximately eight million new cases of clinical disease and three million deaths each year. Bovine tuberculosis, as well as causing a small percentage of these human cases, is a major cause of animal suffering and large economic costs in the animal industries.

Antibiotic treatment of tuberculosis is very expensive and requires prolonged administration of a combination of several antituberculosis drugs. Treatment with single antibiotics is not advisable as tuberculosis organisms can develop resistance to the therapeutic levels of all antibiotics that are effective against them. Strains of *M. tuberculosis* that are resistant to one or more antituberculosis drugs are becoming more frequent and treatment of patients infected with such strains is expensive and difficult. In a small but increasing percentage of human tuberculosis cases the tuberculosis organisms have become resistant to the two most useful antibiotics, isoniazid and rifampicin. Treatment of these patients presents extreme difficulty and in practice is often unsuccessful. In the current situation there is clearly an urgent need to develop new methods for detecting virulent strains of mycobacteria and to develop tuberculosis therapies.

There is a recognized vaccine for tuberculosis which is an attenuated form of *M. bovis* known as BCG. This is very widely used but it provides incomplete protection. The development of BCG was completed in 1921 but the reason for its avirulence was and has continued to remain unknown (Grange et al., 1983). Methods of attenuating tuberculosis strains to produce a vaccine in a more rational way have been investigated but have not been successful for a variety of reasons (Young, 1993). However, in view of the evidence that dead *M. bovis* BCG was less effective in conferring immunity than live BCG (Block and Segal, 1955), there exists a need for attenuated strains of mycobacteria that can be used in the preparation of vaccines.

A variety of compounds have been proposed as virulence factors for tuberculosis but, despite numerous investigations, good evidence to support these proposals is lacking. Nevertheless, the discovery of a virulence factor or factors for tuberculosis is still regarded as important and is a very active area of current research. This is because such a discovery would not only enable the possible development of a new generation of tuberculosis vaccines but might also provide a target for the design or discovery of new or improved anti-tuberculosis drugs or therapies.

The ability to transfer and express recombinant DNA among the mycobacteria, first demonstrated in 1987 (Jacobs et al.), enables the usage of molecular genetics to elucidate pathogenic mechanisms. But, the present lack of evidence of homologous recombination in the pathogenic mycobacteria has prevented the application of allele exchange systems (Kalpana et al.) for the analysis.

One of the first examples of in vivo selection for virulent bacteria was demonstrated by the classic work of Griffith et al. in 1928. Griffith using pneumococci observed that, as a result of genetic exchange, virulent, capsulated pneumococci were recovered from mice infected with a mixture of live attenuated, non-capsulated pneumococci and heat-killed capsulated pneumococci (Griffith, 1928). However, similar systems have not been demonstrated in mycobacteria.

Bacterial RNA polymerases are composed of a core enzyme with the subunit composition $\alpha_2\beta\beta'$ and one of a variety of sigma factors. Transcription responses to changes in growth conditions are modulated by multiple RNA polymerases having different sigma factors which promote transcription of different classes of promoters. The principal sigma factor plays a central role in bacterial by promoting essential "housekeeping" genes. Genes for alternative sigma factors are present in all bacteria and have been shown to promote specific virulence genes in some pathogens (Fang, 1992; Deretic 1994). However, loss of a virulence phenotype due to mutation in a principal sigma factor has not been reported. Streptomyces sp. contain several homologues of principal sigma factors (Buttner, 1990) which are not essential for normal growth but which appear to have a function under certain growth conditions.

References cited in the Background Art

1. Anon (1972) TRUDEAU MYCOBACTERIAL CULTURE COLLECTION (Trudeau Institute Inc., P.O. Box 59, Saranac Lake, N.Y. 12983).

2. Belisle, J. T., Pascopella, L., Inamine, J. M., Brennan, P. J., and W. R. Jacobs, (1991) "Isolation and expression of a gene cluster responsible for biosynthesis of the glycopeptidolipid antigens of *Mycobacterium avium,*" *J. Bacteriol.* 173:6991–6997.

3. Bloom, B. R., Tuckman, M., Kalpana, G. V., and W. R. Jacobs, unpublished data.

4. Boyer, H., and D. Roulland-Dussoin. (1969) "A complementation analysis of the restriction and modification of DNA in *Escherichia coli,*" *J. Mol. Biol.* 41:459–472.

5. Collins, D. M., and G. W. de Lisle. (1984) "DNA restriction endonuclease analysis of *Mycobacterium tuberculosis* and *Mycobacterium bovis* BCG," *J. Gen. Microbiol.* 130:1019–1021.

6. Collins, F. M., and M. M. Smith. (1969) "A comparative study of the virulence of *Mycobacterium tuberculosis* measured in mice and guinea pigs," *American Review of Respiratory Disease* 100:631–639.

7. Collins, D. M., S. K. Erasmuson, D. M. Stephens, G. F. Yates, and G. W. de Lisle. (1993) "DNA fingerprinting of *Mycobacterium bovis* strains by restriction fragment analysis and hybridization with the insertion elements IS1081 and IS6110," *J. Clin. Microbiol.* 31:1143–1147.

8. Dannenberg, A. M., Jr., (1991) "Delayed type hypersensitivity and cell mediated immunity in the pathogenesis of tuberculosis," *Immunology Today* 12:228–233.

9. Gallagher, J., and D. M. Horwill, (1977) "A selective oleic acid albumin medium for the cultivation of *Mycobacterium bovis,*" *J. Hyg. Camb.* 79:155–160.

10. Grange, J. M., J. Gibson, T. W. Osborne, C. H. Collins and M. D. Yates, (1983) "What is BCG?" *Tubercle* 64:129–139.

11. Griffith F., (1928) "Significance of pneumococcal types," *J. Hyg.* 27:113–159.

12. Grosskinsky, C. M., Jacobs, W. R., Jr., Clark-Curtiss, J. E., and B. R. Bloom, (1989) "Genetic relationships among *Mycobacterium leprae, Mycobacterium tuberculosis,* and candidate leprosy vaccine strains determined by DNA hybridization: Identification of an M. leprae-specific repetitive sequence," *Infect. Immun.* 57:1535,1541.

13. Jacobs, W. R., Barrett, J. F., Clark-Curtiss, J. E., and R. Curtiss III, (1986) "In vivo repackaging of recombinant cosmid molecules for analysis of *Salmonella typhimurium, Streptococcus mutans,* and mycobacterial genomic libraries," *Infect. Immun.* 52:101–109.

14. Jacobs, W. R., G. V. Kalpana, J. D. Cirillo, L. Pascopella, S. B. Snapper, R. A. Udani, W. Jones, R. G. Barletta and B. R. Bloom, (1991) "Genetic systems for mycobacteria," *Methods Enzymol.* 204:537–555.

15. Jacobs, W. R., Tuckman, M., and B. R. Bloom, (1987) "Introduction of foreign DNA into mycobacteria using a shuttle plasmid," *Nature* 327:532–535.

16. Kalpana, G. V., Bloom, B. R., and W. R. Jacobs, (1991) "Insertional mutagenesis and illegitimate recombination in mycobacteria," *Proc. Natl. Acad. Sci. USA* 88:5433–5437.

17. Kochi, A., (1991) "The global tuberculosis situation and the new control strategy of the World Heath Organization," *Tubercle* 72:1–12.

18. Lee, M. H., Pascopella, L., Jacobs, W. R., and C. F. Hatfull, (1991) "Site-specific integration of mycobacteriophage L5: Integration-proficient vectors for *Mycobacterium smegmatis, Mycobacterium tuberculosis,* and bacille Clamette-Guerin," *Proc. Natl. Acad. Sci. U.S.A.* 88:3111–3115.

19. Mackaness, G. B., Smith, N., and A. Q. Wells, (1954) "The growth of intracellular tubercle bacilli in relation to their virulence," *Am. Rev. Tuberc.* 69:479–494.

20. North, R. J., and A. A. Izzo, (1993) " Mycobacterial virulence: Virulent strains of *Mycobacterium tuberculosis* have faster in vivo doubling times and are better equipped to resist growth inhibiting functions of the macrophages in the presence and absence of specific immunity," *J. Exp. Med.* 177:1723–1734.

21. Oatway, W. H., Jr., and W. Steenken, Jr., (1936) "The pathogenesis and fate of tubercle produced by dissociated variants of tubercle bacilli," *J. Inf. Dis. 59:306–325.*

22. Pascopella, L., F. M. Collins, J. M. Martin, M. H. Lee, G. F. Hatfull, B. R. Bloom and W. R. Jacobs, "In vivo complementation in *Mycobacterium tuberculosis* to identify a genomic fragment associated with virulence," *Infection and Immunity* 62: 1313–1319.

23. Pierce, C. H., Dubos, R. J., and W. B. Schaefer, (1953) "Multiplication and survival of tubercle bacilli in the organs of mice," *J. Exp. Med.* 97:189–206.

24. Sambrook, J., E. F. Fritsch and T. Maniatis, (1989) MOLECULAR CLONING: A LABORATORY MANUAL (Cold Spring Harbor Laboratory, Cold Spring Harbor, N.Y.).

25. Steenken, W., Jr., and L. U. Gardner, (1946.) "History of H37 strain tubercle bacillus," *Amer. Rev. Tuberc.* 54:62–66.

26. Steenken, W., Jr., Oatway, W. H., Jr., and S. A. Petroff, (1934) "Biological studies of the tubercle bacillus. III. Dissociation and pathogenicity of the R and S variants of the human tubercle bacillus ($H_{37}$)," *J. Exp. Med.* 60:515–540.

27. Stover, C. K., de la Cruze, V. F., Fuerst, T. R., Burlein, J. E., Benson L. A., Bennett L. T., Bansal, G. P., Young, J. F., Lee, M. H., Hatful, G. F., Snapper, S. B., Barletta, R. G., Jacobs, W. R., and B. R. Bloom, (1991) "New use of BCG for recombinant vaccines," *Nature* 351:456–460.

28. van Soolingen, D., P. W. M. Hermans, P. E. W. de Haas, D. R. Soll and J. D. A. van Embden, (1991) "Occurrence and stability of insertion sequences in *Mycobacterium tuberculosis* complex strains: evaluation of an insertion sequence-dependent DNA polymorphism as a tool in the epidemiology of tuberculosis," *J. Clin. Microbiol.* 29:2578–2586.

29. Weis, H., (1991) CURRENT PROTOCOLS IN MOLECULAR BIOLOGY, Supplement 13, 5.3. (Greene Publishing Associates, New York, eds., F. M. Ausubel, R. Brent, R. E. Kingston, D. D. Moore, J. G. Siedman, J. A. Smith, and K. Struhl).

30. Young, D. B. and S. T. Cole, (1993) "Leprosy, tuberculosis, and the new genetics," *J. Bacteriol.* 175:1–6.

31. Block, H. and W. Segal, *Am. Rev. Tuberc. Pulm. Dis* 71:228–248.

32. Fang, C.F. et al., (1992) *Proc. Natl. Acad. Sci. USA* 89:11978–11982.

33. Deretic., V. et al, (1994) *J. Bact.* 176:2773–2780.

34. Buttner, M.J., et al., (1990) *J. Bact.* 172: 3367–3378.

SUMMARY OF THE INVENTION

The present invention provides isolated and recombinant polynucleotide sequences associated with virulence determinants in members of the genus mycobacteria, particularly those of the tuberculosis complex, and more particularly in *M. tuberculosis* and *M. bovis*. Based upon homology to sigma factors from other microorganisms, one of the mycobacterial sequences associated with virulence encodes a putative sigma-like factor.

The DNA sequences encoding factors associated with virulence were found by the use of in vivo complementation assays, more particularly by complementation in a guinea pig model and in a mouse model. The in vivo genetic complementation systems utilized integrating shuttle cosmid libraries to identify potential virulence genes. Thus, the invention also provides techniques to identify a DNA sequence or sequences associated with virulence determinants in *M. tuberculosis* and *M. bovis* and similar DNA sequences in other tuberculosis complex strains and in strains of other mycobacterial species and in species of other pathogenic organisms.

Accordingly, embodiments of the invention include the following.

A method for identifying a DNA sequence or sequences associated with virulence determinants in *M. tuberculosis* and *M. bovis* and similar DNA sequences in other tuberculosis complex strains and in strains of other mycobacterial species and in species of other pathogenic organisms comprising the steps of:

a) preparing a genomic DNA library of the pathogenic organism;

b) constructing an integrating shuttle vector containing genomic inserts prepared in step a);

c) transforming via homologous recombination a population of avirulent organisms;

d) isolating the recombinants;

e) inoculating a subject with an adequate inoculum of the recombinants in order to select virulent recombinants;

f) isolating the virulent recombinants; and g) identifying the DNA insert which confers virulence.

This method may be performed with individuals that are mice or guinea pigs.

An isolated polynucleotide comprised of a segment of less than 3 kb that is essentially homologous to a mycobacterial DNA sequence associated with virulence in mycobacteria, wherein the mycobacterial DNA sequence encodes a sigma factor.

An isolated polynucleotide comprised of a segment of less than 3 kb that encodes a polypeptide or fragment thereof, wherein the polypeptide is associated with virulence in mycobacteria and is a sigma factor. The polypeptide may be essentially homologous to the polypeptide encoded in FIG. 9.

An isolated polynucleotide comprised of at least 15 sequential nucleotides homologous to a sequence of polynucleotides in FIG. 9.

A recombinant polynucleotide comprised of a sequence of at least 15 sequential nucleotides homologous to a sequence of polynucleotides in FIG. 9.

A recombinant polynucleotide comprised of a segment of less than 3 kb that encodes a polypeptide or fragment thereof, wherein the polypeptide is associated with virulence in mycobacteria and is a sigma factor.

An expression vector comprised of the recombinant polynucleotide described above.

An isolated polynucleotide comprised of a linear segment of at least 15 nucleotides that is substantially homologous to mycobacterial DNA in a plasmid selected from the group consisting of pUHA$_1$, pUHA2, pUHA3, pUHA4, pUHA5, pUHA6, pUHA7, pUHA8, pUHA9, pUHA11, pYUB352, pYUB353, and pYUB354.

A host cell comprised of any of the above-described isolated polynucleotides, including expression vectors.

A diagnostic kit comprised of a polynucleotide and a buffer packaged in suitable vials, wherein the polynucleotide is any of the above-described isolated polynucleotides.

An isolated polypeptide substantially homologous to a polypeptide associated with virulence in mycobacteria or a fragment thereof, wherein the mycobacterial polypeptide is a sigma factor. The mycobacterial polypeptide may be one that is encoded in a DNA sequence shown in FIG. 9.

An isolated polynucleotide comprised of a segment of less than 3 kb that is essentially homologous to a mycobacterial DNA sequence associated with avirulence in mycobacteria, wherein the mycobacterial DNA sequence encodes a sigma factor.

A method for producing an altered property in a wild-type bacterial strain other than *M. bovis* comprising mutagenizing a principal sigma factor in the bacteria, wherein the mutagenizing results in converting an arginine to a histidine in the principal sigma factor, and wherein the conversion occurs at a similar position to that present in *M. bovis* ATCC 35721. This method includes altering the virulence properties of the bacterial strain.

A method of using a bacterial strain prepared by the method described above, the method comprising preparing a vaccine by mixing a pharmacologically effective dose of the strain with a pharmaceutically acceptable suitable excipient.

□, vector arm; _____, insert DNA from *M. bovis* Wag200.

Figure 3:
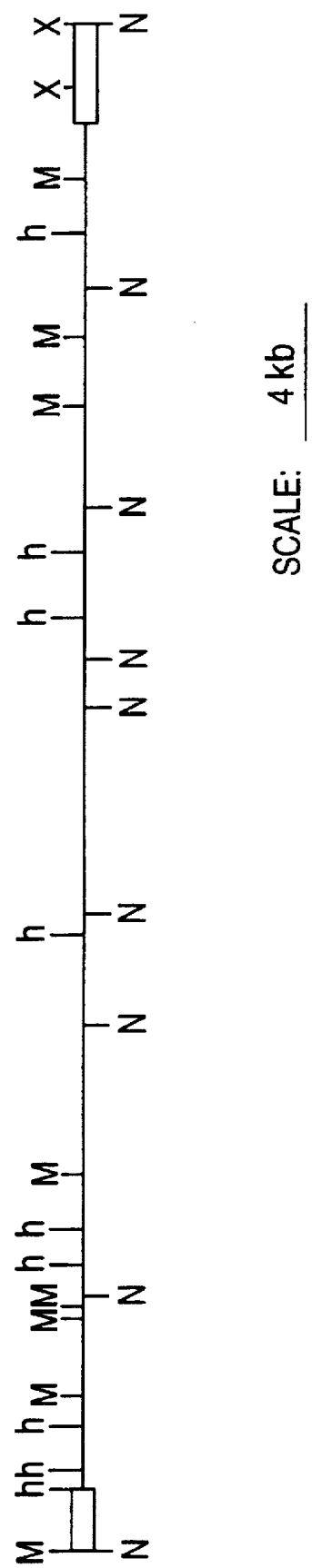

FIG. 3 is a restriction map of cosmid PUHA3 in linear form starting with the NotI site at position 2024 of pYUB178:h, NheI; M, MluI; N, NotI, X, XbaI.

Figure 4A:
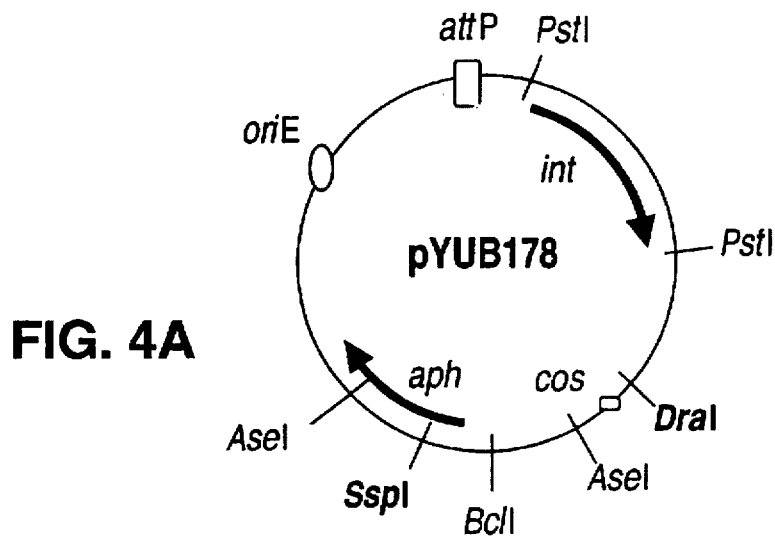
Figure 4B:
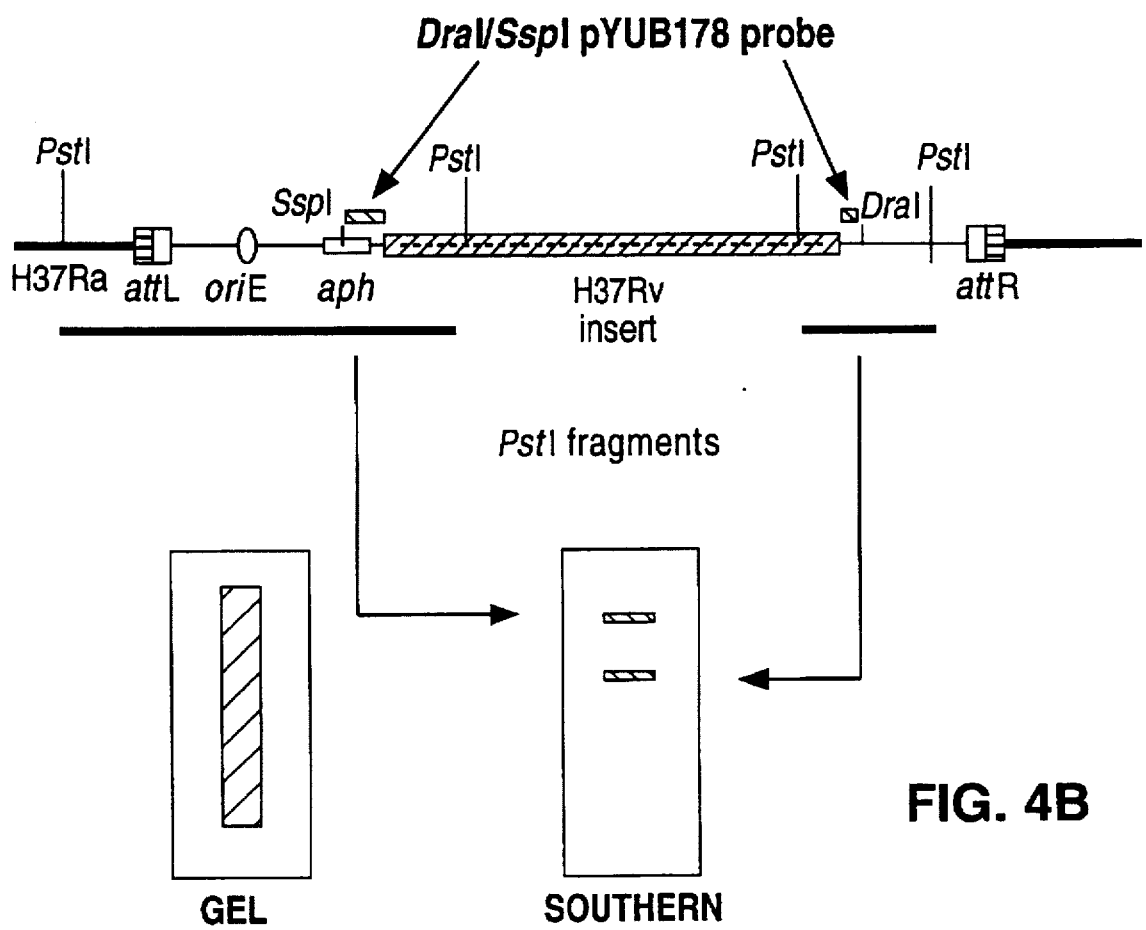
Figure 4C:
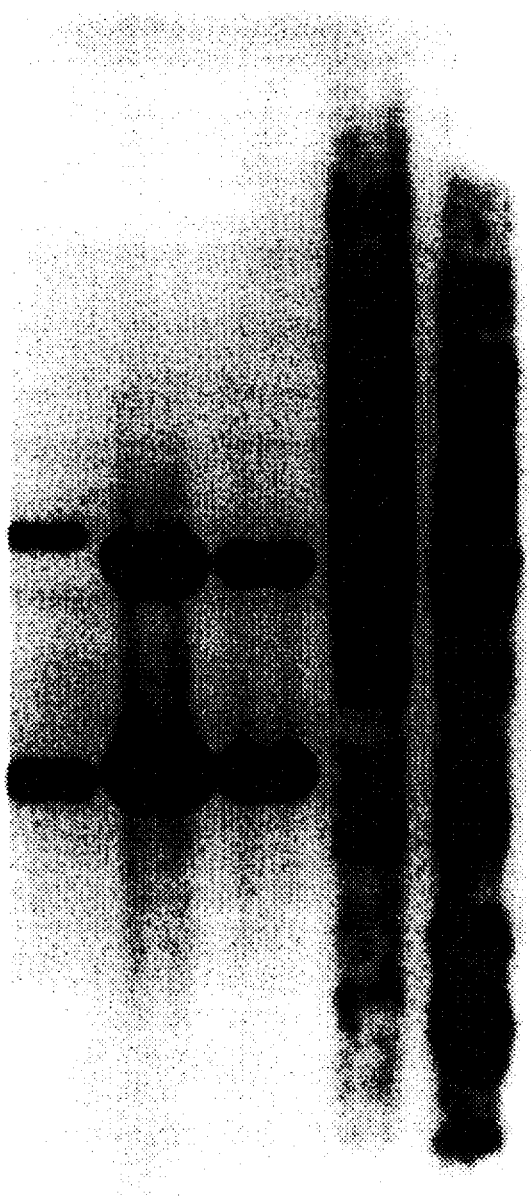

FIGS. 4A–C represent a map of the integrating shuttle cosmid, pYUB178, and analysis of individual clones and pools of H37Ra(pYUB178::H37Rv).

FIG. 4A shows the components that allow integration of pYUB178 into the mycobacterial genomes are attP and int. The pYUB178 cosmid contains an *E. coli* ori, the L5 attp, the L5 int, a kanamycin resistance gene, aph, derived from Tn903, lambda cos, and a unique cloning site, BclI.

FIG. 4B ia a schematic showing identification of the pYUB178/H37Rv junctional fragments within the chromosome of a H37Ra recombinant containing pYUB178::H37Rv DNA. PstI-digested chromosomal DNA is separated by gel electrophoresis and hybridized with a labeled probe from pYUB178. The probe is the 1.1 kb DraI/SspI DNA fragment of pYUB178 that flanks the BclI cloning site. The integrated pYUB178::H37Rv cosmid can be detected only by the presence of pYUB178-hybridizing DNA fragments. The PstI sites on either side of the H37Rv insert are fixed. Thus, the size of hybridizing DNA fragments varies with the H37Rv insert DNA.

FIG. 4C are half-tones of gels showing individual H37Ra recombinants containing pYUB178::H37Rv cosmid clones were isolated from mouse lung tissue after spleen passage of recombinant pools, experiment J5P (see Table 9). Pools of H37Ra(pYUB178::H37Rv) were collected and passaged in broth culture. The chromosomal DNAs from pools and individual clones were isolated, digested with PstI, separated by agarose gel electrophoresis and transferred to a nylon filter to hybridize with the 1.1 kb DraI/SspI DNA fragment of pYUB178. Lanes 1–3, the H37Rv DNA junctional fragments of in vivo-selected individual clones of pool 2; lanes 4 and 5, the H37Rv DNA junctional fragments of members of pool 3, before (lane 4) and after (lane 5) in vitro passage.

Figure 5A:
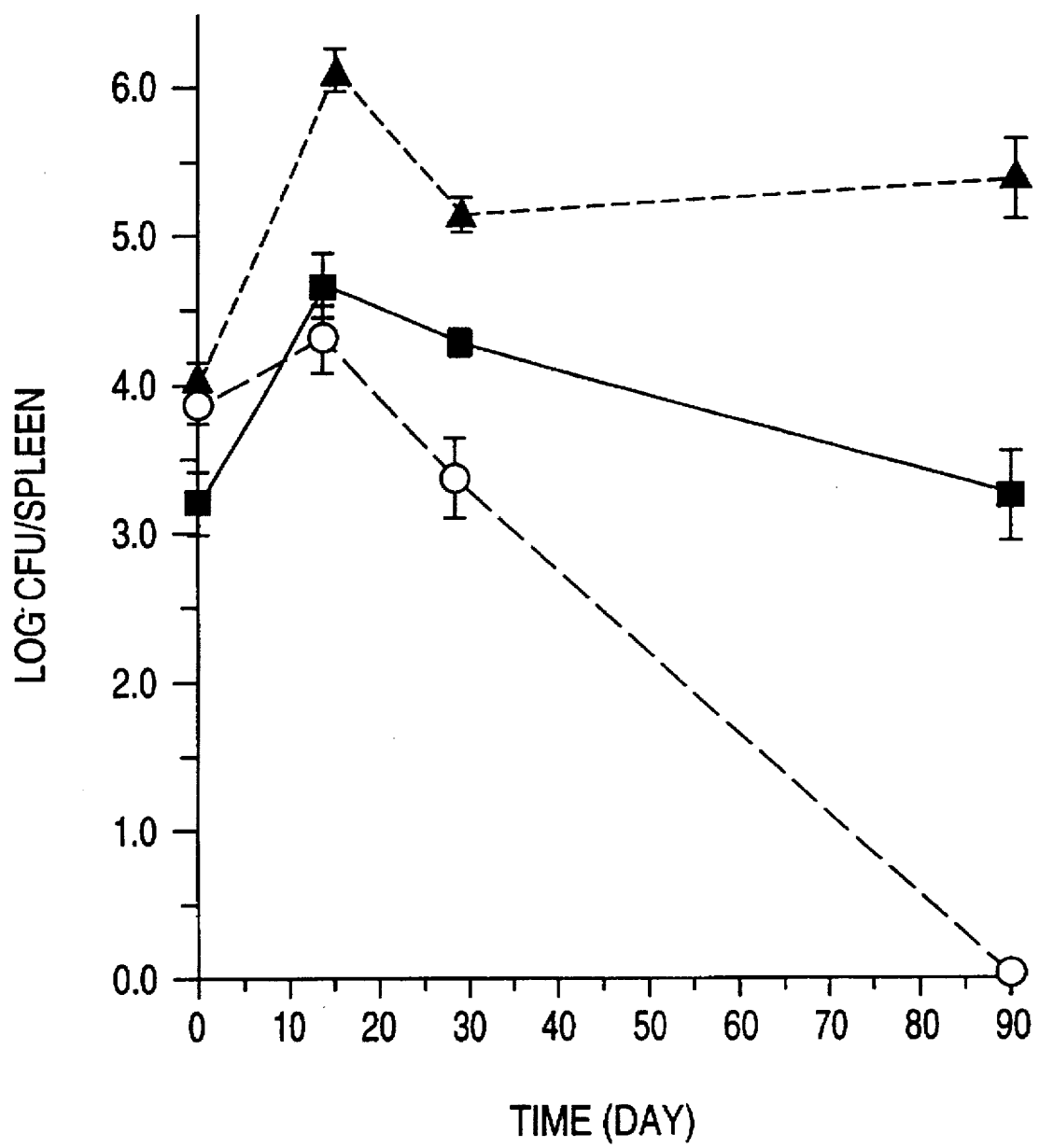
Figure 5B:
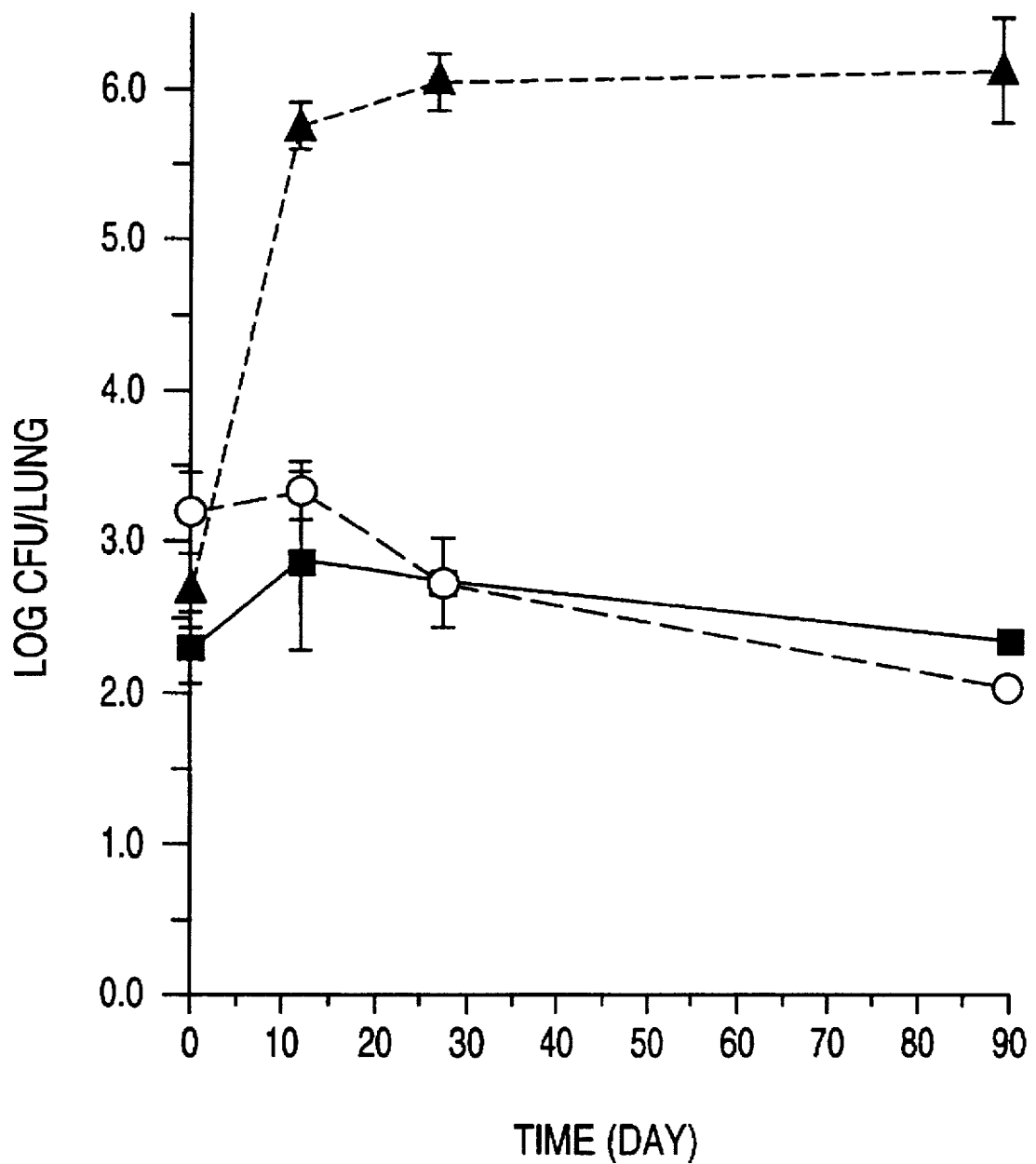

FIGS. 5A–B shows the growth of in vivo-selected H37Ra (pYUB178::H37Rv) clones in mouse lung and spleen. Growth rates of clones $mc^2$ 806, H37Rv, and $mc^2$816 were measured and compared. The growth rate of $mc^2$806 is represented by solid squares on the solid lines, the growth rate of $mc^2$816 is represented by the open circles on the dotted lines, and the growth rate of H37Rv is represented by solid triangles on the dotted lines. These data are representative of three experiments. See text and Table 9, experiment J33, for experimental details.

FIG. 5A shows growth in spleen.

FIG. 5B shows growth in lung.

Figure 6A:
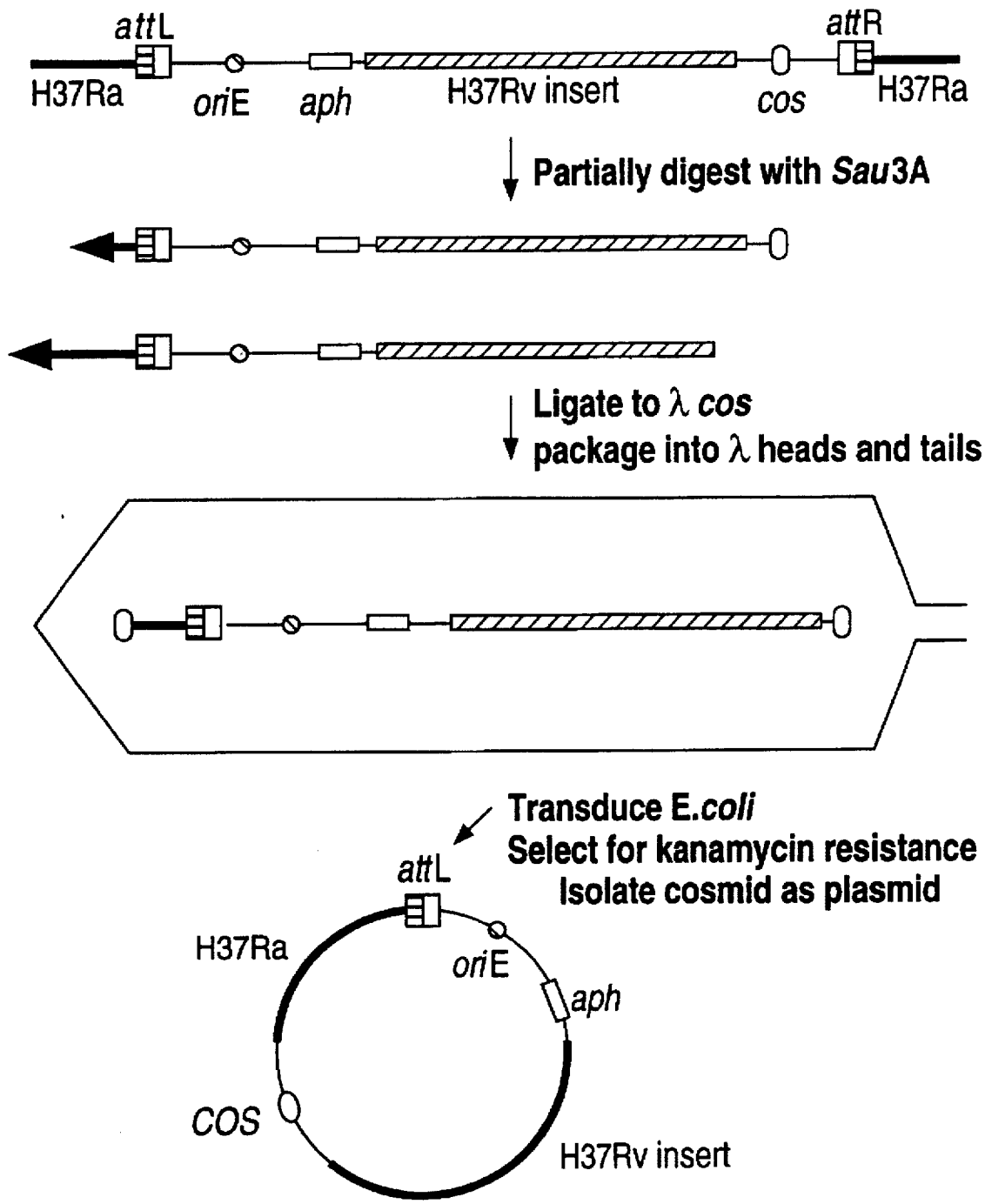
Figure 6B:
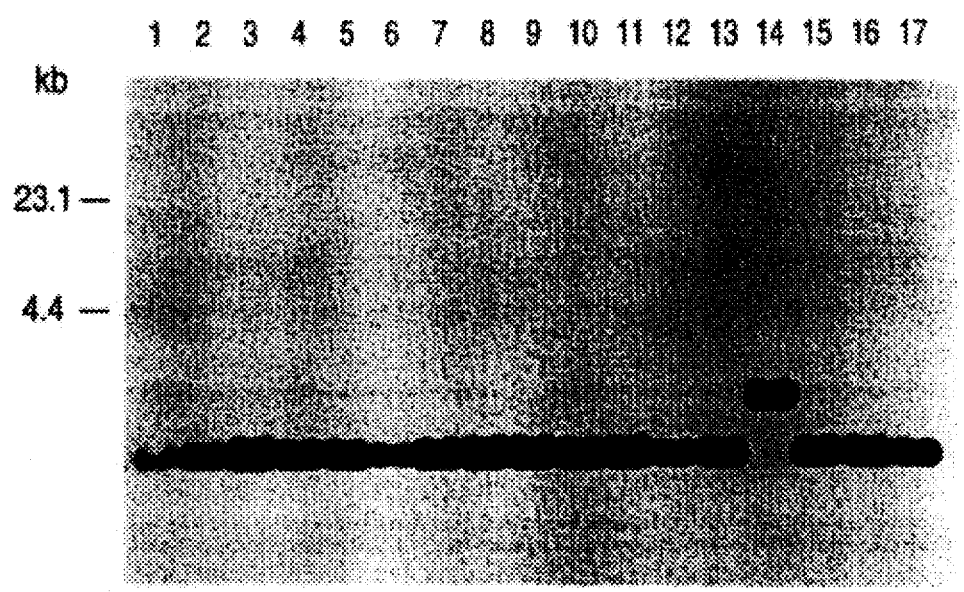

FIGS. 6A–B illustrate the retrieval of H37Rv-containing cosmids from the $mc^2$806 chromosome.

FIG. 6A is a schematic illustrating the strategy used to retrieve the H37Rv insert DNA from the integrated cosmids in H37Ra(pYUB178::H37Rv) recombinants.

FIG. 6B is a half-tone of an autoradiograph showing a Southern hybridization of AseI and EcoRI digests of $mc^2$806 chromosomal DNA, or cosmid DNAs that were retrieved from the chromosome of $mc^2$806. The 436 bp AseI/BclII fragment of pYUB178 that contained cos was used as a probe. Lane 1, $mc^2$806 chromosomal DNA, lanes 2 to 17, DNA from sixteen individual retrieved cosmids.

Figure 7:
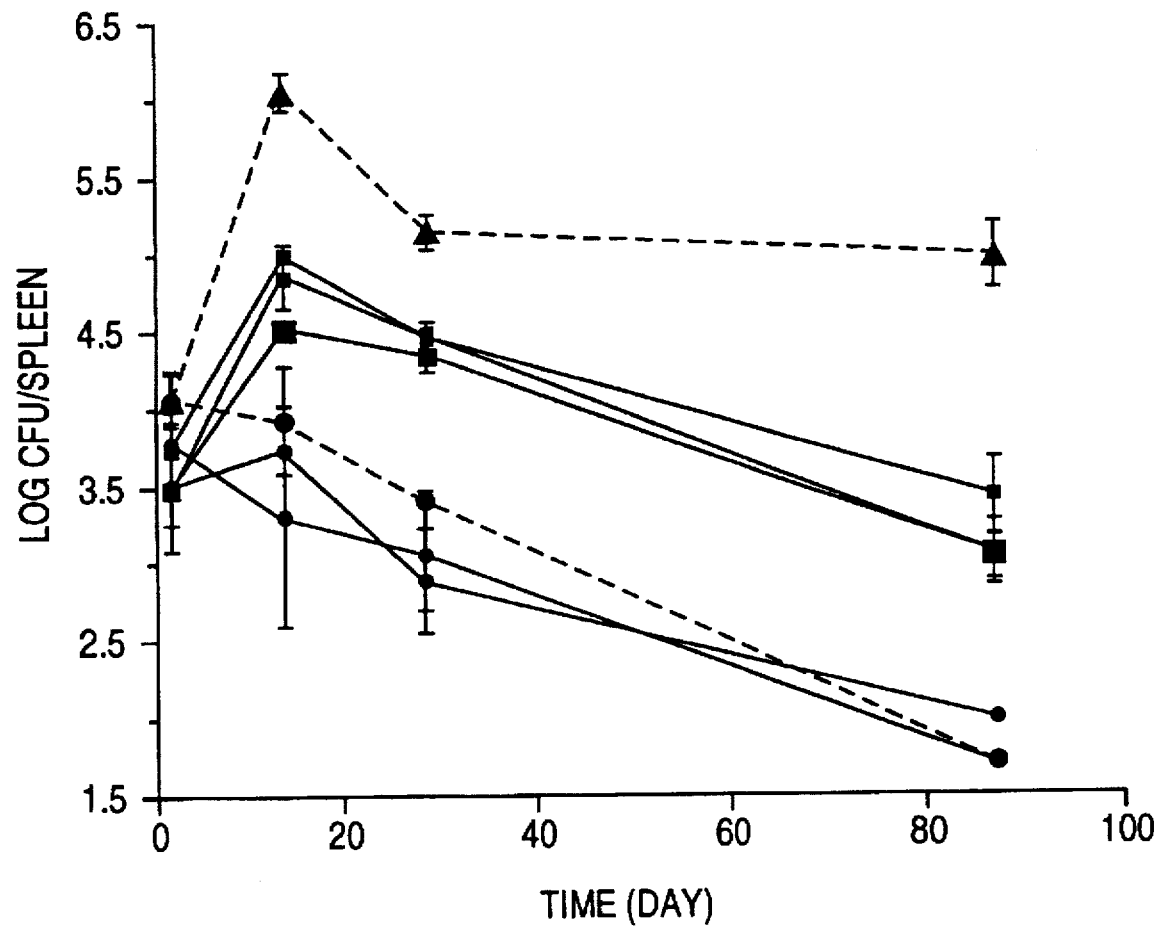

FIG. 7 is a graph showing the growth of H37Ra recombinants containing pYUB352-overlapping and -nonoverlapping cosmids. H37Ra was separately transformed with pYUB352-overlapping cosmids, pYUB353 and pYUB354, and with unrelated cosmids, pYUB355 and pYUB356. Growth of each recombinant was measured over a time course in mouse spleen. See Table 9, experiment J36. The growth of pYUB353- and pYUB354-containing H37Ra recombinants is represented by the small squares on the solid lines. The growth of $mc^2$806 is represented by the large squares on the solid lines. The growth of pYUB355- and pYUB356-containing H37Ra recombinants is represented by the small circles on the solid lines. The growth of $mc^2$816 is represented by the large circles on the dotted lines. The growth of H37Rv is represented by the triangles on the dotted lines.

Figure 8A:
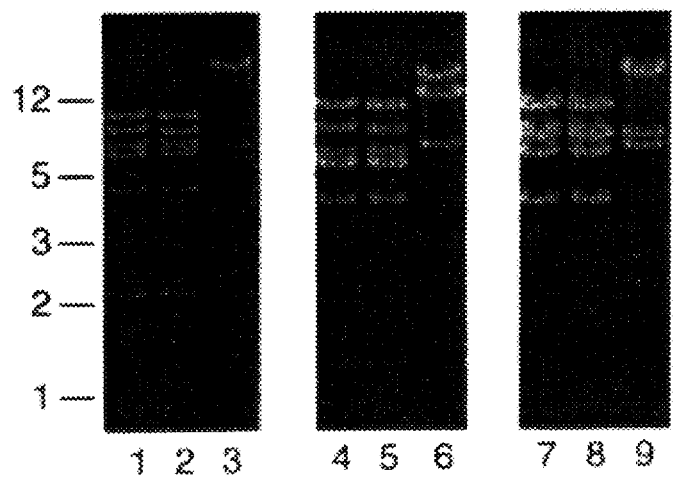
Figure 8B:
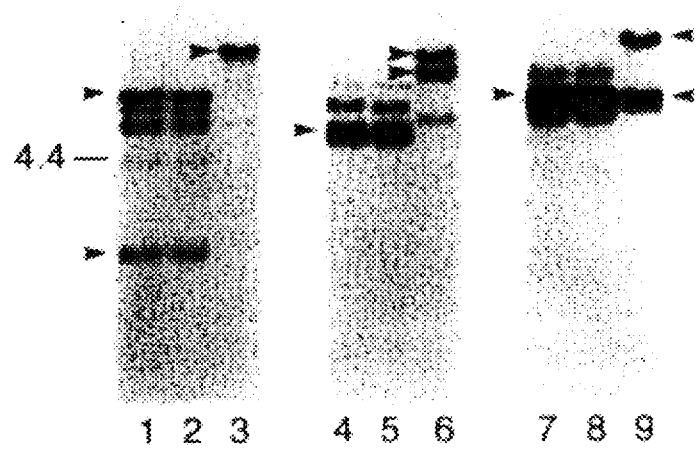
Figure 8C:
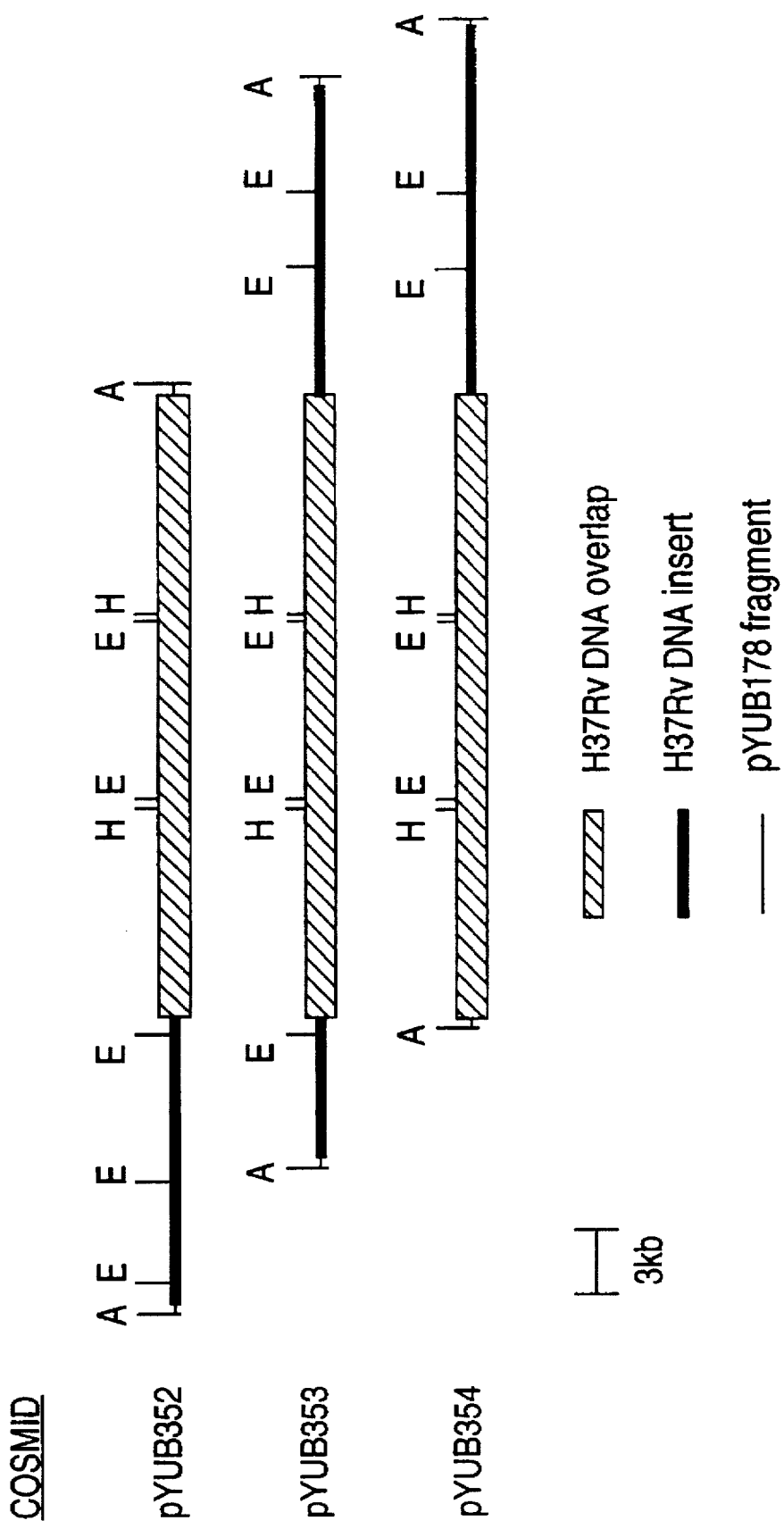

FIGS. 8A–C represent the restriction map of the ivg region of H37Rv DNA in pYUB352-overlapping cosmids. Restriction digests of pYUB352, pYUB353, and pYUB354 were performed with EcoRI and HindIII.

FIG. 8A is a half-tone reproduction of gels showing digested DNA fragments which were separated by agarose gel electrophoresis.

FIG. 8B is a half-tone reproduction of gels showing DNA fragments which were hybridized to the AseI fragment of pYUB352 that included its entire H37Rv insert with flanking pYUB178 DNA sequences. The arrows point to DNA fragments that hybridize to pYUB178 DNA probes. These bands are junctional fragments. Lanes 1–3 are digests of pYUB352, lanes 4–6 are digests of pYUB353, and lanes 7–9 are digests of pYUB354. Lanes 1, 4, and 7 show EcoRI digestion patterns, lanes 2, 5, and 8 show EcoRI and HindIII double digestion patterns, and lanes 3, 6, and 9 show HindIII digestion patterns.

FIG. 8C is a schematic illustrating data gathered from these molecular analyses and the functional analyses shown in FIG. 7 allowed the construction of the physical map of the ivg region of H37Rv that is present in cosmids pYUB352, pYUB353, and pYUB354. A=AseI, E=EcoRI, H=HindIII.

Figure 1:
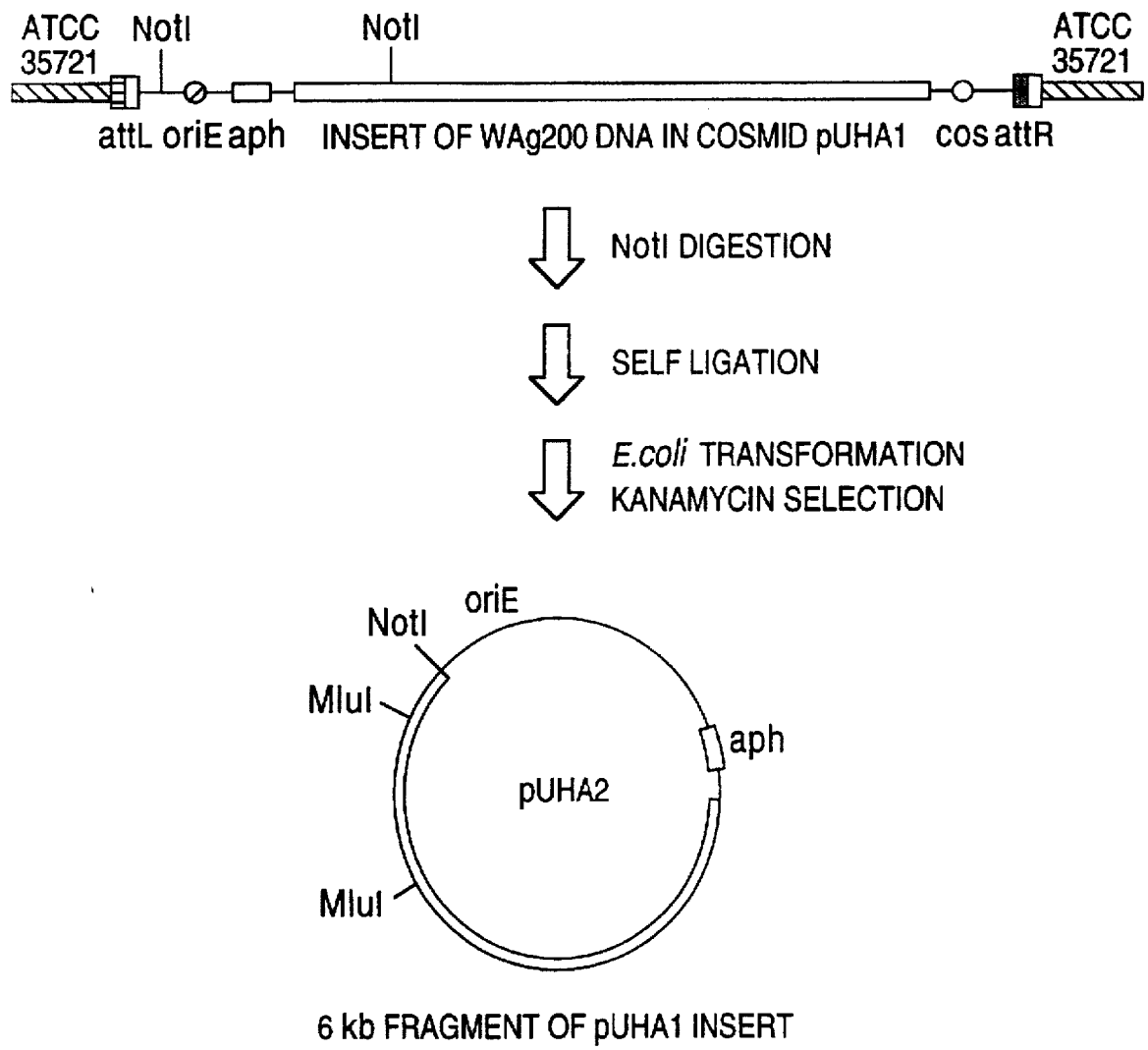
FIG. 1 is a schematic illustrating the strategy for recovering part of cosmid pUHA1 from *M. bovis* WAg300 which is a member of the *M. bovis* ATCC35721(pYUB178::*M. bovis* WAg200) library and which has increased virulence for guinea pigs. The diagrams are not to scale.
Figure 2:
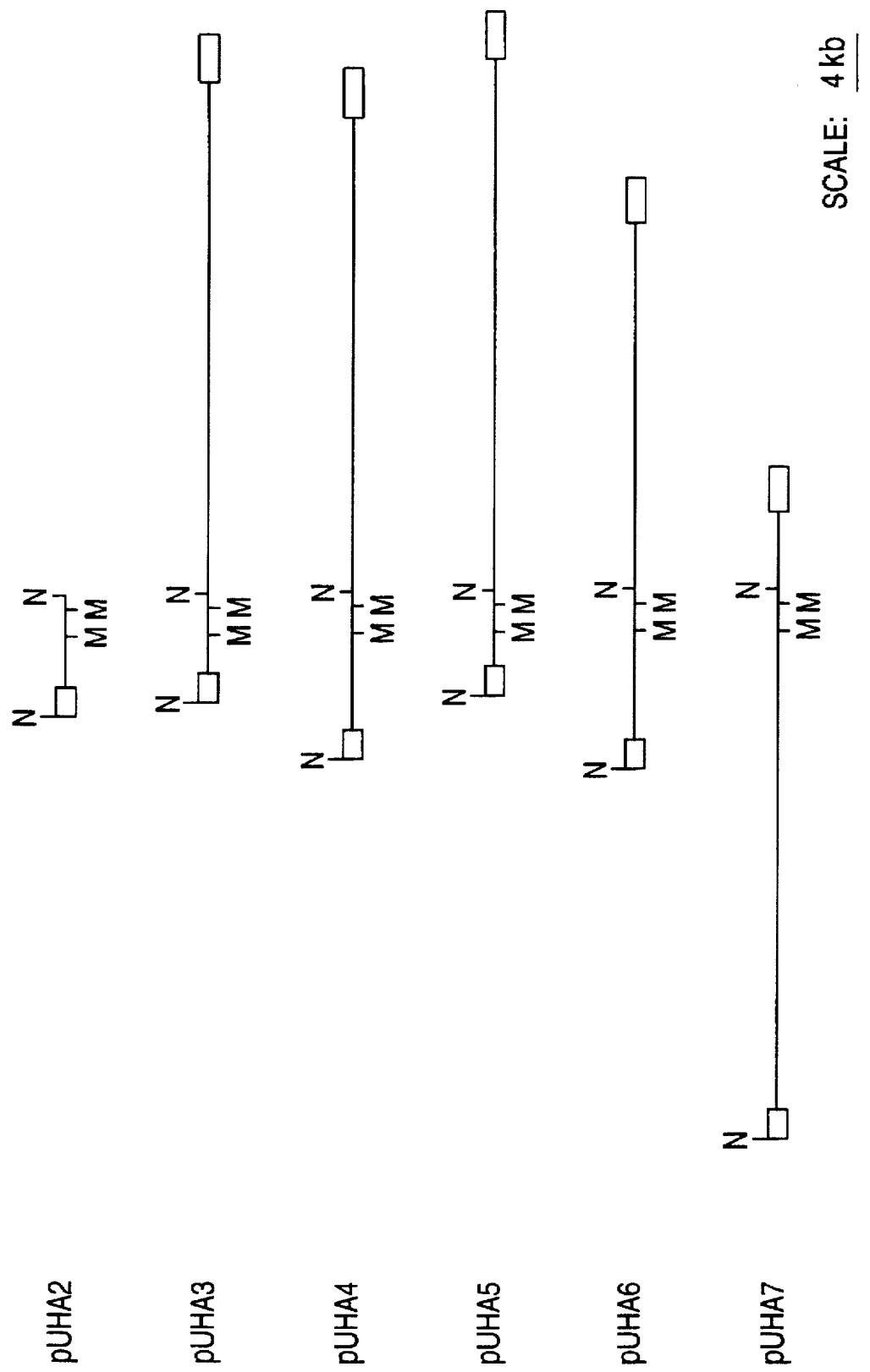
FIG. 2 is a schematic showing the alignment of pUHA2-pUHA7 in linear form for comparison purposes beginning with the NotI site at position 2024 of pYUB178. Cosmids pUHA3-PUHA7 were isolated by colony hybridization using a probe of the 2 kb MluI fragment of PUHA2: M, MluI site; N, NotI site.

FIG. 9-1 and 9-2 (SEQ ID NO:1) and FIG. 9A-1, 9A-2, and 9A-3 (SEQ ID NO:1 and SEQ ID NO:2are comprised of five sheets. FIG. 9-1 and 9-2 shows the nucleotide sequence of the coding strand of the 2745 bp fragment that restores virulence to *M. bovis* ATCC35721. FIG. 9A-1, 9A-2 and 9A-3 shows the same as in FIG. 9-1 and 9-2 together with a 530 amino acid sequence translated from the largest ORF.

FIG. 10A (SEQ ID NO:6 and SEQ ID NO:7) is comprised of two sheets showing the results of a PileUp comparison of known principal sigma factors from *Streptomyces coelicolor* (GenBank Accession Nos. $_x$52980, $_x$52981, $_x$52983) and *Streptomyces griseus* (GenBank Accession No. L08071) with the translation of the largest ORF of the 2000 bp contig from the *M. bovis* virulence restoring factor, rpoV, that restores virulence to *M. bovis* ATCC35721.

FIG. 11 (SEQ ID NO:6 and SEQ ID NO:7) presents the results of a GAP comparison of Streptomyces griseus principal sigma factor (Peptide translation of GenBank accession No. L08071 from nucleotide numbers 570 to 1907, which is the coding sequence of the hrdB gene) with peptide translation of the large ORF of the approximately 3 kb DNA fragment from *M. bovis* associated with virulence.

FIG. 12a-1 and 12a-2 (SEQ ID NO:13 and SEQ ID NO:14) is comprised of two sheets showing the large ORF of the *M. bovis* WAg200 sequence which begins with GTG at position 835–837.

FIG. 12a (SEQ ID NO:8 through SEQ ID NO:12) presents a comparison of putative principal sigma factors of three *M. tuberculosis* complex strains and two Streptomyces sp.

DETAILED DESCRIPTION OF THE INVENTION

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), and CURRENT PROTOCOLS IN IMMUNOLOGY (J. E. Coligan, A. M. Kruisbeek, D. H. Margulies, E. M. Shevach and W. Strober, eds., 1991). All patents, patent applications, and publications mentioned herein, both supra and infra, are incorporated herein by reference.

The present invention provides polynucleotides that are associated with virulence in members of the genus mycobacteria, and particularly in members of the mycobacterial complex. Virulence is the relative capacity of a pathogen to overcome body defenses; it is also the relative ability to cause disease in an infected host. In gram-negative bacterial pathogens, virulence is generally determined by a multiplicity of traits that endow the pathogen with its ability to exploit anatomical weaknesses and overcome the immune defenses of the host. It is expected that a similar multiplicity of traits determines the virulence of pathogenic mycobacteria. Properties associated with virulence in microorganisms include those listed in Table 1.

Table 1. Properties associated with virulence

1. Infectious; capable of being spread from one individual to another.
2. Capable of entering mammalian host cells.
3. Capable of surviving or escaping phagocyte cellular defenses.
4. Capable of multiplying in host cells.
5. Capable of spreading from one infected cell to an uninfected cell.
6. Capable of causing cell injury that results in pathology.

In addition, a virulent organism may be capable of killing the infected host.

By mycobacteria is meant the genus that includes the species *M. phlei, M. smegmatis, M. africanum, M. fortuitum, M. marinum, M. ulcerans, M. tuberculosis, M. bovis, M. microti, M. avium, M. paratuberculosis, M. leprae, M. lepraemurium, M. intracellulare, M. scrofulaceum, M. xenopi, M. genavense, M. kansasii, M. simiae, M. szulgai, M. haemophilum, M. asiaticum, M. malmoense,* and *M. shimoidei.* Of particular interest are the members of the tuberculosis complex, including *M. tuberculosis, M. bovis, M. africanum* and *M. microti.*

As used herein, the term "virulence factor encoding sequence" denotes a polynucleotide sequence that encodes a product that is associated with virulence in a member of the mycobacterial species. This term is encompassed within the term a "sequence associated with virulence" that denotes that a polynucleotide sequence that confers a trait associated with virulence on an avirulent mycobacterium, whether or not the polynucleotide encodes a product. In particular, the virulence associated sequences of the present invention are those that confer one or more traits associated with virulence and have a high degree of homology, i.e., at least about 70% overall homology, preferably at least about 80% overall homology, even more preferably at least about 90% overall homology, to the mycobacterial polynucleotides described herein. Methods of determining homology between sequences are known in the art, and include, for example, direct comparison of sequences, and hybridization assays.

The sequence of one of the mycobacterial DNAs associated with virulence, isolated from *M. bovis,* is shown in FIG. 9. This DNA contains several contigs and an open reading frame (ORF) that based upon amino acid sequence homology in certain regions, encodes a polypeptide that is a putative sigma factor. Portions or all of fragment of which the ORF is part is in plasmids pUHA1, pUHA2, pUHA3, pUHA4, pUHA5, pUHA6, PUHA7, pUHA8, pUHA9, or pUHA11. A particular embodiment of the invention is an isolated or recombinant polynucleotide that is comprised of all or segment of the ORF encoding the sigma factor.

Virulence is also associated with the mycobacterial sequences present in pYUB352, pYUB353, and pYUB354. Thus, the isolated and recombinant polynucleotides may also be comprised of sequences homologous to the mycobacterial DNA in these plasmids.

The DNA sequences upon which the polynucleotides of the invention are based were obtained by the use of in vivo virulence complementation assays. A method for identifying virulence determinants by genetic complementation in vivo was discovered that requires: (i) two strains that are genetically similar; (ii) a phenotype associated with virulence; and (iii) gene transfer systems.

Cosmid genomic libraries of virulent mycobacterial strains of *M. tuberculosis* and *M. bovis* were constructed in an integrating cosmid vector. An example of an integrating cosmid vector is pYUB178, described by Lee et al. (1991), Proc. Natl. Acad. Sci. USA. 88:3111–3115 and Pascopella et al. (1994), Infect. Immun. 62:1313–1319. The integrating vector, approximately 5 kb long, can accommodate 40–45 kb of DNA and uses the site-specific integration system of mycobacteriophage L5 to integrate recombinant DNA into a unique attB site of the mycobacterial chromosome. This vector thus can represent more than 95% of the entire mycobacterial genome in as few as about 300 clones. The recombinant DNA introduced in single copy is stably maintained in mycobacterial cells in the absence of antibiotic selection, even when the strain is passed through animals. Thus, use of this vector reduced the number of clones that needed to be screened, and ensured that cloned genes were not lost during animal passage.

The genomic libraries in the integrating cosmid vector were introduced into corresponding avirulent strains of mycobacteria. Methods of introducing polynucleotides into cells are known in the art, and include, for example, electroporation, transduction and transformation. In order to select for virulent mycobacteria the resulting libraries of recombinant clones were injected into animals, i.e., mice or guinea pigs. It is thought that clones that restore virulence may have a selective advantage and thus be enriched for in the injected animals. In the mouse complementation assay, avirulent mutants cause a self-limiting infection while virulent mycobacterial strains multiply more rapidly, and in high challenge doses cause death. Similarly, in the guinea pig complementation assay, avirulent mutants cause a self-limiting infection. However, virulence in guinea pigs can be assessed by the sites in which gross lesions are found. When avirulent strains of mycobacteria are inoculated subcutaneously in a flank, these strains are not sufficiently virulent to pass through the lymph nodes draining the injection site and enter the systemic circulation in sufficient numbers to cause gross lesions to occur in the spleen. This is contrasted to virulent strains, which under the same inoculation conditions do give rise to spleen (and lung) lesions. Examples of assay systems for comparing avirulent and corresponding virulent mutants of *M. tuberculosis* and *M. bovis* are described in the Examples.

Clones of mycobacteria that had been rendered virulent by the integration of a polynucleotide encoding a virulence factor were isolated. Portions of the integrated virulence determining cosmid were isolated from the clones by restriction enzyme digestion, and the fragments were reinserted into the integrating vector and assayed for virulence factor activity using in vivo complementation assays. These assays led to the identification of mycobacterial DNA encoding polypeptides associated with virulence. In the case of *M. bovis,* the sequence of a fragment of mycobacterial DNA of approximately 3 kb in a clone designated pUHA11 was determined. A comparison of GenBank sequences with the amino acids encoded in the fragment, and particularly within a large ORF and an adjacent contig, showed a significant degree of homology with sigma factors from other microorganisms, indicating that the large ORF encodes a putative sigma factor. On the basis of this homology and the ability of the WAg200 gene to confer a virulence phenotype we have named the gene, rpoV. The high degree of homology between the principal sigma factors of Streptomyces sp. and the putative sigma factors from the *M. tuberculosis* complex may reflect their evolutionary relationship and the fact that both these genera have DNA with a high guanine plus cytosine percentage.

A comparison of the homologous DNA sequences from *M. bovis* WAg200 and the DNA sequence from the attenuated *M. bovis* ATCC35721 indicated that the latter had no sequence differences upstream of the ORF but had two point differences in the coding sequence. One of these differences was also present in the virulent strain *M. tuberculosis* Erdman but the other difference, which caused an arginine to histidine change at position 522, was not found in any of the virulent strains analyzed. Thus we deduce that this is the likely mutation that causes *M. bovis* ATCC35721 to become avirulent. This position is highly conserved among principal sigma factors and their homologues and the region in which it occurs has the characteristics of a helix-turn-helix motif and is believed to be involved in -35 sequence recognition. See Lonetto, M., Gribskov, M. and Gross, C. A., (1992) J. Bact. 174: 3843–3849. Thus, as used herein, the term "similar position to that present in *M. bovis* ATCC35721" in reference to arginine to histidine conversion in a bacterial strain with a mutagenized principal sigma factor contemplates one in a region that is highly conserved among principal sigma factors and their homologues and one that has the characteristics of a helix-turn-helix motif and is believed to be involved in -35 sequence recognition.

While the virulence assays initially were used to isolate the polynucleotides described herein, they may also be used to determine whether polynucleotides constructed from the information and sequences provided herein and factors transcribed and/or translated therefrom are associated with virulence in mycobacteria, and particularly in *M. bovis* or *M. tuberculosis*.

One embodiment of the invention is an isolated polynucleotide comprised of a sequence associated with virulence in mycobacteria. Another embodiment of the invention is an isolated polynucleotide comprised of a sequence associated with avirulence in mycobacteria. As used herein the term "polynucleotide" refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art (e.g., Sambrook, et al.), methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands. Recombinant nucleic acids comprising sequences otherwise not naturally occurring with the designated mycobacterial sequence are also provided by this invention. Although the wild type sequence may be employed, the wild type sequence will often be altered, e.g., by deletion, substitution, or insertion.

The nucleic acid sequences used in this invention will usually comprise at least about 5 codons (15 nucleotides), more usually at least about 7 to 15 codons, and most preferably at least about 35 codons. One or more introns may also be present. This number of nucleotides is usually about the minimal length required for a successful probe that would hybridize specifically with such a sequence.

Techniques for nucleic acid manipulation are described generally, for example, in Sambrook et al., ibid., or Ausubel et al., ibid.. Reagents useful in applying such techniques, such as restriction enzymes and the like, are widely known in the art and commercially available from such vendors as New England BioLabs, Boehringer Mannheim, Amersham, Promega Biotec, U. S. Biochemicals, New England Nuclear, and a number of other sources.

The polynucleotides of the invention will have substantial homology or similarity to the DNAs disclosed herein that are associated with virulence or with avirulence in mycobacteria. A nucleic acid or fragment thereof is "substantially homologous" (or "substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95 to 98% of the nucleotide bases.

Alternatively, a nucleic acid or fragment (or its complementary strand) is substantially homologous (or similar) with a DNA associated with virulence or with avirulence in mycobacteria when they are capable of hybridizing under selective hybridization conditions. Selectivity of hybridization exists when hybridization occurs which is substantially more selective than total lack of specificity. Typically, selective hybridization will occur when there is at least about 65% homology over a stretch of at least about 14 nucleotides, preferably at least about 70%, more preferably at least about 75%, and most preferably at least about 90%. See, Kanehisa (1984) *Nuc. Acids Res.* 12:203–213. The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration (e.g., NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° and preferably in excess of 45°. Stringent salt conditions will ordinarily be less than 1000 mM, typically less than 500 mM, and preferably less than 200 mM. However, the combination of parameters is much more important than the measure of any single parameter. See, e.g., Wetmur and Davidson (1968) *J. Mol. Biol.* 31:349–370.

The polynucleotides of the invention are isolated or substantially purified. An "isolated" or "substantially pure" or "purified" nucleic acid is a nucleic acid, e.g., an RNA, DNA, or a mixed polymer, which is substantially separated from other mycobacterial components that naturally accompany the sequences associated with virulence, e.g., ribosomes, polymerases, and many other mycobacterial polynucleotides such as RNA and other chromosomal sequences. The term embraces a nucleic acid sequence which has been removed from its naturally occurring environment, and includes recombinant or cloned DNA isolates and chemically synthesized analogues or analogues biologically synthesized by heterologous systems.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; and (3) does not occur in nature. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

In some embodiments of the invention the polynucleotides encode a polypeptide associated with virulence or with avirulence. A nucleic acid is said to "encode" a polypeptide if, in its native state or when manipulated by methods well known to those skilled in the art, it can be transcribed and/or translated to produce the polypeptide or a fragment thereof. The anti-sense strand of such a nucleic acid is also said to encode the sequence.

Also contemplated within the invention are expression vectors comprised of a sequence encoding a polypeptide associated with virulence. Expression vectors generally are replicable polynucleotide constructs that encode a polypeptide operably linked to suitable transcriptional and translational regulatory elements. Examples of regulatory elements usually included in expression vectors are promoters, enhancers, ribosomal binding sites, and transcription and translation initiation and termination sequences. These regulatory elements are operably linked to the sequence to be translated. A nucleic acid sequence is operably linked when it is placed into a functional relationship with another nucleic acid sequence. For instance, a promoter is operably linked to a coding sequence if the promoter affects its transcription or expression. Generally, operably linked means that the DNA sequences being linked are contiguous and, where necessary to join two protein coding regions, contiguous and in reading frame. The regulatory elements employed in the expression vectors containing a polynucleotide encoding a virulence factor are functional in the host cell used for expression.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines. The purification of nucleic acids produced by the methods of the present invention are described, e.g., in Sambrook et al. (1989) or Ausubel et al. (1987 and periodic updates).

The polynucleotides of the present invention may also be produced by chemical synthesis, e.g., by the phosphoramidite method described by Beaucage and Carruthers (1981) *Tetra. Letts.* 22:1859–1862 or the triester method according to Matteucci et al. (1981) *J. Am. Chem. Soc.* 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system recognized by the host, including the intended DNA fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals from polypeptides secreted from the host cell of choice may also be included where appropriate, thus allowing the protein to cross and/or lodge in cell membranes, and thus attain its functional topology or be secreted from the cell. Such vectors may be prepared by means of standard recombinant techniques well known in the art and discussed, for example, in Sambrook et al. (1989) or Ausubel et al. (1987).

The selection of an appropriate promoter and other necessary vector sequences will be selected so as to be functional in the host, and may, when appropriate, include those naturally associated with mycobacterial genes. Examples of workable combinations of cell lines and expression vectors are described in Sambrook et al., 1989 or Ausubel et al., 1987); see also, e.g., Metzger et al. 1988), *Nature* 334:31–36. Many useful vectors are known in the art and may be obtained from such vendors as Stratagene. New England Biolabs, Promega Biotech, and others. Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others. Suitable vectors and promoters for use in yeast expression are further described in Hitzeman et al. EP 73,657A. Appropriate nonnative mammalian promoters might include the early and late promoters from SV40 (Fiers et al. (1978) *Nature* 273:113) or promoters derived from murine moloney leukemia virus, mouse mammary tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences see also *Enhancers and Eukaryotic Gene Expression*, Cold Spring Harbor Press, N.Y. (1983).

While such expression vectors may replicate autonomously, they may less preferably replicate by being inserted into the genome of the host cell, by methods well known in the art.

Expression and cloning vectors will likely contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies; or (c) supply critical nutrients not available from complex media, e.g. the gene encoding D-alanine racemase for Bacilli. The choice of the proper selectable marker will depend on the host cell, and appropriate markers for different hosts are well known in the art.

The vectors containing the nucleic acids of interest can be transcribed in vitro and the resulting RNA introduced into the host cell by well known methods (e.g., by injection. See, T. Kubo et al., *FEBS Lett.* 241:119 (1988)), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al. (1989) and Ausubel et al. (1987). The cells into which have been introduced nucleic acids described above are meant to also include the progeny of such cells.

Large quantities of the nucleic acids and polypeptides of the present invention may be prepared by expressing the nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, amphibian or avian species, may also be useful for production of the proteins of the present invention. Propagation of mammalian cells in culture is per se well known. See, *Tissue Culture*, Kruse and Patterson, ed., Academic Press (1973). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. The transformant may be screened or, preferably, selected by any of the means well known in the art, e.g., by resistance to such antibiotics as ampicillin, tetracycline.

Also included within the invention are isolated or recombinant polynucleotides that bind to the regions of the mycobacterial chromosome containing sequences that are associated with virulence, including antisense and triplex forming polynucleotides. As used herein, the term "binding" refers to an interaction or complexation between an oligonucleotide and a target nucleotide sequence, mediated through hydrogen bonding or other molecular forces. The term "binding" more specifically refers to two types of internucleotide binding mediated through base-base hydrogen bonding. The first type of binding is "Watson-Crick-type" binding interactions in which adenine-thymine (or adenine-uracil) and guanine-cytosine base-pairs are formed through hydrogen bonding between the bases. An example of this type of binding is the binding traditionally associated with the DNA double helix and in RNA-DNA hybrids; this type of binding is normally detected by hybridization procedures.

The second type of binding is "triplex binding". In general, triplex binding refers to any type of base-base hydrogen bonding of a third polynucleotide strand with a duplex DNA (or DNA-RNA hybrid) that is already paired in a Watson-Crick manner.

The invention also includes recombinant host cells comprised of any of the above described polynucleotides that contain a sequence associated with virulence in mycobacteria, including those encoding a polypeptide, particularly a polypeptide that is substantially homologous to the polypeptide encoded in FIG. 9, or a fragment thereof, or an analog thereof.

The polynucleotides of the invention may be inserted into the host cell by any means known in the art, including for example, transformation, transduction, and electroporation. As used herein, "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. "Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

The polynucleotides of the invention that are essentially homologous to sequences associated with virulence, shown in FIG. 9, and in plasmids pUHA1, pUHA2, pUHA3, pUHA4, pUHA5, pUHA6, pUHA7, pUHA11 and pUHA16, and in plasmids pYUB352, pYUB353, pYUB354 are of use in the detection of virulent forms of mycobacteria in biological samples. As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

Using the disclosed portions of the isolated polynucleotides associated with virulence as a basis, oligomers of approximately 8 nucleotides or more can be prepared, either by excision from recombinant polynucleotides or synthetically, which hybridize with the mycobacterial sequences in the plasmids and are useful in identification of mycobacteria with the virulence associated trait. The probes for polynucleotides associated with virulence are a length which allows the detection of the virulence associated sequences by hybridization. While 6–8 nucleotides may be a workable length, sequences of 10–12 nucleotides are preferred, and at least about 20 nucleotides appears optimal. These probes can be prepared using routine methods, including automated oligonucleotide synthetic methods. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the virulence encoding polynucleotide. Therefore, usually high stringency conditions are desirable in order to prevent false positives. The stringency of hybridization is determined by a number of factors during hybridization and during the washing procedure, including temperature, ionic strength, length of time, and concentration of formamide. These factors are outlined in, for example, Maniatis, T. (1982).

It may be desirable to use amplification techniques in hybridization assays. Such techniques are known in the art and include, for example, the polymerase chain reaction (PCR) technique described which is by Saiki et al. (1986), by Mullis, U.S. Pat. No. 4,683,195, and by Mullis et al. U.S. Pat. No. 4,683,202.

The probes can be packaged into diagnostic kits. Diagnostic kits include the probe DNA, which may be labeled; alternatively, the probe DNA may be unlabeled and the ingredients for labeling may be included in the kit in separate containers. The kit may also contain other suitably packaged reagents and materials needed for the particular hybridization protocol, for example, standards, as well as instructions for conducting the test.

Polypeptides encoded within the sequences associated with virulence, and fragments and analogs thereof are also included as embodiments of the invention. The polypeptide encoded in the large ORF in FIG. 9 is a putative sigma factor; thus, the intact polypeptide may exhibit the following biological activities: (1) binding to mycobacterial core RNA polymerase, (b) activation of promoter recognition;. and may include (c) DNA melting and (d) inhibition of nonspecific transcription. Methods to determine these biological functions are known in the art, and for example are reviewed in J. D. Helmann and M. J. Chamberlin, Ann. Rev. Biochem. (1988) 57, 839–872. Also included as a biological activity of any specific polypeptide is the binding of the polypeptide to an antibody that is directed to one or more epitopes on that polypeptide. The invention includes polypeptides and analogs or fragments thereof that are essentially homologous to the polypeptide encoded in the large ORF in FIG. 9, and exhibit at least one of the biological activities associated with sigma factor, or alternatively, inhibits at least one of the biological activities associated with sigma factor.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as the modifications known in the art, both naturally occurring and non-naturally occurring.

Ordinarily, the polypeptides of the present invention will be at least about 50% homologous to the polypeptide encoded in the large ORF of FIG. 9, designated herein as "virulence associated sigma factor 1" (also referred to herein as "rpoV"), preferably in excess of about 90%, and, more preferably, at least about 95% homologous. Also included are proteins encoded by DNA which hybridize under high or low stringency conditions, to nucleic acids encoding virulence associated sigma factor 1, as well as closely related polypeptides or proteins retrieved by antisera to virulence associated sigma factor 1.

The length of polypeptide sequences compared for homology will generally be at least about 16 amino acids, usually at least about 20 residues, more usually at least about 24 residues, typically at least about 28 residues, and preferably more than about 35 residues.

The term "substantial homology" or "substantial identity", when referring to polypeptides, indicates that the polypeptide or protein in question exhibits at least about 30% identity with an entire naturally occurring protein or a portion thereof, usually at least about 70% identity, and preferably at least about 95% identity.

Homology, for polypeptides, is typically measured using sequence analysis software. See, e.g., Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, substitutions, and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids.

The terms "isolated," "substantially pure," and "substantially homogenous" are used interchangeably to describe a protein or polypeptide which has been separated from components which naturally accompany it. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes higher resolution can be provided by using HPLC or other means well known in the art.

A protein is considered to be isolated when it is separated from the contaminants which accompany it in its natural state. Thus, a polypeptide which is chemically synthesized or synthesized in a cellular system different from the cell from which it naturally originates will be substantially free from its naturally associated components.

The present invention provides polypeptides which may be purified from mycobacteria as well as from other types of cells transformed with recombinant nucleic acids encoding these proteins. Such protein purification can be accomplished by various methods well known in the art, and include those described, e.g., in *Guide to Protein Purification*, ed. M. Deutscher, vol. 182 of *Methods in Enzymology* (Academic Press, Inc.: San Diego, 1990) and R. Scopes, *Protein Purification: Principles and Practice*, Springer-Verlag: New York, 1982.

If necessary, the amino acid sequence of the proteins of the present invention can be determined by protein sequencing methods well known in the art.

The present invention also provides for polypeptides or fragments thereof which are substantially homologous to the primary structural sequence of the virulence associated sigma factor 1 (also called rpoV). The present invention also embraces in vivo or in vitro chemical and biochemical modifications that incorporate unusual amino acids. Such modifications include, for example, acetylation, carboxylation, phosphorylation, glycosylation, ubiquitination, labelling, e.g., with radionuclides, various enzymatic modifications, as will be readily appreciated by those well skilled in the art. A variety of methods for labelling polypeptides and of substituents or labels useful for such purposes are well known in the art and include radioactive isotopes such as $^{32}$p, ligands, which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labelling polypeptides are well known in the art. See, e.g., *Molecular Cloning: A Laboratory Manual*, 2nd ed., Vol. 1–3, ed. Sambrook, et al., Cold Spring Harbor Laboratory Press (1989) or *Current Protocols in Molecular Biology*, ed. F. Ausubel et al., Greene Publishing and Wiley-Interscience: New York (1987 and periodic updates).

Besides substantially full-length polypeptides, the present invention provides for fragments of the polypeptides capable of binding to antibodies directed to virulence associated sigma factor 1. As used herein, the term fragment or segment, as applied to a polypeptide, will ordinarily be at least about 5 to 7 contiguous amino acids, typically at least about 9 to 13 contiguous amino acids, and most preferably at least about 20 to 30 or more contiguous amino acids.

The present invention also provides for fusion polypeptides comprising the virulence associated sigma factor 1 or fragments thereof. Homologous polypeptides may be fusions between two or more sequences derived from the virulence associated sigma factor 1 or between the sequences of the virulence associated protein and a related protein. Likewise, heterologous fusions may be constructed which would exhibit a combination of properties or activities of the derivative proteins. See, e.g., Godowski et al. (1988) *Science* 241:812–816.

Fusion proteins will typically be made by recombinant nucleic acid methods, but may be chemically synthesized. Techniques for synthesis of polypeptides are described, for example, in Merrifield (1963) *J. Amer. Chem. Soc.* 85:2149–2156.

The polypeptides of the present invention may be used in the preparation of vaccines to treat and/or prevent diseases associated with mycobacterial infections. "Treatment" as used herein refers to prophylaxis and/or therapy.

The polypeptides can be prepared as discrete entities or incorporated into a larger polypeptide, and may find use as described herein. The immunogenicity of the epitopes of the polypeptides of the invention may also be enhanced by preparing them in mammalian or yeast systems fused with or assembled with particle-forming proteins such as, for example, that associated with hepatitis B surface antigen. See, e.g., U.S. Pat. No. 4,722,840. Vaccines may be prepared from one or more immunogenic polypeptides derived from virulence associated polypeptides, and more particularly from virulence associated sigma factor 1.

The preparation of vaccines which contain an immunogenic polypeptide(s) as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylam ine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an rpoV antigenic sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or reenforce the immune response, for example, at 1–4 months for a second dose, and if needed, a subsequent dose(s) after several months. The dosage regimen will also, at least in part, be determined by the need of the individual and be dependent upon the judgment of the practitioner.

In addition, the vaccine containing the immunogenic mycobacterial antigen(s) may be administered in conjunction with other immunoregulatory agents, for example, immune globulins, as well as antibiotics.

The immunogenic virulence associated antigens may be used for the preparation of antibodies. The immunogenic polypeptides prepared as described above are used to produce antibodies, including polyclonal and monoclonal. If polyclonal antibodies are desired, a selected mammal (e.g., mouse, rabbit, goat, horse, etc.) is immunized with an immunogenic polypeptide bearing an rpoV epitope(s). Serum from the immunized animal is collected and treated according to known procedures. If serum containing polyclonal antibodies to an rpoV epitope contains antibodies to other antigens, the polyclonal antibodies can be purified by immunoaffinity chromatography. Techniques for producing and processing polyclonal antisera are known in the art, see for example, Mayer and Walker (1987).

Monoclonal antibodies directed against rpoV epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980); Hammerling et al. (1981); Kennett et al. (1980); see also, U.S. Pat. Nos. 4,341,761; 4,399,121; 4,427,783; 4,444,887; 4,466,917; 4,472,500; 4,491,632; and 4,493,890. Panels of monoclonal antibodies produced against rpoV epitopes can be screened for various properties; i.e., for isotype, epitope affinity, etc.

Antibodies, both monoclonal and polyclonal, which are directed against rpoV epitopes are particularly useful in diagnosis, and those which are neutralizing may be useful in passive immunotherapy. Monoclonal antibodies, in particular, may be used to raise anti-idiotype antibodies. Anti-idiotype antibodies are immunoglobulins which carry an "internal image" of the antigen of the infectious agent against which protection is desired. See, for example, Nisonoff, A., et al. (1981) and Dreesman et al. (1985). Techniques for raising anti-idiotype antibodies are known in the art. See, for example, Grzych (1985), MacNamara et al. (1984), and Uytdehaag et al. (1985). These anti-idiotype antibodies may also be useful for treatment, vaccination and/or diagnosis of mycobacterial infections, as well as for an elucidation of the immunogenic regions of rpoV antigens.

Both the virulence associated polypeptides and antibodies to them are useful in immunoassays to detect presence of antibodies to mycobacteria, or the presence of the virulence associated antigens, and particularly the presence of virulence associated rpoV in biological samples. Design of the immunoassays is subject to a great deal of variation, and many formats are known in the art. The immunoassay will utilize at least one epitope derived from a virulence associated polypeptide, and particularly virulence associated rpoV. In one embodiment, the immunoassay uses a combination of epitopes derived from the virulence associated polypeptide. These epitopes may be derived from the same or from different bacterial polypeptides, and may be in separate recombinant or natural polypeptides, or together in the same recombinant polypeptides. An immunoassay may use, for example, a monoclonal antibody directed towards a virulence associated polypeptide epitope(s), a combination of monoclonal antibodies directed towards epitopes of one mycobacterial antigen, monoclonal antibodies directed towards epitopes of different mycobacterial antigens, polyclonal antibodies directed towards the same antigen, or polyclonal antibodies directed towards different antigens. Protocols may be based, for example, upon competition, or direct reaction, or sandwich type assays. Protocols may also, for example, use solid supports, or may be by immunoprecipitation. Most assays involve the use of labeled antibody or polypeptide; the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Typically, an immunoassay for an antibody(s) to a virulence associated polypeptide, and particularly to virulence associated rpoV will involve selecting and preparing the test sample suspected of containing the antibodies, such as a biological sample, then incubating it with an antigenic (i.e., epitope-containing) virulence associated polypeptide(s) under conditions that allow antigen-antibody complexes to form, and then detecting the formation of such complexes. Suitable incubation conditions are well known in the art. The immunoassay may be, without limitations, in a heterogenous or in a homogeneous format, and of a standard or competitive type.

In a heterogeneous format, the polypeptide is typically bound to a solid support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immulon), diazotized paper, nylon membranes, activated beads, and Protein A beads. For example, Dynatech Immulon[1] or Immulon[2] microtiter plates or 0.25 inch polystyrene beads (Precision Plastic Ball) can be used in the heterogeneous format. The solid support containing the antigenic polypeptide is typically washed after separating it from the test sample, and prior to detection of bound antibodies. Both standard and competitive formats are known in the art.

Complexes formed comprising anti-rpoV antibody (or, in the case of competitive assays, the amount of competing antibody) are detected by any of a number of known techniques, depending on the format. For example, unlabeled anti-virulence associated polypeptide antibodies in the complex may be detected using a conjugate of antixenogeneic Ig complexed with a label, (e.g., an enzyme label).

In immunoassays where the virulence associated polypeptides are the analyte, the test sample, typically a biological sample, is incubated with antibodies directed against the virulence associated polypeptide under conditions that allow the formation of antigen-antibody complexes. It may be desirable to treat the biological sample to release putative bacterial components prior to testing. Various formats can be employed. For example, a "sandwich assay" may be employed, where antibody bound to a solid support is incubated with the test sample; washed; incubated with a second, labeled antibody to the analyte, and the support is washed again. Analyte is detected by determining if the second antibody is bound to the support. In a competitive format, which can be either heterogeneous or homogeneous, a test sample is usually incubated with antibody and a labeled, competing antigen is also incubated, either sequentially or simultaneously. These and other formats are well known in the art.

Also included as an embodiment of the invention is an immunoassay kit comprised of one or more polypeptides of the invention, or antibodies to a polypeptide associated with virulence, and a buffer, packaged in suitable containers.

In addition, compounds which block the activity of virulence factor associated polypeptides and particularly virulence associated rpoV, may be prepared utilizing the sequence information of provided herein. This is performed by overexpressing the polypeptide, purifying the polypeptide, and then performing X-ray crystallography on the purified virulence associated polypeptide to obtain its molecular structure. Next, compounds are created which have similar molecular structures to all or portions of the polypeptide or its substrate. The compounds are then combined with the polypeptide and attached thereto so as to block one or more of its biological activities.

The polynucleotides of the invention may also be used to produce or improve live attenuated or killed tuberculosis vaccines. For example a vaccine strain may be produced by mutating a virulence associated polynucleotide, and particularly one encoding virulence associated sigma factor 1. The mutated strain may then be formulated into a vaccine and administered to treat mycobacterial infections. In addition, virulence associated polynucleotides may be added to BCG vaccine strains to provide attenuated mutant tuberculosis vaccines.

The invention also encompasses a new approach for determining factors associated with virulence or other properties of interest in other genera of bacteria by showing that an arginine to histidine change near the C-terminal end of a principal sigma factor, and in particular at the equivalent site to that which occurs in *M. bovis* AtCC35721, is not lethal but causes an alteration in the specificity of promotion of the sigma factor. Such a change could be engineered in the principal sigma factor in species of other genera of bacteria using techniques known in the art, including for example, site directed mutagenesis and homologous recombination. Identification and subsequent investigation of the genes whose promotion is altered by such a change could be performed using techniques known to one of skill in the art, for example, comparative protein electrophoresis, partial protein sequencing and reverse genetic methods. One might also use, for example, in vivo methods for identifying the level of promotion of different promoters in the presence of normal and altered sigma factors. The results of these studies should reveal genes whose promotion changes significantly when promoted by an altered principal sigma factor. Such genes may be potential targets for new drugs or they could be targets for inactivation to generate new strains for use in vaccines or strains with other desirable properties.

The following examples are provided only for illustrative purposes, and not to limit the scope of the present invention. In light of the present disclosure numerous embodiments within the scope of the claims will be apparent to those of ordinary skill in the art.

EXAMPLE 1
ISOLATION OF A VIRULENCE FACTOR OF MYCOBACTERIA USING A GUINEA PIG COMPLEMENTATION ASSAY

Virulent tuberculosis complex strains were cultured as described previously (Collins and de Lisle 1984). Mycobacterial species were identified by standard methods.

For preparation of genomic DNA, tuberculosis complex strains were grown on standard mycobacterial media, harvested into buffer and inactivated by heating.

Genomic DNA was prepared form the organisms and partially digested with a range of concentrations of Sau3AI. Fragments of 30–50 kb from these digestions were prepared using sucrose gradient centrifugation and ligated to BclI-digested pYUB178 DNA that had been treated with calf intestinal phosphatase. The ligation mixture was in vitro-packaged into γ phage heads and transduced into *Escherichia Coli*. The kanamycin resistant recombinant clones were pooled and cosmid DNA was prepared using standard plasmid isolation methods. The variability of members of the library was established.

A tuberculosis complex strain of lowered virulence for guinea pigs (referred to subsequently as avirulent) was cultured in roller bottles and organisms were prepared and electroporated with a library of pYUB178::virulent-tuberculosis-complex-DNA. The electroporated organisms were plated onto media containing kanamycin and kanamycin resistant clones were pooled to form a library. Each member of this library had the chromosome of the avirulent tuberculosis organism into which a cosmid with an insert of genomic DNA from a virulent tuberculosis complex strain was integrated. The library was cultured in liquid media and aliquots were inoculated into guinea pigs. Separate guinea pigs were also inoculated with the matching avirulent tuberculosis complex strain as a control. The most clear cut distinction between virulent and avirulent strains was in the presence or absence of gross lesions in the spleen.

The method for virulence testing in guinea pigs was adapted from the procedures described in the Trudeau Mycobacterial Culture Collection catalogue, (Anon, 1972). Albino, outbred guinea pigs were inoculated subcutaneously in the flank. Libraries and individual strains of mycobacteria were inoculated into at least three guinea pigs which were kept in filtered-air, ventilated animal cages. Animals were sacrificed approximately 6 and 13 weeks after inoculation and examined for the presence of gross lesions of tuberculosis. Samples from the injection site, the prefemoral lymph nodes and spleen were cultured for mycobacteria using previously described methods. Formalin-fixed tissues, from the spleen, liver, kidney and lung were embedded in paraffin, sectioned at 3–5 μm, and stained with either hematoxylin and eosin (HE) or by the Ziehl-Neelsen method.

A. Virulent Tuberculosis Strain Used to Make Cosmid Library

A virulent *M. bovis* strain was isolated from bovine tissue submitted to the Wallaceville Animal Research Centre, Upper Hutt, New Zealand. The strain, isolated from bovine tissue with the accession number 89/5276, was designated WAg200 and was cultured as described previously (Collins and de Lisle 1984). The strain was also shown to be virulent for guinea pigs. Bacteriological identification of the strain as *M. bovis* was based on colony morphology, slow growth, acid-fast staining, susceptibility to thiophene-2-carboxylic acid hydrazide and isoniazid, and growth on pyruvate-supplemented but not glycerol-supplemented media. The strain was also characterized by restriction fragment analysis (Collins et al. 1993). In infected animal experiments described below, bacteriological identification of reisolated M. bovis strains was based on colony morphology, slow growth and growth on pyruvate-supplemented media.

B. DNA Preparation

*M. bovis* WAg200 was cultured under biosafety containment at 37° C. on 40×85 mm petri dishes of 7H11 Middlebrook (Difco) media containing oleic acid, albumin, dextrose, serum, lysed red blood cells, 0.05% polyoxyethylene sorbitan monooleate (Tween-80) and pyruvate (Gallagher and Horwill 1977). The organisms were harvested into 7 Falcon tubes each containing 50 ml phosphate buffered saline (0.14M NaCl, 4 mM KCl, 8 mM $Na_2HPO_4$, 2 mM $KH_2PO_4$; pH 6.5) and inactivated by heating at 75° C. for 35 min. After centrifugation, the yield in each tube was 1–1.5 g wet weight organisms. Genomic DNA was prepared from the organisms using a scaled up version of the method described by van Soolingen et al. (1991). The total yield of DNA after extraction of all organisms was 300 μg in 1 ml.

C. *E. coli* cosmid library of *M. bovis* WAg200 *M. bovis* WAg200 DNA was partially digested with a range of concentrations of Sau3AI and digestions having the largest yield of 30–50 kb fragments were selected after analytical electrophoresis on 0.4% agarose gels (Jacobs et al. 1991). Fragments of 30–50 kb from these digestions were prepared using sucrose gradient centrifugation (Weis 1991) and ligated to BclI-digested pYUB178 DNA that had been treated with calf intestinal phosphatase. The final genomic DNA concentration in the 10 μl ligation mixture was 200 ng/μl and the DNA molar ratio of insert to vector was 1:20. Four μl of the ligation mixture was in vitro-packaged with the GigaPack II Gold Packaging Extract (Stratagene, La Jolla, Calif.) according to the manufacturer's procedure. The in vitro-packaged lysate was transduced, using previously described methods (Jacobs et al. 1991), into *E. coli*. The kanamycin resistant recombinant clones were pooled and inoculated into LB broth containing 25 μg/ml kanamycin. Cosmid DNA was prepared using standard plasmid isolation methods of alkaline lysis and cesium chloride gradient centrifugation (Sambrook et al. 1989). Aliquots of the library were stored frozen at −70° C. and cosmid DNA preparations were stored at −20° C.

The total number of recombinant *E. coli* clones produced was approximately 20,000. These clones were pooled and the library of pYUB178::*M. bovis* WAg200 cosmids was amplified as a plasmid preparation. This preparation was performed by culturing the pooled clones in 750 ml LB media containing 25 μg/ml kanamycin. Both before and after the plasmid amplification of the library, cosmids from 20 randomly selected clones were shown to have different restriction patterns.

Plasmids and *M. bovis* strains used in this study are listed in Tables 1 and 2.

TABLE 1

*M. bovis* strains used in this study

| *M. bovis* strain or clone | Description | Source |
|---|---|---|
| ATCC35721 | Low virulence strain | ATCC |
| WAg200 | Virulent strain isolated in N.Z. | G. de Lisle |
| WAg300 | ATCC35721 containing pUHA1 | This study |
| WAg301 | ATCC35721 containing pUHA3 | This study |
| WAg302 | ATCC35721 containing pUHA4 | This study |
| WAg303 | ATCC35721 containing pUHA5 (Junction Fragment Pattern 1) | This study |
| WAg304 | ATCC35721 containing pUHA5 (Junction Fragment Pattern 2) | This study |
| WAg305 | ATCC35721 containing pUHA5 (Junction Fragment Pattern 3) | This study |
| WAg306 | ATCC35721 containing pUHA6 (Junction Fragment Pattern 1) | This study |
| WAg307 | ATCC35721 containing pUHA6 (Junction Fragment Pattern 2) | This study |
| WAg308 | ATCC35721 containing pUHA6 (Junction Fragment Pattern 3) | This study |
| WAg309 | ATCC35721 containing pUHA7 (Junction Fragment Pattern 1) | This study |
| WAg310 | ATCC35721 containing pUHA7 (Junction Fragment Pattern 2) | This study |
| WAg311 | ATCC35721 containing pUHA7 (Junction Fragment Pattern 3) | This study |
| WAg320 | ATCC35721 containing 3 kb fragment of WAg200 that restores virulence | This study |

TABLE 2

Plasmids used in this study

| Plasmid | Description | Source |
|---|---|---|
| pYUB178 | Integrating cosmid shuttle vector | W. Jacobs |
| pUHA1 | pYUB178::WAg200 cosmid which restores virulence to ATCC35721 | This study |
| pUHA2 | pYUB178 containing 6 kb of pUHA1 insert | This study |
| pUHA3 | pYUB178::WAg200 cosmid overlapping pUHA2 | This study |
| pUHA4 | pYUB178::WAg200 cosmid overlapping pUHA2 | This study |
| pUHA5 | pYUB178::WAg200 cosmid overlapping pUHA2 | This study |
| pUHA6 | pYUB178::WAg200 cosmid overlapping pUHA2 | This study |
| pUHA7 | pYUB178::WAg200 cosmid overlapping pUHA2 | This study |
| pUHA8 | pYUB178 with PacI sites on both sides of the BclI cloning site | This study |
| pUHA9 | pBluescript II KS(+) with PacI sites on both sides of the BclI site | This study |
| pUHA11 | pUHA9 containing 3 kb fragment from WAg320 | This study |
| pUHA16 | pUHA11 with 3 kb fragment in reverse orientation | This study |

D. Transformation of cosmid library into avirulent *M. bovis*

The receptor strain used was *M. bovis* ATCC35721 which had lowered virulence for guinea pigs. For simplicity this strain is subsequently referred to as avirulent. It was inoculated into 2×100 ml Middlebrook 7H9 broth (Difco) containing albumin, glucose, glycerol and Tween-80 as described (Jacobs et al. 1991). The cultures were grown in roller bottles at 1 revolution/min to an O.D. at 600 nm of 0.18. The organisms were washed and concentrated to a volume of 1 ml in cold 10% glycerol and 0.4 ml were electroporated with 4 μl of pYUB178::*M. bovis* WAg200 cosmid library DNA (1 μg/pl) as described by Jacobs et al. (1991). After electroporation, the organisms were cultured at 37° C. on the same media used for DNA preparation but without the addition of oleic acid, serum or lysed red blood cells and with the addition of 1% sodium pyruvate and 10

μg/ml kanamycin. Approximately 4000 clones of M. bovis ATCC35721 (pYUB178:: M. bovis WAg200) were obtained and pooled. A control electroporation of 400 μl organisms without added plasmid DNA yielded no kanamycin resistant colonies. Fifteen M. bovis ATCC35721 (pYUB178::M. bovis WAg200) clones were selected before pooling and subcultured for DNA preparation in 3–5 ml of the same media used for culturing M. bovis ATCC35721. Genomic DNA of recombinants, extracted by the method of van Soolingen et al. (1991), was characterized by restriction fragment digestion with PstI, electrophoresis, Southern blotting and hybridization with a probe of pYUB178. This revealed the junction fragments of the integrated cosmid and is referred to below as junction fragment analysis. In all cases the fragment patterns were different.

E. Protocol to assess virulence of tuberculosis complex strains

The method for virulence testing in guinea pigs was adapted from the procedures described in the Trudeau Mycobacterial Culture Collection catalogue, (Anon, 1972). Albino, outbred guinea pigs were inoculated subcutaneously in the flank. Libraries and individual strains of mycobacteria were inoculated into guinea pigs which were kept in filtered-air, ventilated animal cages. Animals were sacrificed approximately 6 and 13 weeks after inoculation and examined for the presence of gross lesions of tuberculosis. Samples from the injection site, the prefemoral lymph nodes and spleen were cultured for mycobacteria using previously described methods (Collins and de Lisle 1984). Formalin-fixed tissues, from the spleen, liver, kidney and lung were embedded in paraffin, sectioned at 3–5 μm, and stained with either hematoxylin and eosin (HE) or by the Ziehl-Neelsen method.

i. First inoculation experiments in guinea pigs

The level of virulence in guinea pigs of M. bovis ATCC35721 was assessed by the sites in which gross lesions were found (Table 3). There were no such lesions in the spleen. This indicated that M. bovis ATCC35721 was not sufficiently virulent to pass through the lymph nodes draining the injection site and enter the systemic circulation in sufficient numbers to cause gross lesions to occur in the spleen.

TABLE 3

Gross lesions in animals sacrificed 92 days after infection with a 0.2 ml inoculum of M. bovis ATCC35721 containing 1.9 × 10⁷ colony forming units (CFU).

| Guinea pig | Injection site | Prefemoral lymph nodes | Spleen |
| --- | --- | --- | --- |
| A | + | + | − |
| B | + | + | − |
| C | + | + | − |

In a subsequent experiment, the virulence of the M. bovis ATCC35721(pYUB178::M. bovis WAg200) library was assessed at two time intervals and gross lesions were identified as shown in Tables 4 and 5.

TABLE 4

Gross lesions in animals sacrificed 50 days after infection with a 0.2 ml inoculum of M. bovis ATCC35721 (pYUB178::M. bovis WAg200) library containing approximately 10⁶ CFU.

| Guinea pig | Injection site | Prefemoral lymph nodes | Spleen |
| --- | --- | --- | --- |
| A | +/− | + | − |
| B | + | + | − |
| C | + | + | + |

TABLE 5

Gross lesions in animals sacrificed 89 days after infection with a 0.2 ml of inoculum of M. bovis ATCC35721 (pYUB178::M. bovis WAg200) library containing approximately 10⁶ CFU.

| Guinea pig | Injection site | Prefemoral lymph nodes | Spleen |
| --- | --- | --- | --- |
| A | + | + | + |
| B | + | + | + |
| C | + | + | + | ii. Characterization of recombinant M. bovis from guinea pigs

Prefemoral lymph node and spleen tissues of all guinea pigs were cultured for the presence of M. bovis. Apart from spleen tissue from guinea pig A in the 50 day group, M. bovis organisms were isolated from all these tissues. Over 160 individual clones representing all lesion-containing prefemoral lymph nodes and spleens were subcultured and their genomic DNA subjected to junction fragment analysis. Approximately 80% of all clones had the same junction fragment pattern. Clones which gave this pattern were found in all M. bovis containing tissues. One of these ATCC35721 (pYUB178::M. bovis WAg200) clones containing the predominant junction fragment pattern designated as WAg300 was used for further experiments below.

iii. Second inoculation experiment in guinea pigs

In this experiment the virulence of M. bovis WAg300 and M. bovis ATCC35721 were compared concurrently. Results are given in Tables 6 and 7.

TABLE 6

Gross lesions in animals sacrificed 45 days after infection with a 0.2 ml inoculum of M. bovis ATCC35721 containing 7.6 × 10⁵ CFU.

| Guinea pig | Injection site | Prefemoral lymph nodes | Spleen |
| --- | --- | --- | --- |
| A | + | + | − |
| B | + | + | − |
| C | + | + | − |

TABLE 7

Gross lesions in animals sacrificed 45 days after infection with a 0.2 ml inoculum of *M. bovis* WAg300 containing $2.8 \times 10^5$ CFU.

| Guinea pig | Injection site | Prefemoral lymph nodes | Spleen |
| --- | --- | --- | --- |
| A | + | + | + |
| B | + | + | + |
| C | + | + | + |

*M. bovis* strains isolated from these animals were shown to be identical to *M. bovis* WAg300 by junction fragment analysis.

The difference between the two sets of guinea pigs with respect to the presence or absence of spleen lesions clearly indicated that *M. bovis* WAg300 was more virulent than *M. bovis* ATCC35721.

F. Isolation of part of the integrated virulence determining cosmid

Genomic DNA was prepared from *M. bovis* WAg300, digested with the restriction enzyme NotI and ligated under conditions favoring self ligation. The ligation mixture was electroporated into *E. coli*, and kanamycin resistant clones were isolated. A plasmid isolated from one of these clones was denoted pHUA2. This plasmid contained the pYUB178 kanamycin resistance gene and *E. coli* origin of replication from the integrated cosmid in *M. bovis* WAg300 as well as approximately 6 kb of cosmid insert DNA. The relationship between pUHA2 and the original cosmid, designated pUHA1, which was integrated in *M. bovis* WAg300 and which was never isolated in total is shown in FIG. 1.

G. Selection of cosmids with possible virulence determining factors

A 2 kb MluI fragment from the insert of pUHA2 was used as a colony hybridization probe of the *E. coli* pYUB178:: *M. bovis* WAg200 library. Approximately one colony in every 130 library colonies gave a positive hybridization signal. Cosmids were isolated from 48 hybridizing clones using standard plasmid preparation methods and compared to each other and to pUHA2 on the basis of restriction enzyme digestion patterns. Three cosmids, designated pUHA3, pUHA4 and pUHA5, had most similarity to pUHA2 and are shown in FIG. 2. Two other cosmids with inserts which overlapped those of pUHA3–pUHA5 were also selected from the remaining 45 cosmids by using pUHA2 as a probe of Southern blots of cosmid restriction digests. These cosmids, designated pUHA6 and pUHA7 are also shown in FIG. 2.

H. Preparation of putative virulence sequences for guinea pig reinoculation

Cosmids pUHA3-pUHA7 were electroporated into *M. bovis* ATCC35721 and clones of *M. bovis* ATCC35721 (pUHA3-pUHA7) were recovered using kanamycin selection. These recombinant *M. bovis* clones, designated WAg301-WAg311 were inoculated into guinea pigs to assess their virulence. The number of *M. bovis* clones inoculated was greater than the number of cosmids because in some cases, junction fragment analysis of individual clones revealed three different patterns were obtained for some cosmids. In cases where more than one pattern was obtained for DNA isolated from clones containing a particular cosmid, subcultures of clones representing each pattern were combined for inoculation. The association between cosmids and *M. bovis* recombinants is shown in Table 1. Guinea pigs that had received *M. bovis* recombinants containing cosmids pUHA3, pUHA4, pUHA5, and pUHA7 developed extensive lung or spleen lesions, indicating that these cosmids had restored the virulence to the *M. bovis* ATCC35721 strain. These three cosmids contain genomic inserts of approximately 40–43 kb and have a common overlapping segment of approximately 10 kb.

Cosmid pUHA3 was partially digested by Sau3AI and in separate experiments 2–4 kb and 10–15 kb fragments were cloned into the cosmid shuttle vector pUHA8. Vector pUHA8 was produced from pYUB178 by incorporating PacI sites on either side of the BclI cloning site. These libraries of pUHA3 were electroporated into *M. bovis* ATCC35721 to produced libraries of *M. bovis* ATCC35721 (pUHA8::pUHA3). Approximately 300 colonies from the 2–4 kb library and 1000 colonies from the 10–15 kb library were pooled separately, subcultured and inoculated into guinea pigs.

Guinea pigs that had received *M. bovis* recombinants containing either the 2–4 kb fragments or the 10–15 kb fragments, developed extensive spleen lesions indicating that these fragments had restored virulence to the *M. bovis* ATCC35721 strain. *M. bovis* organisms were isolated from the spleen lesions and subcultured for DNA extraction. DNA prepared from these cultures was digested with PacI and electrophoresed on agarose gels. No restriction fragments could be clearly visualized by staining with ethidium bromide so the gels were Southern blotted onto nylon and hybridized with a DNA probe of the entire insert of pUHA2. This probe revealed two hybridized bands for many of these isolates. One of the bands was the same for all isolates and corresponded to the position on the blot of undigested genomic DNA. The other band varied in size from one isolate to another but in no case was smaller than approximately 3 kb. One strain containing an approximately 3 kb fragment was designated WAg320 and used for further analysis. These results showed that a DNA fragment of approximately 3 kb was sufficient to restore virulence to *M. bovis* ATCC35721. This 3 kb sequence has sufficient overlap with the insert of pUHA2 for detectable hybridization to occur between them. This alignment of the 3 kb sequence and pUHA2 is also consistent with the virulence restoring abilities of cosmids puHA4, pUHA5 and pUHA7 since most of the insert of pUHA2 is within the shared DNA segment of cosmids pUHA4, pUHA5, and pUHA7.

I. Restriction mapping of pUHA3 cosmid

A restriction map of cosmid pUHA3 (FIG. 3) was constructed for the enzymes MluI, NheI and NotI using a partial digestion technique. The cosmid insert contained no sites for the enzyme XbaI, whereas the pYUB178 vector contained two sites as shown (FIG. 3). In the technique used, cosmid pUHA3 was partially digested with each of the three enzymes separately and then the partial digests were digested with XbaI. DNA fragments in each partial digest were separated in duplicate by agarose electrophoresis and transferred to nylon filters by Southern blotting. One of the duplicates was hybridized with a $^{32}p$ labelled probe of the left hand vector arm of pUHA3 and the other duplicate was hybridized with a probe of the right hand vector arm of pUHA3. Best estimates of the molecular size differences between the labelled fragments were obtained by comparison to labelled DNA markers and these were also compared to fragment sizes of complete digests of pUHA3 with the same enzyme.

J. Sequencing of 3 kb sequence

WAg320 was digested with PacI and the 3 kb fragment was ligated into the PacI site of the sequencing vector pUHA9 using standard methods. The "Erase-a-base" system (Promega) was used to make progressive, unidirectional deletion mutants of two clones designated pUHA11 and pUHA16 which contained the 3 kb fragment in opposite orientations. Appropriately sized deletion mutants were cloned and chosen as instructed by the manufacturer's protocols. Polymerase chain reaction sequencing was performed by using commercial kits (Gibco-BRL and Intermed) in accordance with the manufacturer's instructions. The 2745 bp fragment that restores virulence to *M. bovis* ATCC35721 is shown in FIG. 9. FIG. 9A shows this sequence together with a 530 amino acid translation of the largest ORF. The first codon of this ORF at positions 835–837 is contiguous with the likely ribosome binding site so initiation may actually occur at codon three at positions 841–843.

K. Comparison of the 3 kb Mycobacterial DNA sequence with GenBank sequences

The DNA sequence obtained from the 3 kb fragment that restores virulence to *M. bovis* ATCC35721, shown in FIG. 9, was analyzed using the 7.3.1-UNIX update (September 1993) of the program package supplied by the University of Wisconsin Genetics Computer Group (575 Science Drive, Madison, Wis. 53711); this package is abbreviated as "GCG". An earlier version of the package is described in Devereux, J., et al., (1984), Nucl. Acids Res. 12: 387–395.

The comparison was performed as follows. The DNA sequences of the contigs were translated into amino acids (using the program TRANSLATE) and compared to the GenBank database update 82.0 using the programme TFASTA. This comparison revealed that the sequence analyzed had significant homology with numerous sigma factors. Some of the DNA sequences of the sigma factors with which the homology was particularly high were obtained from the GenBank database using the programme FETCH and their coding sequences were translated into amino acids using TRANSLATE. These sigma factors were then compared to an amino acid translation (using TRANSLATE) of the large ORF on the largest contig using the programme PILEUP. A smaller downstream contig was also translated using TRANSLATE and compared in the same PILEUP comparison. FETCH, PILEUP, TFASTA and TRANSLATE are programmes in the GCG package.

The results of a PileUp comparison of hrdB principal sigma factors from *Streptomyces coelicolor* (GenBank Accession No. X52983) and *Streptomyces griseus* (GenBank accession No. L08071) with the amino acid translation of the ORF from the *M. bovis* virulence restoring factor is shown in FIG. 10-A. It can be seen from the results that there is a high degree of relatedness between all three sequences, particularly in the region above 290.

FIG. 11 presents the results of a GAP comparison of *Streptomyces griseus* principal sigma factor (Peptide translation of GenBank accession No. L08071 from nucleotide numbers 570 to 1907, which is the coding sequence of the hrdB gene) with peptide translation of the large ORF of the approximately 3 kb DNA fragment from *M. bovis* associated with virulence. Exact homology between the sequences is indicated by vertical dashes.

While there were significant homologies of the sequences encoded in the *M. bovis* fragment with the sigma factor sequences indicated above, the overall homology detected was less than about 65% to 70% with any specific sequence. In addition, there was no exact match with any of the GenBank sequences.

L. Identification of a Mutation Associated with Avirulence

The 2.7 kb fragment from *M. bovis* WAg200 was sequenced on both chains using an ordered deletion mutant strategy and polymerase chain reaction sequencing with [33]P. A probe of this fragment was used to select hybridizing clones from replica plates of genomic libraries of *M. bovis* ATCC35721, *M. bovis* WAg201 (another virulent New Zealand strain), and *M. tuberculosis* Erdman. The homologous DNA fragments were isolated and sequenced and their large ORFs translated for the PILEUP comparison.

The sequence of the 2.7 kb fragment encoding the rpoV gene from *M. bovis* WAg200 and comparison of its translation with those of other *M. bovis* and *M. tuberculosis* rpoV genes and principal sigma factors from two Streptomyces species is shown in FIG. 12. FIG. 12a presents the sequence of *M. bovis* WAg200 showing the large ORF which begins with GTG at position 835–837. Since the potential ribosome binding sites (underlined) are so close or overlap this codon, the likely initiation site is the third codon of the ORF, as indicated. The three mutations in *M. bovis* ATCC35721 and their effect on the translation of rpoV are shown respectively above and below the equivalent sequences from *M. bovis* WAg200. Two of the three mutations are also found in one or more of the other *M. tuberculosis* complex strains analyzed (strain numbers in brackets).

FIG. 12b presents a comparison of putative principal sigma factors of four *M. tuberculosis* complex strains and two Streptomyces sp. Upper case letters denote amino acids that agree with the consensus sequence of the *M. tuberculosis* complex. An arrow denotes the position of the amino acid in the *M. bovis* ATCC35721 sequence that differs from that of all three of the other *M. tuberculosis* complex strains. These results indicate that it is this difference that causes *M. bovis* ATCC35721 to become avirulent. This position is highly conserved among principal sigma factors and their homologues and the region in which it occurs has the characteristics of a helix-turn-helix motif and is believed to be involved in -35 sequence recognition. (Lonetto, M. et al. (1992), J. Bact. 174:3843–3849). Mutation of an arginine to a histidine in this region has previously been shown to cause an alteration in promoter recognition in *Eschicherichia coli* (Gardella, T., et al. (1989), *J. Mol. Biol.* 206:579–590). But mutation at the equivalent position in the *M. bovis* ATCC 35721 sequence has not been reported.

EXAMPLE 2
POLYNUCLEOTIDES ENCODING VIRULENCE FACTORS ISOLATED BY A MOUSE COMPLEMENTATION ASSAY

A method for identifying virulence determinants by genetic complementation was discovered that requires: (i) two strains that are genetically similar; (ii) a phenotype associated with virulence; and (iii) gene transfer systems. An existing pair of *M. tuberculosis* strains, H37Rv (virulent) and H37Ra (avirulent), distinguishable by their ability to cause disease in animal models were used. H37Ra and H37Rv were derived from the same clinical isolate in 1934 and pulsed field gel analyses of DNA fragments generated by digestion with infrequently cutting enzymes revealed that their macroscopic genome organization was similar. The well-characterized difference in growth rates in mouse lungs and spleens of H37Ra and H37Rv correlated with their pathogenicity. The ability of H37Ra/H37Rv recombinants to grow faster than H37Ra in the mouse was defined as a potential virulence phenotype.

A genomic library of *M. tuberculosis* H37Rv was constructed in an integrating cosmid vector, pYUB178, and electroporated into H37Ra. Mice were infected with pools of H37Ra recombinants containing H37Rv DNA to allow the selection of growing clones in mouse spleen and lung. The integrating shuttle cosmid libraries, based on the mycobacteriophage L5 integration system, were ideal for in vivo complementation because: (i) only approximately 225 clones were required to represent the H37Rv genome, (ii) toxic effects associated with the expression of genes from multicopy plasmids were avoided, (iii) kanamycin selection pressure was not necessary to maintain the cosmid, and (iv) clusters of contiguous genes can be delivered and expressed.

The growth rates of selected recombinants were measured in mouse spleen and lung, and a method was developed to retrieve the H37Rv insert DNA from the chromosome of a recombinant. This method allowed for the identification and characterization of a 25 kb DNA fragment of *M. tuberculosis* which conferred an in vivo growth advantage to the growth-defective H37Ra.

A. Bacterial strains and growth conditions

*M. tuberculosis* strains H37Ra and H37Rv were provided by Wilbur Jones of the Centers for Disease Control, Atlanta, and were grown in enriched 7H9 broth [Middlebrook 7H9 medium enriched with albumin-dextrose complex (ADC) or oleic acid-albumin-dextrose complex (OADC) (Difco Laboratories, Detroit, Mich.) and a 0.05% polyoxyethylene sorbitan monooleate (Tween-80®)], under Biosafety Level 3 (BSL3) containment. All cultures were grown at 37° C. *E. coli* strains $_{\chi}$2764 (13), HB101 (4)and DH5α (Bethesda Research Laboratories Life Technologies Inc., Gaithersburg, Md.) were grown in L broth. Strain $_{\chi}$2764 was grown at 30° C. See Table 8 for a list of strains and plasmids.

B. Construction of shuttle cosmid and H37Rv library

The pYUB178 integrating shuttle cosmid (FIG. 1A), was constructed by ligating the 975 bp cos-containing BglII/BclI fragment of lambda DNA to the BclI-digested, calf-intestine alkaline phosphatase (CIP)treated (Boehringer Mannheim Biochemicals, Indianapolis, Ind.) pMV305.F (18, 27) under conditions which favored the formation of linear concatemers, i.e. greater than 50 ng/μl final DNA concentration.

Genomic DNA of H37Rv was prepared by mechanical disruption of bacterial cells and subsequent phenol-chloroform extractions as previously described (12). H37Rv genomic DNA was partially digested with a range of concentrations of Sau3AI to generate 30–50 kb-sized fragments. Fragments of 30–50 kb were isolated as previously described (14). The 30–50 kb Sau3AI fragments of chromosomal DNA were then ligated to CIP-treated, BclI-digested pYUB178 DNA; the final DNA concentration was 50–100 ng/μl and the DNA molar ratio of insert to vector was 1.

C. Library packaging into lambda phage heads and tails

Four μl of a ten μl ligation mixture was in vitro-packaged with the GigaPack II Packaging Extract (Stratagene, La Jolla, Calif.) according to the manufacturer's procedure. The in vitro-packaged lysate was transduced, using previously described methods (14), into the in vivo packaging strain of *E. coli* $_{\chi}$2764 (13).

D. In vivo-packaging

The $10^3$–$10^4$ kanamycin-resistant recombinant clones were pooled and inoculated into L broth containing 25 μg/ml kanamycin. One aliquot was grown to prepare plasmid DNA by an alkaline lysis method. The other aliquot was grown by in vivo-packaging which was accomplished by previously described procedures (13). The titer of the lysate prepared from $_{\chi}$2764 transductants containing the pYUB178::H37Rv library was approximately $1\times10^9$ cfu/ml. The lysate was stored at 4° C. after filtering through a 0.45 μm pore sterile filter.

E. Construction of H37Ra (pYUB178::H37Rv) recombinant pools

An eight day old H37Ra culture was electroporated with the pYUB178::H37Rv library DNA in plasmid form, and separately, with pYUB178 DNA. Approximately 450 transformants arose from five independent electroporations of cells with approximately 1 μg library DNA each. Two pools of H37Ra (pYUB178::H37Rv) recombinants, pool 1 and pool 2, were made by collecting and inoculating approximately 225 colonies into 50 ml of enriched 7H9 broth containing 10 μg/ml kanamycin, and allowing growth for approximately two weeks. Aliquots of pools were distributed and frozen in cryovials for later use in animal experiments.

Another pool of H37Ra(pYUB178::H37Rv) recombinants, pool 3, consisted of approximately 260 clones and was used to determine whether the pools were representative. Recombinants of pool 3 were collected directly from plates of enriched Middlebrook 7H10 agar containing 25 μg/ml kanamycin after growth following electroporation; an aliquot was inoculated into enriched 7H9 broth without kanamycin and allowed to grow standing at 37° C. for approximately two weeks. Total DNA was isolated from pool 3 before and after growth in broth. DNA was subjected to Southern analysis using the 1.1. kb DraI/SspI DNA fragment of pYUB178 as a probe.

F. Mouse infection

In experiments J2, J2P, J5 and J5P that used the mouse to select individual recombinant clones from pools 1 and 2, and in subsequent growth measurement experiments, J33 and J36, groups of C57BL/6 mice aged 6–8 weeks were intravenously inoculated with 0.2 ml of each culture tested. Five mice were inoculated with each recombinant group or control group per timepoint. Inoculation of mice with spleen-passaged bacteria was accomplished by first homogenizing spleens after fourteen days infection in 5 ml sterile saline. One ml of the 5 ml spleen homogenate from each of the five mice per group was pooled and filtered through sterile gauze to exclude tissue clumps. The filtrate was used to directly inoculate another set of mice in experiments J2P and J5P. See Table 9 for details or mouse experiments.

Individual colonies that grew from plated lung homogenates in experiments J2P and J5P were picked and grown in enriched 7H9 broth for subsequent mouse experiments and DNA analyses.

G. Retrieval of pYUB178::H37Rv cosmids from chromosomes of in vivo-selected recombinants Chromosomal DNA was isolated from individual H37Ra (pYUB178::H37Rv) recombinant clones using chemical disruption of bacterial cells as previously described (28). DNA was partially digested with Sau3AI; fragments of 30–50 kb were size-fractionated and eluted from agarose gels as described above. The 30–50 kb fragments were ligated to the 975 bp BglII/BclI fragment containing cos of coliphage lambda DNA. The ligation conditions were such that the final DNA concentration was 50 to 100 ng/μl, and the molar ratio of chromosomal DNA fragments to cos DNA fragments was 1.

The ligation mixture was packaged into lambda phage heads and tails using the Stratagene GigaPack kit, and transduced into *E. coli* strain HB101. Individual kanamycin-resistant transductant colonies were picked and cosmid DNA was isolated. Cosmid DNA was then analyzed by restriction digestion and Southern hybridization.

H. Restriction and Southern analyses of retrieved cosmids

Digested cosmid DNA was subjected to agarose gel electrophoresis in 0.8w agarose in TAE buffer. DNA was Southern blotted from gels onto nylon membranes by capillary diffusion, UV-crosslinked and hybridized with probes derived from pYUB178. Probes consisted of either the 1.1 kb DraI/SspI fragment of pYUB178, or the 436 bp AseI/BclI fragment of pYUB178 that contained lambda DNA adjacent to cos, or the 756 bp AseI/BclI fragment of pYUB178 that contained part of aph. Probes were labeled Pharmacia oligolabeling kit (Pharmacia LKB Biotechnology AB, Uppsala, Sweden), or with horseradish peroxidase according to the protocol of the Enhanced Chemiluminescence ECL Gene Detection System (Amersham International, Amersham, UK).

I. Screening the pYUB178::H37Rv library in *E. coli*

The pYUB178::H37Rv library DNA lysate, $10^9$ cfu/ml, was serially diluted to a concentration of $10^4$ cfu/ml in SM buffer [50 mM Tris-Cl (pH 7.5), 100 mM NaCl, 8 mM $MgSo_4 \cdot 7H_2O$], and transduced into *E. coli* strain HB101. Aliquots of infected cells were plated onto L agar containing 25 µg/ml kanamycin such that each plate would contain approximately 150 colonies. After overnight incubation at 37° C., colonies from each plate were lifted onto Biotrans nylon filters (ICN Biomedicals, Inc., Irvine, Calif.). The filters were treated with denaturing buffer and neutralization buffer and UV-crosslinked. A probe was made from a cosmid, pYUB352, derived from the $mc^2806$ recombinant clone. The cosmid pYUB352 was linearized by digestion with AseI and labeled with $[\alpha^{-32}]$ dCTP. Filters were hybridized overnight according to the manufacturer's protocol (ICN Biomedicals, Inc.).

Thirty hybridizing clones were picked and streaked onto plates, and subjected to secondary screening with the pYUB352 probe. Ten strongly hybridizing clones were picked and analyzed by Southern hybridization with pYUB352 as a probe. Four cosmids, two that shared H37Rv restriction fragments with pYUB352, and two that did not share H37Rv restriction fragments with pYUB352, were electroporated individually into H37Ra.

J. In vivo growth of pYUB352-overlapping and -nonoverlapping recombinants

Single H37Ra transformant colonies from each of the four electroporations were grown in enriched 7H9 broth containing kanamycin to prepare sufficient culture for mouse experiments. The in vivo growth rates of H37Ra containing pYUB352-overlapping and -nonoverlapping clones were measured in the experiment designated J36 (see Table 9).

K. Results i. Construction of shuttle cosmid and H37Rv library The integrating cosmid pYUB178 contains an *E. coli* ori derived from pUC19, the L5 attP site, the L5 integrase gene, a kanamycin resistance gene, aph, derived from Tn903, the lambda cos sequence and a unique cloning site, BclI (see FIG. 4A). The L5 mycobacteriophage attachment site attP, and integrase gene, int, mediate site-specific integration into the mycobacterial chromosome (18). The H37Rv library was constructed by ligating 40 kb size-selected chromosomal DNA fragments, generated by partial digestion with Sau3AI, to alkaline phosphatase-treated pYUB178, linearized by digestion with BclI. The ligation mix was packaged into lambda phage heads and tails, and transduced into *E. coli*. The approximately 4000 kanamycin-resistant transductant colonies were theoretically enough to represent the H37Rv genome forty times. Twelve individual cosmids of the H37Rv library were isolated from randomly picked *E. coli* transductant colonies and examined by restriction analyses. No two cosmids were alike, and each cosmid had an insert size of 35–40 kb (data not shown). The H37Rv library DNA was isolated as plasmid from the complete pool of *E. coli* transductants and electroporated into H37Ra. To identify the H37Rv insert within the chromosome of a H37Ra (pYUB178::H37Rv) recombinant, a method to detect the H37Rv DNA fragments immediately adjacent to pYUB178 sequences was devised. The method of analysis depicted in FIG. 4B allows the identification of PstI restriction fragments of the H37Rv DNA at the junctions of pYUB178 sequences on either side of the BclI cloning site (see FIG. 4B). The pYUB178-H37Rv junctional fragments of individual H37Ra(pYUB178::H37Rv) recombinants are visible as bands in the Southern analysis in FIG. 4C, lanes 1–3.

To determine if a representative panel of H37Ra (pYUB178::H37Rv) recombinants was generated, approximately 260 transformant colonies, pool 3, were collected after growth on kanamycin-containing 7H10 agar; an aliquot of pool 3 was transferred to enriched 7H9 medium and allowed to grow for approximately two weeks. Chromosomal DNA was isolated from pool 3 both before and after growth in broth. These DNAs were subjected to PstI digestion and agarose gel electrophoresis, followed by transfer to a nylon membrane and hybridization to a pYUB178 probe (FIG. 4C). In FIG. 4C, the smears in lanes 4 and 5 reveal that the pool of H37Ra(pYUB178::H37Rv) recombinants consisted of members having different H37Rv DNA inserts, both before and after growth in broth, suggesting that the pools were representative and stable in the absence of kanamycin selection pressure.

ii. Enrichment and selection of putatively virulent recombinants from pools

Mice were intravenously infected with either H37Ra (pYUB178::H37Rv) recombinant pool 1 or 2. Two weeks post-infection, mouse spleens were individually homogenized, pooled, and used to infect a second group of mice. Individual recombinant colonies that grew from the plated lung homogenates prepared from the second group of mice were picked. To characterize the integrated cosmid in each recombinant, chromosomal DNAs were isolated from these individual recombinants and subjected to Southern analysis with a pYUB178 probe. The junctional fragment analyses of selected individual recombinants from the in vivo-passed pool 2 in experiment J5P (see Table 9) are shown in FIG. 4C, lanes 1, 2 and 3. Lane 1 shows the clone designated $mc^2807$, lane 2 shows the clone designated $mc^2806$, and lane 3 shows a clone that has junctional fragments identical to those of $mc^2806$. Because clones having junctional fragments identical to those of $mc^2806$ were isolated from many animals during two different experiments, J2P and J5P, (data not shown), $mc^2806$ was further characterized.

iii. In vivo growth rate comparisons

Growth rate comparisons of clones $mc^2806$, $mc^2816$ (H37Ra containing pYUB178, see Table 9) and H37Rv were made (see FIG. 5). Clone $mc^2$ 806 grew in the spleen at a rate that was slightly lower than the growth rate of H37Rv during the first two weeks of infection. Clone $mc^2$ 816 barely grew. After the initial growth phase, $mc^2806$ was cleared from the spleen at a lower rate than the rate of clearance of $mc^2816$. H37Rv persisted at its day 28 level, at least through the experimental endpoint, day 84. Clone $mc^2806$ did not grow faster than $mc^2816$ during the first two weeks in mouse lung (FIG. 5B). Therefore the faster in vivo growth rate of $mc^2806$ compared to $mc^2816$ was evident only in mouse spleen. The growth rates of $mc^2806$, $mc^2816$, and H37Rv in enriched 7H9 broth were virtually identical (data not shown).

iv. Identification of a H37Rv DNA insert that confers a faster in vivo growth rate to H37Ra To prove that the H37Rv DNA insert present in an in vivo-selected recombinant was responsible for its in vivo growth phenotype, it had to be retrieved from the chromosome. A disadvantage of the stably integrating pYUB178::H37Rv cosmid library is the difficulty of cosmid retrieval from the chromosome of a H37Ra (pYUB178::H37Rv) recombinant; the excision functions of L5 are not yet understood. Hence, a method was devised to clone the H37Rv DNA insert as a cosmid (see FIG. 6A). The lambda in vitro-packaged ligation mix that contained random pieces of the $mc^2806$ chromosome was transduced into *E. coli* for the purpose of selecting H37Rv DNA-containing cosmids. Only those cosmids containing the *E. coli* and aph replicated under kanamycin selection pressure (cf FIG. 6A). The Southern analyses of 16 of the 33 retrieved cosmids of $mc^2806$ from *E. coli* transductants is shown in FIG. 6B. The cosmids were digested with both EcoRI and AseI and analyzed by gel electrophoresis. The 434 bp probe, generated by digestion of pYUB178 with AseI and BclI, hybridized to the H37Rv/pYUB178 junction that included lambda DNA adjacent to cos. By comparing the sizes of the junctional fragments of the retrieved cosmids with the sizes of the junctional fragments of $mc^2806$ in lane 1, one can determine whether the entire H37Rv insert DNA has been retrieved. Only one of the 16 cosmids did not contain the full-sized H37Rv fragment adjacent to the pYUB178 junction (FIG. 6B, lane 14). The retrieval procedure was very efficient; 32 of the 33 $mc^2806$-retrieved cosmids contained the entire H37Rv insert (data not shown). The cosmid clone designated pYUB352 in lane 15 was used for further study.

v. Identification of pYUB352-overlapping cosmids from the pYUB178::H37Rv DNA library To prove that the H37Rv insert DNA was responsible for the spleen growth phenotype, it had to be reintroduced into H37Ra and tested. Reintroduction of the H37Rv insert DNA from the $mc^2806$ recombinant into H37Ra required a replicating vector. Retrieved cosmids did not have the ability to replicate in mycobacteria because they lost the int gene when they were removed from the chromosomes of the recombinants. Therefore, pYUB352 DNA was used as a probe to screen the pYUB178::H37RV library in *E. coli* for the H37Rv DNA insert associated with $mc^2806$. Colonies of *E. coli* (pYUB178::H37Rv) library transductants were transferred to nylon filters, lysed, and probed with pYUB352 DNA. Cosmids that shared H37Rv DNA with pYUB352, designated pYUB353 and pYUB354, and unrelated cosmids, designated pYUB355 and pYUB356, were separately transformed into H37Ra.

vi. The H37Rv DNA of $mc^2806$ confers in vivo growth advantage to H37Ra

The growth rates of H37Ra recombinant clones containing pYUB352-overlapping and -nonoverlapping cosmids were tested in mice (experiment J36, see Table 9). The H37Ra recombinants containing the pYUB352-overlapping cosmids grew as well as $mc^2806$, and the H37Ra recombinants containing pYUB352-nonoverlapping cosmids grew poorly or did not grow at all (FIG. 7). These data indicate that the H37Rv DNA that is shared by pYUB352, pYUB353, and pYUB354 expresses a gene or gene(s) associated with growth in the spleen.

vii. Mapping the ivg region of H37Rv

The pYUB352, pYUB353, and pYUB354 cosmids were mapped by restriction digest and analyzed by Southern hybridization (see FIG. 8). The schematic of FIG. 8C shows the physical map of the H37Rv DNA insert of each clone. A DNA region of approximately 25 kb is shared between the clones. This region was designated ivg or in vivo growth advantage.

TABLE 8

| Bacterial strain or clone | Description | Source |
|---|---|---|
| *E. coli* | | |
| HB101 | F-ara14 leuB6 proA2 lacY1 glnV44 galK21-recA13 rpsL20 xyl-5 mtl-1 thi-1 hsdS20 | (3) |
| $\chi^{2764}$ | HB101 lysogenized with λ cI857 b2 redβ3 S7 | (8) |
| DH5α | F-endA1 hsdR17 supE44 thi-1 1-recA1 gyrA96 relA1 Δ (argF-laczya) U169 Φ80dlacZ ΔM15 | BRL, Inc. |
| *M. tuberculosis* | | |
| $mc^2806$ | H37Ra containing pYUB178::H37Rv ivg | This study |
| $mc^2822$ | H37Ra containing pYUB353 | This study |
| $mc^2823$ | H37Ra containing pYUB354 | This study |
| $mc^2824$ | H37Ra containing pYUB355 | This study |
| $mc^2825$ | H37Ra containing pYUB356 | This study |
| Shuttle Plasmid | | |
| pYUB178 | Integrating shuttle cosmid vector | This study |
| pYUB352 | H37Rv ivg-containing cosmid derived from $mc^2806$ | This study |
| pYUB353 | pYUB178::H37Rv ivg | This study |
| pYUB354 | pYUB178::H37Rv ivg | This study |
| pYUB355 | pYUB178::H37Rv | This study |
| pYUB356 | pYUB178::H37Rv | This study |

TABLE 9

| Experiment | Pools and Clones Tested | Inocula (cfu/mouse) | Timepoints (day) |
|---|---|---|---|
| J2 | Pool 1 | $2 \times 10^5$ | 1, 14, 28 |
| | Pool 2 | $6 \times 10^5$ | |
| | $mc^2816$ | $1 \times 10^6$ | |
| J5 | Pool 1 | $1 \times 10^5$ | 1, 14, 28 |
| | Pool 2 | $6 \times 10^5$ | |
| | $mc^2816$ | $1 \times 10^6$ | |
| | H37Rv | $6 \times 10^4$ | |
| *J2P | Pool 1 | $5 \times 10^2$ | 1, 14 |
| | Pool 2 | $7 \times 10^2$ | |
| | $mc^2816$ | $5 \times 10^2$ | |
| *J5P | Pool 1 | $9 \times 10^2$ | 1, 14 |
| | Pool 2 | $7 \times 10^2$ | |
| | $mc^2816$ | $6 \times 10^3$ | |
| J33 | $mc^2806$, | $1\text{-}2 \times 10^4$ | 1, 14, 28, |
| | $mc^2816$, | $4 \times 10^4$ | 84 |
| | H37Rv | $5 \times 10^4$ | |
| J36 | $mc^2806$, | $1 \times 10^4$ | 2, 14, 28 |
| | $mc^2822$, | $1\text{-}2 \times 10^4$ | 87 |
| | $mc^2823$, | $1\text{-}3 \times 10^4$ | |
| | $mc^2824$ | $5 \times 10^4$ | |
| | $mc^2825$, | $6 \times 10^4$ | |
| | $mc^2816$, | $8 \times 10^4$ | |
| | H37Rv | $4 \times 10^4$ | |

*For J2P and J5P, inocula were estimated from cfu retained in the spleen on day 1; spleen retention is usually 10% of the inoculating dose.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 2745 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 835..2424

( x i ) SEQUENCE DESCRIPTION: SEQ ID NO:1:

| | | | | | |
|---|---|---|---|---|---|
| GATCAAGCTG | CTGACCCCGC | AACCGGCCAC | TCCGTTGGCG | GTCGCCAAAA | CCATCGCCGA | 60 |
| GGTCGTCAAC | GGTTTCGGCT | GGCGGGGTCC | GCTGGGGGTG | ACCTATCCCG | GCGTCGTCAC | 120 |
| TCACGGCGTC | GTCCGGACCG | CGGCTAACGT | GGACAAGTCC | TGGATAGGGA | CCAACGCACG | 180 |
| CGACACTATC | GGCGCCGAGC | TGGGCGGTCA | GCAGGTCACC | ATCCTCAACG | ACGCTGATGC | 240 |
| CGCCGGGCTG | GCCGAGACAC | GCTACGGGGC | CGGCAAGAAC | AACCCTGGCT | TAGTGGTACT | 300 |
| GCTCACATTC | GGAACCGGGA | TCGGGTCCGC | GGTCATCCAC | AACGGGACGT | TGATACCCAA | 360 |
| CACCGAGTTC | GGACATCTTG | AGGTCGGCGG | CAAGGAAGCG | GAGGAAAGGG | CCGCCTCCTC | 420 |
| GGTAAAGGAA | AAGAACGACT | GGACCTATCC | AAAGTGGGCC | AAGCAGGTGA | CACGCGTGCT | 480 |
| CATCGCCATC | GAGAACGCGA | TCTGGCCTGA | CCTGTTCATC | GCCGGCGGCG | GCATCAGCCG | 540 |
| CAAGGCCGAC | AAATGGGTGC | CGCTACTGGA | AAACCGCACA | CCAGTAGTGC | CCGCGGCCCT | 600 |
| GCAGAACACC | GCCGGAATTG | TCGGTGCGGC | CATGGCCTCT | GTCGCAGATA | CGACGCACTG | 660 |
| AAACTTGCCC | GCTCGGGCTG | TACTCGTGCG | CAGTAAAGTT | ACAATGGTCA | GCGGCGGCCG | 720 |
| CCCGACCGAT | AGCGCGCGAG | TATTCACGCT | GATATCAACG | CCGACATTCG | ACATAGCAGA | 780 |
| CACTTTCGGT | TACGCACGCC | CAGACCCAAC | CGGAAGTGAG | TAACGACCGA | AGGG GTG | 837 |
| | | | | | Val |
| | | | | | 1 |

| TAT | GTG | GCA | GCG | ACC | AAA | GCA | AGC | ACG | GCG | ACC | GAT | GAG | CCG | GTA | AAA | 885 |
|---|---|---|---|---|---|---|---|---|---|---|---|---|---|---|---|---|
| Tyr | Val | Ala | Ala | Thr | Lys | Ala | Ser | Thr | Ala | Thr | Asp | Glu | Pro | Val | Lys | |
| | | | 5 | | | | 10 | | | | 15 | | | | | |

| CGC | ACC | GCC | ACC | AAG | TCG | CCC | GCG | GCT | TCC | GCG | TCC | GGG | GCC | AAG | ACC | 933 |
|---|---|---|---|---|---|---|---|---|---|---|---|---|---|---|---|---|
| Arg | Thr | Ala | Thr | Lys | Ser | Pro | Ala | Ala | Ser | Ala | Ser | Gly | Ala | Lys | Thr | |
| | | 20 | | | | 25 | | | | | 30 | | | | | |

| GGC | CCC | AAG | CGA | ACA | GCG | GCG | AAG | TCC | GCT | AGT | GGC | TCC | CCA | CCC | GCG | 981 |
|---|---|---|---|---|---|---|---|---|---|---|---|---|---|---|---|---|
| Gly | Pro | Lys | Arg | Thr | Ala | Ala | Lys | Ser | Ala | Ser | Gly | Ser | Pro | Pro | Ala | |
| | 35 | | | | 40 | | | | | 45 | | | | | | |

| AAG | CGG | GCT | ACC | AAG | CCC | GCG | GCC | CGG | TCC | GTC | AAG | CCC | GCC | TCG | GCA | 1029 |
|---|---|---|---|---|---|---|---|---|---|---|---|---|---|---|---|---|
| Lys | Arg | Ala | Thr | Lys | Pro | Ala | Ala | Arg | Ser | Val | Lys | Pro | Ala | Ser | Ala | |
| 50 | | | | | 55 | | | | | 60 | | | | | 65 | |

| CCC | CAG | GAC | ACT | ACG | ACC | AGC | ACC | ATC | CCG | AAA | AGG | AAG | ACC | CGC | GCC | 1077 |
|---|---|---|---|---|---|---|---|---|---|---|---|---|---|---|---|---|
| Pro | Gln | Asp | Thr | Thr | Thr | Ser | Thr | Ile | Pro | Lys | Arg | Lys | Thr | Arg | Ala | |
| | | | | 70 | | | | | 75 | | | | | 80 | | |

| GCG | GCC | AAA | TCC | GCC | GCC | GCG | AAG | GCA | CCG | TCG | GCC | CGC | GGC | CAC | GCG | 1125 |
|---|---|---|---|---|---|---|---|---|---|---|---|---|---|---|---|---|
| Ala | Ala | Lys | Ser | Ala | Ala | Ala | Lys | Ala | Pro | Ser | Ala | Arg | Gly | His | Ala | |
| | | | 85 | | | | | 90 | | | | | 95 | | | |

| ACC | AAG | CCA | CGG | GCG | CCC | AAG | GAT | GCC | CAG | CAC | GAA | GCC | GCA | ACG | GAT | 1173 |
|---|---|---|---|---|---|---|---|---|---|---|---|---|---|---|---|---|
| Thr | Lys | Pro | Arg | Ala | Pro | Lys | Asp | Ala | Gln | His | Glu | Ala | Ala | Thr | Asp | |
| | | 100 | | | | 105 | | | | | 110 | | | | | |

```
CCC GAG GAC GCC CTG GAC TCC GTC GAG GAG CTC GAC GCT GAA CCA GAC      1221
Pro Glu Asp Ala Leu Asp Ser Val Glu Glu Leu Asp Ala Glu Pro Asp
    115             120                 125

CTC GAC GTC GAG CCC GGC GAG GAC CTC GAC CTT GAC GCC GCC GAC CTC      1269
Leu Asp Val Glu Pro Gly Glu Asp Leu Asp Leu Asp Ala Ala Asp Leu
130             135                 140                 145

AAC CTC GAT GAC CTC GAG GAC GAC GTG GCG CCG GAC GCC GAC GAC GAC      1317
Asn Leu Asp Asp Leu Glu Asp Asp Val Ala Pro Asp Ala Asp Asp Asp
            150                 155                 160

CTC GAC TCG GGC GAC GAC GAA GAC CAC GAA GAC CTC GAA GCT GAG GCG      1365
Leu Asp Ser Gly Asp Asp Glu Asp His Glu Asp Leu Glu Ala Glu Ala
                165                 170                 175

GCC GTC GCG CCC GGC CAG ACC GCC GAT GAC GAC GAG GAG ATC GCT GAA      1413
Ala Val Ala Pro Gly Gln Thr Ala Asp Asp Asp Glu Glu Ile Ala Glu
            180                 185                 190

CCC ACC GAA AAG GAC AAG GCC TCC GGT GAT TTC GTC TGG GAT GAA GAC      1461
Pro Thr Glu Lys Asp Lys Ala Ser Gly Asp Phe Val Trp Asp Glu Asp
    195                 200                 205

GAG TCG GAG GCC CTG CGT CAA GCA CGC AAG GAC GCC GAA CTC ACC GCA      1509
Glu Ser Glu Ala Leu Arg Gln Ala Arg Lys Asp Ala Glu Leu Thr Ala
210                 215                 220                 225

TCC GCC GAC TCG GTT CGC GCC TAC CTC AAA CAG ATC GGC AAG GTA GCG      1557
Ser Ala Asp Ser Val Arg Ala Tyr Leu Lys Gln Ile Gly Lys Val Ala
                230                 235                 240

CTG CTC AAC GCC GAG GAA GAG GTC GAG CTA GCC AAG CGG ATC GAG GCT      1605
Leu Leu Asn Ala Glu Glu Glu Val Glu Leu Ala Lys Arg Ile Glu Ala
            245                 250                 255

GGC CTG TAC GCC ACG CAG CTG ATG ACC GAG CTT AGC GAG CGC GGC GAA      1653
Gly Leu Tyr Ala Thr Gln Leu Met Thr Glu Leu Ser Glu Arg Gly Glu
        260                 265                 270

AAG CTG CCT GCC GCC CAG CGC CGC GAC ATG ATG TGG ATC TGC CGC GAC      1701
Lys Leu Pro Ala Ala Gln Arg Arg Asp Met Met Trp Ile Cys Arg Asp
275                 280                 285

GGC GAT CGC GCG AAA AAC CAT CTG CTG GAA GCC AAC CTG CGC CTG GTG      1749
Gly Asp Arg Ala Lys Asn His Leu Leu Glu Ala Asn Leu Arg Leu Val
290                 295                 300                 305

GTT TCG CTA GCC AAG CGC TAC ACC GGC CGG GGC ATG GCG TTT CTC GAC      1797
Val Ser Leu Ala Lys Arg Tyr Thr Gly Arg Gly Met Ala Phe Leu Asp
            310                 315                 320

CTG ATC CAG GAA GGC AAC CTG GGG CTG ATC CGC GCG GTG GAG AAG TTC      1845
Leu Ile Gln Glu Gly Asn Leu Gly Leu Ile Arg Ala Val Glu Lys Phe
                325                 330                 335

GAC TAC ACC AAG GGG TAC AAG TTC TCC ACC TAC GCT ACG TGG TGG ATT      1893
Asp Tyr Thr Lys Gly Tyr Lys Phe Ser Thr Tyr Ala Thr Trp Trp Ile
            340                 345                 350

CGC CAG GCC ATC ACC CGC GCC ATG GCC GAC CAG GCC CGC ACC ATC CGC      1941
Arg Gln Ala Ile Thr Arg Ala Met Ala Asp Gln Ala Arg Thr Ile Arg
355                 360                 365

ATC CCG GTG CAC ATG GTC GAG GTG ATC AAC AAG CTG GGC CGC ATT CAA      1989
Ile Pro Val His Met Val Glu Val Ile Asn Lys Leu Gly Arg Ile Gln
370                 375                 380                 385

CGC GAG CTG CTG CAG GAC CTG GGC CGC GAG CCC ACG CCC GAG GAG CTG      2037
Arg Glu Leu Leu Gln Asp Leu Gly Arg Glu Pro Thr Pro Glu Glu Leu
            390                 395                 400

GCC AAA GAG ATG GAC ATC ACC CCG GAG AAG GTG CTG GAA ATC CAG CAA      2085
Ala Lys Glu Met Asp Ile Thr Pro Glu Lys Val Leu Glu Ile Gln Gln
        405                 410                 415

TAC GCC CGC GAG CCG ATC TCG TTG GAC CAG ACC ATC GGC GAC GAG GGC      2133
Tyr Ala Arg Glu Pro Ile Ser Leu Asp Gln Thr Ile Gly Asp Glu Gly
    420                 425                 430
```

| | | | | | | | | | | | | | | | | |
|---|---|---|---|---|---|---|---|---|---|---|---|---|---|---|---|---|
| GAC | AGC | CAG | CTT | GGC | GAT | TTC | ATC | GAA | GAC | AGC | GAG | GCG | GTG | GTG | GCC | 2181 |
| Asp | Ser | Gln | Leu | Gly | Asp | Phe | Ile | Glu | Asp | Ser | Glu | Ala | Val | Val | Ala | |
| 435 | | | | | 440 | | | | | 445 | | | | | | |
| GTC | GAC | GCG | GTG | TCC | TTC | ACT | TTG | CTG | CAG | GAT | CAA | CTG | CAG | TCG | GTG | 2229 |
| Val | Asp | Ala | Val | Ser | Phe | Thr | Leu | Leu | Gln | Asp | Gln | Leu | Gln | Ser | Val | |
| 450 | | | | | 455 | | | | | 460 | | | | | 465 | |
| CTG | GAC | ACG | CTC | TCC | GAG | CGT | GAG | GCG | GGC | GTG | GTG | CGG | CTA | CGC | TTC | 2277 |
| Leu | Asp | Thr | Leu | Ser | Glu | Arg | Glu | Ala | Gly | Val | Val | Arg | Leu | Arg | Phe | |
| | | | | 470 | | | | | 475 | | | | | 480 | | |
| GGC | CTT | ACC | GAC | GGC | CAG | CCG | CGC | ACC | CTT | GAC | GAG | ATC | GGC | CAG | GTC | 2325 |
| Gly | Leu | Thr | Asp | Gly | Gln | Pro | Arg | Thr | Leu | Asp | Glu | Ile | Gly | Gln | Val | |
| | | | 485 | | | | | 490 | | | | | 495 | | | |
| TAC | GGC | GTG | ACC | CGG | GAA | CGC | ATC | CGC | CAG | ATC | GAA | TCC | AAG | ACT | ATG | 2373 |
| Tyr | Gly | Val | Thr | Arg | Glu | Arg | Ile | Arg | Gln | Ile | Glu | Ser | Lys | Thr | Met | |
| | | 500 | | | | | 505 | | | | | 510 | | | | |
| TCG | AAG | TTG | CGC | CAT | CCG | AGC | CGC | TCA | CAG | GTC | CTG | CGC | GAC | TAC | CTG | 2421 |
| Ser | Lys | Leu | Arg | His | Pro | Ser | Arg | Ser | Gln | Val | Leu | Arg | Asp | Tyr | Leu | |
| | 515 | | | | | 520 | | | | | 525 | | | | | |
| GAC | TGAGAGCGCC | CGCCGAGGCG | ACCAACGTAG | CGGGCCCCCA | TGTCAGCTAG | | | | | | | | | | | 2474 |
| Asp | | | | | | | | | | | | | | | | |
| 530 | | | | | | | | | | | | | | | | |

CCGCACCATG GTCTCGTCCG GATCGGAGTT CGAATCAGCC GTCGGCTACT CGCGCGCGGT 2534

ACGCATCGGG CCACTCGTGG TGGTGGCCGG AACGACCGGC AGCGGCGATG ATATCGTCGC 2594

TCAGACGCGA GACGCTCTGC GCCGCATCGA GATTGCGCTC GGACAGGCCG GCGCAACTCT 2654

GGCCGACGTG GTCCGTACCC GCATCTATGT GACCGATATT TCCCGCTGGC GCGAGGTCGG 2714

CGAAGTGCAT GCACAGGCTT TCGGCAAGAT C 2745

( 2 ) INFORMATION FOR SEQ ID NO:2:

( i ) SEQUENCE CHARACTERISTICS:
        ( A ) LENGTH: 530 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Val | Tyr | Val | Ala | Ala | Thr | Lys | Ala | Ser | Thr | Ala | Thr | Asp | Glu | Pro | Val |
| 1 | | | | 5 | | | | | 10 | | | | | 15 | |
| Lys | Arg | Thr | Ala | Thr | Lys | Ser | Pro | Ala | Ala | Ser | Ala | Ser | Gly | Ala | Lys |
| | | | 20 | | | | | 25 | | | | | 30 | | |
| Thr | Gly | Pro | Lys | Arg | Thr | Ala | Ala | Lys | Ser | Ala | Ser | Gly | Ser | Pro | Pro |
| | | | 35 | | | | 40 | | | | | 45 | | | |
| Ala | Lys | Arg | Ala | Thr | Lys | Pro | Ala | Ala | Arg | Ser | Val | Lys | Pro | Ala | Ser |
| | 50 | | | | | 55 | | | | | 60 | | | | |
| Ala | Pro | Gln | Asp | Thr | Thr | Thr | Ser | Thr | Ile | Pro | Lys | Arg | Lys | Thr | Arg |
| 65 | | | | | 70 | | | | | 75 | | | | | 80 |
| Ala | Ala | Ala | Lys | Ser | Ala | Ala | Ala | Lys | Ala | Pro | Ser | Ala | Arg | Gly | His |
| | | | | 85 | | | | | 90 | | | | | 95 | |
| Ala | Thr | Lys | Pro | Arg | Ala | Pro | Lys | Asp | Ala | Gln | His | Glu | Ala | Ala | Thr |
| | | | | 100 | | | | | 105 | | | | | 110 | |
| Asp | Pro | Glu | Asp | Ala | Leu | Asp | Ser | Val | Glu | Glu | Leu | Asp | Ala | Glu | Pro |
| | | | 115 | | | | | 120 | | | | | 125 | | |
| Asp | Leu | Asp | Val | Glu | Pro | Gly | Glu | Asp | Leu | Asp | Leu | Asp | Ala | Ala | Asp |
| | | 130 | | | | | 135 | | | | | 140 | | | |
| Leu | Asn | Leu | Asp | Asp | Leu | Glu | Asp | Asp | Val | Ala | Pro | Asp | Ala | Asp | Asp |
| 145 | | | | | 150 | | | | | 155 | | | | | 160 |

| Asp | Leu | Asp | Ser | Gly 165 | Asp | Asp | Glu | Asp | His 170 | Glu | Asp | Leu | Glu | Ala 175 | Glu |
|---|---|---|---|---|---|---|---|---|---|---|---|---|---|---|---|
| Ala | Ala | Val | Ala 180 | Pro | Gly | Gln | Thr | Ala 185 | Asp | Asp | Glu | Glu 190 | Ile | Ala |  |
| Glu | Pro | Thr 195 | Glu | Lys | Asp | Lys | Ala 200 | Ser | Gly | Asp | Phe | Val 205 | Trp | Asp | Glu |
| Asp | Glu 210 | Ser | Glu | Ala | Leu | Arg 215 | Gln | Ala | Arg | Lys | Asp 220 | Ala | Glu | Leu | Thr |
| Ala 225 | Ser | Ala | Asp | Ser | Val 230 | Arg | Ala | Tyr | Leu | Lys 235 | Gln | Ile | Gly | Lys | Val 240 |
| Ala | Leu | Leu | Asn | Ala 245 | Glu | Glu | Val | Glu 250 | Leu | Ala | Lys | Arg | Ile 255 | Glu |  |
| Ala | Gly | Leu | Tyr 260 | Ala | Thr | Gln | Leu | Met 265 | Thr | Glu | Leu | Ser | Glu 270 | Arg | Gly |
| Glu | Lys | Leu 275 | Pro | Ala | Ala | Gln | Arg 280 | Arg | Asp | Met | Met | Trp 285 | Ile | Cys | Arg |
| Asp | Gly 290 | Asp | Arg | Ala | Lys | Asn 295 | His | Leu | Leu | Glu | Ala 300 | Asn | Leu | Arg | Leu |
| Val 305 | Val | Ser | Leu | Ala | Lys 310 | Arg | Tyr | Thr | Gly | Arg 315 | Gly | Met | Ala | Phe | Leu 320 |
| Asp | Leu | Ile | Gln | Glu 325 | Gly | Asn | Leu | Gly | Leu 330 | Ile | Arg | Ala | Val | Glu 335 | Lys |
| Phe | Asp | Tyr | Thr 340 | Lys | Gly | Tyr | Lys | Phe 345 | Ser | Thr | Tyr | Ala | Thr 350 | Trp | Trp |
| Ile | Arg | Gln 355 | Ala | Ile | Thr | Arg | Ala 360 | Met | Ala | Asp | Gln | Ala 365 | Arg | Thr | Ile |
| Arg | Ile 370 | Pro | Val | His | Met | Val 375 | Glu | Val | Ile | Asn | Lys 380 | Leu | Gly | Arg | Ile |
| Gln 385 | Arg | Glu | Leu | Leu | Gln 390 | Asp | Leu | Gly | Arg | Glu 395 | Pro | Thr | Pro | Glu | Glu 400 |
| Leu | Ala | Lys | Glu | Met 405 | Asp | Ile | Thr | Pro | Glu 410 | Lys | Val | Leu | Glu | Ile 415 | Gln |
| Gln | Tyr | Ala | Arg 420 | Glu | Pro | Ile | Ser | Leu 425 | Asp | Gln | Thr | Ile | Gly 430 | Asp | Glu |
| Gly | Asp | Ser 435 | Gln | Leu | Gly | Asp | Phe 440 | Ile | Glu | Asp | Ser | Glu 445 | Ala | Val | Val |
| Ala | Val 450 | Asp | Ala | Val | Ser | Phe 455 | Thr | Leu | Leu | Gln | Asp 460 | Gln | Leu | Gln | Ser |
| Val 465 | Leu | Asp | Thr | Leu | Ser 470 | Glu | Arg | Glu | Ala | Gly 475 | Val | Val | Arg | Leu | Arg 480 |
| Phe | Gly | Leu | Thr | Asp 485 | Gly | Gln | Pro | Arg | Thr 490 | Leu | Asp | Glu | Ile | Gly 495 | Gln |
| Val | Tyr | Gly | Val 500 | Thr | Arg | Glu | Arg | Ile 505 | Arg | Gln | Ile | Glu | Ser 510 | Lys | Thr |
| Met | Ser | Lys 515 | Leu | Arg | His | Pro | Ser 520 | Arg | Ser | Gln | Val | Leu 525 | Arg | Asp | Tyr |
| Leu | Asp 530 |  |  |  |  |  |  |  |  |  |  |  |  |  |  |

( 2 ) INFORMATION FOR SEQ ID NO:3:

( i ) SEQUENCE CHARACTERISTICS:
( A ) LENGTH: 530 amino acids
( B ) TYPE: amino acid
( C ) STRANDEDNESS: single
( D ) TOPOLOGY: linear ( x i ) SEQUENCE DESCRIPTION: SEQ ID NO:3:

```
Val Tyr Val Ala Ala Thr Lys Ala Ser Thr Ala Thr Asp Glu Pro Val
 1           5                  10                  15
Lys Arg Thr Ala Thr Lys Ser Pro Ala Ala Ser Ala Ser Gly Ala Lys
             20                  25                  30
Thr Gly Pro Lys Arg Thr Ala Ala Lys Ser Ala Ser Gly Ser Pro Pro
         35                  40                  45
Ala Lys Arg Ala Thr Lys Pro Ala Ala Arg Ser Val Lys Pro Ala Ser
65      50                  55                  60
Ala Pro Gln Asp Thr Thr Thr Ser Thr Ile Pro Lys Arg Lys Thr Arg
65                  70                  75                  80
Ala Ala Ala Lys Ser Ala Ala Ala Lys Ala Pro Ser Ala Arg Gly His
                 85                  90                  95
Ala Thr Lys Pro Arg Ala Pro Lys Asp Ala Gln His Glu Ala Ala Thr
             100                 105                 110
Asp Pro Glu Asp Ala Leu Asp Ser Val Glu Glu Leu Asp Ala Glu Pro
             115                 120                 125
Asp Leu Asp Val Glu Pro Gly Asp Leu Asp Leu Asp Ala Ala Asp
130                 135                 140
Leu Asn Leu Asp Asp Leu Glu Asp Asp Val Ala Pro Asp Ala Asp Asp
145                 150                 155                 160
Asp Leu Asp Ser Gly Asp Asp Glu Asp His Glu Asp Leu Glu Ala Glu
                 165                 170                 175
Ala Ala Val Ala Pro Gly Gln Thr Ala Asp Asp Asp Glu Glu Ile Ala
             180                 185                 190
Glu Pro Thr Glu Lys Asp Lys Ala Ser Gly Asp Phe Val Trp Asp Glu
             195                 200                 205
Asp Glu Ser Glu Ala Leu Arg Gln Ala Arg Lys Asp Ala Glu Leu Thr
         210                 215                 220
Ala Ser Ala Asp Ser Val Arg Ala Tyr Leu Lys Gln Ile Gly Lys Val
225                 230                 235                 240
Ala Leu Leu Asn Ala Glu Glu Val Glu Leu Ala Lys Arg Ile Glu
                 245                 250                 255
Ala Gly Leu Tyr Ala Thr Gln Leu Met Thr Glu Leu Ser Glu Arg Gly
             260                 265                 270
Glu Lys Leu Pro Ala Ala Gln Arg Arg Asp Met Met Trp Ile Cys Arg
         275                 280                 285
Asp Gly Asp Arg Ala Lys Asn His Leu Leu Glu Ala Asn Leu Arg Leu
         290                 295                 300
Val Val Ser Leu Ala Lys Arg Tyr Thr Gly Arg Gly Met Ala Phe Leu
305                 310                 315                 320
Asp Leu Ile Gln Glu Gly Asn Leu Gly Leu Ile Arg Ala Val Glu Lys
                 325                 330                 335
Phe Asp Tyr Thr Lys Gly Tyr Lys Phe Ser Thr Tyr Ala Thr Trp Trp
             340                 345                 350
Ile Arg Gln Ala Ile Thr Arg Ala Met Ala Asp Gln Ala Arg Thr Ile
             355                 360                 365
Arg Ile Pro Val His Met Val Glu Val Ile Asn Lys Leu Gly Arg Ile
370                 375                 380
Gln Arg Glu Leu Leu Gln Asp Leu Gly Arg Glu Pro Thr Pro Glu Glu
385                 390                 395                 400
Leu Ala Lys Glu Met Asp Ile Thr Pro Glu Lys Val Leu Glu Ile Gln
                 405                 410                 415
```

-continued

```
Gln  Tyr  Ala  Arg  Glu  Pro  Ile  Ser  Leu  Asp  Gln  Thr  Ile  Gly  Asp  Glu
               420                      425                     430

Gly  Asp  Ser  Gln  Leu  Gly  Asp  Phe  Ile  Glu  Asp  Ser  Glu  Ala  Val  Val
          435                      440                     445

Ala  Val  Asp  Ala  Val  Ser  Phe  Thr  Leu  Leu  Gln  Asp  Gln  Leu  Gln  Ser
     450                      455                     460

Val  Leu  Asp  Thr  Leu  Ser  Glu  Arg  Glu  Ala  Gly  Val  Val  Arg  Leu  Arg
465                      470                     475                         480

Phe  Gly  Leu  Thr  Asp  Gly  Gln  Pro  Arg  Thr  Leu  Asp  Glu  Ile  Gly  Gln
               485                      490                          495

Val  Tyr  Gly  Val  Thr  Arg  Glu  Arg  Ile  Arg  Gln  Ile  Glu  Ser  Lys  Thr
               500                      505                     510

Met  Ser  Lys  Leu  Arg  His  Pro  Ser  Arg  Ser  Gln  Val  Leu  Arg  Asp  Tyr
          515                      520                     525

Leu  Asp
     530
```

( 2 ) INFORMATION FOR SEQ ID NO:4:

( i ) SEQUENCE CHARACTERISTICS:
        ( A ) LENGTH: 442 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Met  Val  Ser  Ala  Ala  Glu  Pro  Lys  Arg  Thr  Arg  Lys  Ser  Val  Ala  Ala
1                   5                        10                      15

Lys  Ser  Pro  Ala  Lys  Arg  Thr  Ala  Thr  Lys  Ala  Val  Ala  Ala  Asn  Pro
               20                      25                      30

Val  Thr  Ser  Arg  Lys  Ala  Thr  Ala  Pro  Ala  Ala  Pro  Ala  Ala  Pro  Ala
          35                      40                      45

Thr  Glu  Pro  Ala  Ala  Val  Glu  Glu  Glu  Ala  Pro  Ala  Lys  Lys  Ala  Ala
     50                      55                      60

Ala  Lys  Lys  Thr  Thr  Ala  Lys  Lys  Ala  Thr  Ala  Lys  Lys  Thr  Thr  Ala
65                       70                      75                          80

Lys  Lys  Ala  Ala  Ala  Lys  Lys  Thr  Thr  Ala  Lys  Lys  Glu  Asp  Gly  Glu
               85                      90                      95

Leu  Leu  Glu  Asp  Glu  Ala  Thr  Glu  Glu  Pro  Lys  Ala  Ala  Thr  Glu  Glu
               100                     105                     110

Pro  Glu  Gly  Thr  Glu  Asn  Ala  Gly  Phe  Val  Leu  Ser  Asp  Glu  Asp  Glu
          115                     120                     125

Asp  Asp  Ala  Pro  Ala  Gln  Gln  Val  Ala  Ala  Ala  Gly  Ala  Thr  Ala  Asp
     130                     135                     140

Pro  Val  Lys  Asp  Tyr  Leu  Lys  Gln  Ile  Gly  Lys  Val  Pro  Leu  Leu  Asn
145                     150                     155                         160

Ala  Glu  Gln  Glu  Val  Glu  Leu  Ala  Lys  Arg  Ile  Glu  Ala  Gly  Leu  Phe
               165                     170                     175

Ala  Glu  Asp  Lys  Leu  Ala  Asn  Ser  Asp  Lys  Leu  Ala  Pro  Lys  Leu  Lys
               180                     185                     190

Arg  Glu  Leu  Glu  Ile  Ile  Ala  Glu  Asp  Gly  Arg  Arg  Ala  Lys  Asn  His
          195                     200                     205

Leu  Leu  Glu  Ala  Asn  Leu  Arg  Leu  Val  Val  Ser  Leu  Ala  Lys  Arg  Tyr
     210                     215                     220

Thr  Gly  Arg  Gly  Met  Leu  Phe  Leu  Asp  Leu  Ile  Gln  Glu  Gly  Asn  Leu
225                     230                     235                         240
```

```
Gly  Leu  Ile  Arg  Ala  Val  Glu  Lys  Phe  Asp  Tyr  Thr  Lys  Gly  Tyr  Lys
               245                 250                      255

Phe  Ser  Thr  Tyr  Ala  Thr  Trp  Trp  Ile  Arg  Gln  Ala  Ile  Thr  Arg  Ala
               260                 265                      270

Met  Ala  Asp  Gln  Ala  Arg  Thr  Ile  Arg  Ile  Pro  Val  His  Met  Val  Glu
          275                      280                 285

Val  Ile  Asn  Lys  Leu  Ala  Arg  Val  Gln  Arg  Gln  Met  Leu  Gln  Asp  Leu
     290                      295                 300

Gly  Arg  Glu  Pro  Thr  Pro  Glu  Glu  Leu  Ala  Lys  Glu  Leu  Asp  Met  Thr
305                      310                 315                           320

Pro  Glu  Lys  Val  Ile  Glu  Val  Gln  Lys  Tyr  Gly  Arg  Glu  Pro  Ile  Ser
                    325                 330                           335

Leu  His  Thr  Pro  Leu  Gly  Glu  Asp  Gly  Asp  Ser  Glu  Phe  Gly  Asp  Leu
               340                 345                      350

Ile  Glu  Asp  Ser  Glu  Ala  Val  Val  Pro  Ala  Asp  Ala  Val  Ser  Phe  Thr
          355                      360                 365

Leu  Leu  Gln  Glu  Gln  Leu  His  Ser  Val  Leu  Asp  Thr  Leu  Ser  Glu  Arg
     370                      375                 380

Glu  Ala  Gly  Val  Val  Ser  Met  Arg  Phe  Gly  Leu  Thr  Asp  Gly  Gln  Pro
385                      390                 395                           400

Lys  Thr  Leu  Asp  Glu  Ile  Gly  Lys  Val  Tyr  Gly  Val  Thr  Arg  Glu  Arg
                    405                 410                           415

Ile  Arg  Gln  Ile  Glu  Ser  Lys  Thr  Met  Ser  Lys  Leu  Arg  His  Pro  Ser
               420                 425                      430

Arg  Ser  Gln  Val  Leu  Arg  Asp  Tyr  Leu  Asp
          435                 440
```

(2) INFORMATION FOR SEQ ID NO:5:

( i ) SEQUENCE CHARACTERISTICS:
        ( A ) LENGTH: 445 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Met  Val  Ser  Ala  Ala  Glu  Ser  Pro  Lys  Arg  Ala  Arg  Lys  Ser  Val  Ala
1              5                     10                      15

Ala  Lys  Ser  Pro  Val  Lys  Arg  Thr  Ala  Thr  Lys  Thr  Val  Ala  Ala  Lys
               20                 25                      30

Thr  Thr  Val  Thr  Arg  Thr  Val  Ala  Ala  Thr  Ala  Ala  Pro  Ala  Val  Glu
          35                      40                 45

Ser  Ala  Asp  Ala  Ala  Asp  Ala  Val  Ala  Ala  Ala  Pro  Ala  Lys  Lys
     50                      55                 60

Thr  Ala  Ala  Lys  Lys  Ala  Thr  Ala  Lys  Lys  Ala  Ala  Lys  Lys  Thr
65                   70                      75                       80

Thr  Ala  Lys  Lys  Thr  Ala  Ala  Lys  Lys  Ser  Gly  Lys  Gln  Asp  Asp  Glu
               85                      90                      95

Ile  Leu  Asp  Gly  Asp  Glu  Ala  Ala  Glu  Glu  Val  Lys  Ala  Gly  Lys  Gly
               100                     105                      110

Glu  Glu  Glu  Glu  Gly  Glu  Gly  Glu  Asn  Lys  Gly  Phe  Val  Leu  Ser  Asp
          115                     120                      125

Asp  Asp  Glu  Asp  Asp  Ala  Pro  Ala  Gln  Gln  Val  Ala  Val  Ala  Gly  Ala
     130                     135                      140

Thr  Ala  Asp  Pro  Val  Lys  Asp  Tyr  Leu  Lys  Gln  Ile  Gly  Lys  Val  Pro
145                     150                      155                       160
```

```
Leu Leu Asn Ala Glu Gln Glu Val Glu Leu Ala Lys Arg Ile Glu Ala
            165                 170                 175
Gly Leu Phe Ala Glu Asp Lys Leu Ala Asn Ala Asp Lys Leu Ala Pro
            180                 185                 190
Lys Leu Lys Arg Glu Leu Glu Ile Ile Ala Glu Asp Gly Arg Arg Ala
            195                 200                 205
Lys Asn His Leu Leu Glu Ala Asn Leu Arg Leu Val Val Ser Leu Ala
            210                 215                 220
Lys Arg Tyr Thr Gly Arg Gly Met Leu Phe Leu Asp Leu Ile Gln Glu
    225                 230                 235                 240
Gly Asn Leu Gly Leu Ile Arg Ala Val Glu Lys Phe Asp Tyr Thr Lys
                    245                 250                 255
Gly Tyr Lys Phe Ser Thr Tyr Ala Thr Trp Trp Ile Arg Gln Ala Ile
                260                 265                 270
Thr Arg Ala Met Ala Asp Gln Ala Arg Thr Ile Arg Ile Pro Val His
            275                 280                 285
Met Val Glu Val Ile Asn Lys Leu Ala Arg Val Gln Arg Gln Met Leu
    290                 295                 300
Gln Asp Leu Gly Arg Glu Pro Thr Pro Glu Glu Leu Ala Lys Glu Leu
305                 310                 315                 320
Asp Met Thr Pro Glu Lys Val Ile Glu Val Gln Lys Tyr Gly Arg Glu
                325                 330                 335
Pro Ile Ser Leu His Thr Pro Leu Gly Glu Asp Gly Asp Ser Glu Phe
            340                 345                 350
Gly Asp Leu Ile Glu Asp Ser Glu Ala Val Val Pro Ala Asp Ala Val
            355                 360                 365
Ser Phe Thr Leu Leu Gln Glu Gln Leu His Ser Val Leu Asp Thr Leu
    370                 375                 380
Ser Glu Arg Glu Ala Gly Val Val Ser Met Arg Phe Gly Leu Thr Asp
385                 390                 395                 400
Gly Gln Pro Lys Thr Leu Asp Glu Ile Gly Lys Val Tyr Gly Val Thr
                405                 410                 415
Arg Glu Arg Ile Arg Gln Ile Glu Ser Lys Thr Met Ser Lys Leu Arg
            420                 425                 430
His Pro Ser Arg Ser Gln Val Leu Arg Asp Tyr Leu Asp
            435                 440                 445
```

(2) INFORMATION FOR SEQ ID NO:6:

(i) SEQUENCE CHARACTERISTICS:
(A) LENGTH: 310 amino acids
(B) TYPE: amino acid
(C) STRANDEDNESS: single
(D) TOPOLOGY: linear (xi) SEQUENCE DESCRIPTION: SEQ ID NO:6:

```
Met Val Ser Ala Ala Glu Ser Pro Lys Arg Ala Arg Lys Ser Val Ala
1               5                   10                  15
Ala Lys Ser Pro Val Lys Arg Thr Ala Thr Lys Thr Val Ala Ala Lys
            20                  25                  30
Thr Thr Val Thr Arg Thr Val Ala Ala Thr Ala Ala Pro Ala Val Glu
            35                  40                  45
Ser Ala Asp Ala Ala Asp Asp Val Ala Ala Pro Ala Lys Lys
    50                  55                  60
Thr Ala Ala Lys Lys Ala Thr Ala Lys Lys Ala Ala Lys Lys Thr
65                  70                  75                  80
```

```
Thr Ala Lys Lys Thr Ala Ala Lys Lys Ser Gly Lys Gln Asp Asp Glu
                85                  90                  95

Ile Leu Asp Gly Asp Glu Ala Ala Glu Glu Val Lys Ala Gly Lys Gly
            100                 105                 110

Glu Glu Glu Glu Gly Glu Gly Glu Asn Lys Gly Phe Val Leu Ser Asp
        115                 120                 125

Asp Asp Glu Asp Asp Ala Pro Ala Gln Gln Val Ala Val Ala Gly Ala
    130                 135                 140

Thr Ala Asp Pro Val Lys Asp Tyr Leu Lys Gln Ile Gly Lys Val Pro
145                 150                 155                 160

Leu Leu Asn Ala Glu Gln Glu Val Glu Leu Ala Lys Arg Ile Glu Ala
                165                 170                 175

Gly Leu Phe Ala Glu Asp Lys Leu Ala Asn Ala Asp Lys Leu Ala Pro
            180                 185                 190

Lys Leu Lys Arg Glu Leu Glu Ile Ile Ala Glu Asp Gly Arg Arg Ala
        195                 200                 205

Lys Asn His Leu Leu Glu Ala Asn Leu Arg Leu Val Val Ser Leu Ala
    210                 215                 220

Lys Arg Tyr Thr Gly Arg Gly Met Leu Phe Leu Asp Leu Ile Gln Glu
225                 230                 235                 240

Gly Asn Leu Gly Leu Ile Arg Ala Val Glu Lys Phe Asp Tyr Thr Lys
                245                 250                 255

Gly Tyr Lys Phe Ser Thr Tyr Ala Thr Trp Trp Ile Arg Gln Ala Ile
            260                 265                 270

Thr Arg Ala Met Ala Asp Gln Ala Arg Thr Ile Arg Ile Pro Val His
        275                 280                 285

Met Val Glu Val Ile Asn Lys Leu Ala Arg Val Gln Arg Gln Met Leu
    290                 295                 300

Gln Asp Leu Gly Arg Glu
305                 310
```

( 2 ) INFORMATION FOR SEQ ID NO:7:

( i ) SEQUENCE CHARACTERISTICS:
( A ) LENGTH: 375 amino acids
( B ) TYPE: amino acid
( C ) STRANDEDNESS: single
( D ) TOPOLOGY: linear ( x i ) SEQUENCE DESCRIPTION: SEQ ID NO:7:

```
Val Tyr Val Ala Ala Thr Xaa Ala Ser Thr Ala Thr Asp Glu Pro Val
1               5                   10                  15

Lys Arg Thr Ala Thr Lys Ser Pro Ala Ala Ser Ala Ser Gly Ala Lys
            20                  25                  30

Thr Gly Pro Lys Arg Thr Ala Ala Lys Ser Ala Ser Gly Ser Pro Pro
        35                  40                  45

Ala Lys Arg Ala Thr Lys Pro Ala Ala Arg Ser Val Lys Pro Ala Ser
    50                  55                  60

Ala Pro Gln Asp Thr Thr Thr Ser Thr Ile Pro Lys Arg Lys Thr Arg
65                  70                  75                  80

Ala Ala Ala Lys Ser Ala Ala Ala Lys Ala Pro Ser Ala Arg Gly His
                85                  90                  95

Ala Thr Lys Pro Arg Ala Pro Lys Asp Ala Gln His Glu Ala Ala Thr
            100                 105                 110

Asp Pro Glu Asp Ala Leu Asp Ser Val Glu Glu Leu Asp Ala Glu Pro
        115                 120                 125
```

| Asp | Leu | Asp | Phe | Glu | Pro | Gly | Glu | Asp | Leu | Asp | Leu | Asp | Ala | Ala | Asp |
|-----|-----|-----|-----|-----|-----|-----|-----|-----|-----|-----|-----|-----|-----|-----|-----|
| | 130 | | | | 135 | | | | | 140 | | | | | |
| Leu | Asn | Leu | Asp | Asp | Leu | Glu | Asp | Asp | Val | Ala | Pro | Asp | Ala | Asp | Asp |
| 145 | | | | | 150 | | | | | 155 | | | | | 160 |
| Asp | Leu | Asp | Ser | Gly | Asp | Asp | Glu | Asp | His | Glu | Asp | Leu | Glu | Ala | Glu |
| | | | | 165 | | | | | 170 | | | | | 175 | |
| Ala | Ala | Val | Ala | Pro | Gly | Gln | Thr | Ala | Asp | Asp | Asp | Glu | Glu | Ile | Ala |
| | | | 180 | | | | | 185 | | | | | 190 | | |
| Glu | Pro | Thr | Glu | Lys | Asp | Lys | Ala | Ser | Gly | Asp | Phe | Val | Trp | Asp | Glu |
| | | 195 | | | | | 200 | | | | | 205 | | | |
| Asp | Glu | Ser | Glu | Ala | Leu | Arg | Gln | Ala | Arg | Lys | Asp | Ala | Glu | Leu | Thr |
| | 210 | | | | | 215 | | | | | 220 | | | | |
| Ala | Ser | Ala | Asp | Ser | Val | Arg | Ala | Tyr | Leu | Lys | Gln | Ile | Gly | Lys | Val |
| 225 | | | | | 230 | | | | | 235 | | | | | 240 |
| Ala | Leu | Leu | Asn | Ala | Glu | Glu | Glu | Val | Glu | Leu | Ala | Lys | Arg | Ile | Glu |
| | | | | 245 | | | | | 250 | | | | | 255 | |
| Ala | Gly | Leu | Tyr | Ala | Thr | Gln | Leu | Met | Thr | Glu | Leu | Ser | Glu | Arg | Gly |
| | | | 260 | | | | | 265 | | | | | 270 | | |
| Glu | Lys | Leu | Pro | Ala | Ala | Gln | Arg | Arg | Asp | Met | Met | Trp | Ile | Cys | Arg |
| | | 275 | | | | | 280 | | | | | 285 | | | |
| Asp | Gly | Asp | Arg | Ala | Lys | Asn | His | Leu | Leu | Glu | Ala | Asn | Leu | Arg | Leu |
| | 290 | | | | | 295 | | | | | 300 | | | | |
| Val | Val | Ser | Leu | Ala | Lys | Arg | Tyr | Thr | Gly | Arg | Gly | Met | Ala | Phe | Leu |
| 305 | | | | | 310 | | | | | 315 | | | | | 320 |
| Asp | Leu | Ile | Gln | Glu | Gly | Asn | Leu | Gly | Leu | Ile | Arg | Ala | Val | Glu | Lys |
| | | | | 325 | | | | | 330 | | | | | 335 | |
| Phe | Asp | Tyr | Thr | Lys | Gly | Tyr | Lys | Phe | Ser | Thr | Tyr | Ala | Thr | Trp | Trp |
| | | | 340 | | | | | 345 | | | | | 350 | | |
| Ile | Arg | Gln | Ala | Ile | Thr | Arg | Ala | Met | Ala | Asp | Gln | Ala | Arg | Thr | Ile |
| | | 355 | | | | | 360 | | | | | 365 | | | |
| Arg | Ile | Pro | Val | His | Met | Val | | | | | | | | | |
| | 370 | | | | | 375 | | | | | | | | | |

( 2 ) INFORMATION FOR SEQ ID NO:8:

( i ) SEQUENCE CHARACTERISTICS:
      ( A ) LENGTH: 530 amino acids
      ( B ) TYPE: amino acid
      ( C ) STRANDEDNESS: single
      ( D ) TOPOLOGY: linear ( x i ) SEQUENCE DESCRIPTION: SEQ ID NO:8:

| Val | Tyr | Val | Ala | Ala | Thr | Lys | Ala | Ser | Thr | Ala | Thr | Asp | Glu | Pro | Val |
|-----|-----|-----|-----|-----|-----|-----|-----|-----|-----|-----|-----|-----|-----|-----|-----|
| 1 | | | | 5 | | | | | 10 | | | | | 15 | |
| Lys | Arg | Thr | Ala | Thr | Lys | Ser | Pro | Ala | Ala | Ser | Ala | Ser | Gly | Ala | Lys |
| | | | 20 | | | | | 25 | | | | | 30 | | |
| Thr | Gly | Ala | Lys | Arg | Thr | Ala | Ala | Lys | Ser | Ala | Ser | Gly | Ser | Pro | Pro |
| | | | 35 | | | | | 40 | | | | | 45 | | |
| Ala | Lys | Arg | Ala | Thr | Lys | Pro | Ala | Ala | Arg | Ser | Val | Lys | Pro | Ala | Ser |
| | 50 | | | | | 55 | | | | | 60 | | | | |
| Ala | Pro | Gln | Asp | Thr | Thr | Thr | Ser | Thr | Ile | Pro | Lys | Arg | Lys | Thr | Arg |
| 65 | | | | | 70 | | | | | 75 | | | | | 80 |
| Ala | Ala | Ala | Lys | Ser | Ala | Ala | Ala | Lys | Ala | Pro | Ser | Ala | Arg | Gly | His |
| | | | | 85 | | | | | 90 | | | | | 95 | |
| Ala | Thr | Lys | Pro | Arg | Ala | Pro | Lys | Asp | Ala | Gln | His | Glu | Ala | Ala | Thr |
| | | | 100 | | | | | 105 | | | | | 110 | | |

-continued

| | | | | | | | | | | | | | |
|---|---|---|---|---|---|---|---|---|---|---|---|---|---|
|Asp|Pro|Glu|Asp|Ala|Leu|Asp|Ser|Val|Glu|Glu|Leu|Asp|Ala|Glu|Pro|
| | |115| | | | |120| | | |125| | | |
|Asp|Leu|Asp|Val|Glu|Pro|Gly|Glu|Asp|Leu|Asp|Leu|Asp|Ala|Ala|Asp|
| |130| | | | |135| | | |140| | | | | |
|Leu|Asn|Leu|Asp|Asp|Leu|Glu|Asp|Asp|Val|Ala|Pro|Asp|Ala|Asp|Asp|
|145| | | | |150| | | |155| | | | | |160|
|Asp|Leu|Asp|Ser|Gly|Asp|Asp|Glu|Asp|His|Glu|Asp|Leu|Glu|Ala|Glu|
| | | | |165| | | |170| | | | |175| | |
|Ala|Ala|Val|Ala|Pro|Gly|Gln|Thr|Ala|Asp|Asp|Glu|Glu|Ile|Ala|
| | | |180| | | |185| | | |190| | | |
|Glu|Pro|Thr|Glu|Lys|Asp|Lys|Ala|Ser|Gly|Asp|Phe|Val|Trp|Asp|Glu|
| | |195| | | |200| | | |205| | | | |
|Asp|Glu|Ser|Glu|Ala|Leu|Arg|Gln|Ala|Arg|Lys|Asp|Ala|Glu|Leu|Thr|
| |210| | | | |215| | | |220| | | | |
|Ala|Ser|Ala|Asp|Ser|Val|Arg|Ala|Tyr|Leu|Lys|Gln|Ile|Gly|Lys|Val|
|225| | | | |230| | | |235| | | | |240|
|Ala|Leu|Leu|Asn|Ala|Glu|Glu|Val|Glu|Leu|Ala|Lys|Arg|Ile|Glu|
| | | | |245| | | |250| | | |255| |
|Ala|Gly|Leu|Tyr|Ala|Thr|Gln|Leu|Met|Thr|Glu|Leu|Ser|Glu|Arg|Gly|
| | | |260| | | |265| | | |270| | | |
|Glu|Lys|Leu|Pro|Ala|Ala|Gln|Arg|Arg|Asp|Met|Met|Trp|Ile|Cys|Arg|
| | |275| | | |280| | | |285| | | | |
|Asp|Gly|Asp|Arg|Ala|Lys|Asn|His|Leu|Leu|Glu|Ala|Asn|Leu|Arg|Leu|
| |290| | | | |295| | | |300| | | | |
|Val|Val|Ser|Leu|Ala|Lys|Arg|Tyr|Thr|Gly|Arg|Gly|Met|Ala|Phe|Leu|
|305| | | | |310| | | |315| | | | |320|
|Asp|Leu|Ile|Gln|Glu|Gly|Asn|Leu|Gly|Leu|Ile|Arg|Ala|Val|Glu|Lys|
| | | |325| | | |330| | | |335| |
|Phe|Asp|Tyr|Thr|Lys|Gly|Tyr|Lys|Phe|Ser|Thr|Tyr|Ala|Thr|Trp|Trp|
| | |340| | | |345| | | |350| | |
|Ile|Arg|Gln|Ala|Ile|Thr|Arg|Ala|Met|Ala|Asp|Gln|Ala|Arg|Thr|Ile|
| |355| | | | |360| | | |365| | | | |
|Arg|Ile|Pro|Val|His|Met|Val|Glu|Val|Ile|Asn|Lys|Leu|Gly|Arg|Ile|
|370| | | | |375| | | |380| | | | |
|Gln|Arg|Glu|Leu|Leu|Gln|Asp|Leu|Gly|Arg|Glu|Pro|Thr|Pro|Glu|Glu|
|385| | | | |390| | | |395| | | |400|
|Leu|Ala|Lys|Glu|Met|Asp|Ile|Thr|Pro|Glu|Lys|Val|Leu|Glu|Ile|Gln|
| | | |405| | | |410| | | |415| |
|Gln|Tyr|Ala|Arg|Glu|Pro|Ile|Ser|Leu|Asp|Gln|Thr|Ile|Gly|Asp|Glu|
| | |420| | | |425| | | |430| | | |
|Gly|Asp|Ser|Gln|Leu|Gly|Asp|Phe|Ile|Glu|Asp|Ser|Glu|Ala|Val|Val|
| |435| | | | |440| | | |445| | | |
|Ala|Val|Asp|Ala|Val|Ser|Phe|Thr|Leu|Leu|Gln|Asp|Gln|Leu|Gln|Ser|
|450| | | | |455| | | |460| | | | |
|Val|Leu|Asp|Thr|Leu|Ser|Glu|Arg|Glu|Ala|Gly|Val|Val|Arg|Leu|Arg|
|465| | | |470| | | |475| | | |480|
|Phe|Gly|Leu|Thr|Asp|Gly|Gln|Pro|Arg|Thr|Leu|Asp|Glu|Ile|Gly|Gln|
| | | |485| | | |490| | | |495| |
|Val|Tyr|Gly|Val|Thr|Arg|Glu|Arg|Ile|Arg|Gln|Ile|Glu|Ser|Lys|Thr|
| | |500| | | |505| | | |510| | |
|Met|Ser|Lys|Leu|His|His|Pro|Ser|Arg|Ser|Gln|Val|Leu|Arg|Asp|Tyr|
| | |515| | | |520| | | |525| | |
|Leu|Asp|

530

(2) INFORMATION FOR SEQ ID NO:9:

(i) SEQUENCE CHARACTERISTICS:
      (A) LENGTH: 530 amino acids
      (B) TYPE: amino acid
      (C) STRANDEDNESS: single
      (D) TOPOLOGY: linear (xi) SEQUENCE DESCRIPTION: SEQ ID NO:9:

```
Val  Tyr  Val  Ala  Ala  Thr  Lys  Ala  Ser  Thr  Ala  Thr  Asp  Glu  Pro  Val
 1                  5                        10                       15
Lys  Arg  Thr  Ala  Thr  Lys  Ser  Pro  Ala  Ala  Ser  Ala  Ser  Gly  Ala  Lys
               20                  25                       30
Thr  Gly  Pro  Lys  Arg  Thr  Ala  Ala  Lys  Ser  Ala  Ser  Gly  Ser  Pro  Pro
          35                       40                  45
Ala  Lys  Arg  Ala  Thr  Lys  Pro  Ala  Ala  Arg  Ser  Val  Lys  Pro  Ala  Ser
     50                       55                  60
Ala  Pro  Gln  Asp  Thr  Thr  Thr  Ser  Thr  Ile  Pro  Lys  Arg  Lys  Thr  Arg
 65                      70                  75                           80
Ala  Ala  Ala  Lys  Ser  Ala  Ala  Ala  Lys  Ala  Pro  Ser  Ala  Arg  Gly  His
               85                       90                            95
Ala  Thr  Lys  Pro  Arg  Ala  Pro  Lys  Asp  Ala  Gln  His  Glu  Ala  Ala  Thr
               100                      105                      110
Asp  Pro  Glu  Asp  Ala  Leu  Asp  Ser  Val  Glu  Glu  Leu  Asp  Ala  Glu  Pro
          115                      120                      125
Asp  Leu  Asp  Val  Glu  Pro  Gly  Glu  Asp  Leu  Asp  Leu  Asp  Ala  Ala  Asp
     130                      135                      140
Leu  Asn  Leu  Asp  Asp  Leu  Glu  Asp  Asp  Val  Ala  Pro  Asp  Ala  Asp  Asp
145                       150                      155                      160
Asp  Leu  Asp  Ser  Gly  Asp  Asp  Glu  Asp  His  Glu  Asp  Leu  Glu  Ala  Glu
               165                      170                      175
Ala  Ala  Val  Ala  Pro  Gly  Gln  Thr  Ala  Asp  Asp  Glu  Glu  Ile  Ala
               180                      185                      190
Glu  Pro  Thr  Glu  Lys  Asp  Lys  Ala  Ser  Gly  Asp  Phe  Val  Trp  Asp  Glu
          195                      200                      205
Asp  Glu  Ser  Glu  Ala  Leu  Arg  Gln  Ala  Arg  Lys  Asp  Ala  Glu  Leu  Thr
     210                      215                      220
Ala  Ser  Ala  Asp  Ser  Val  Arg  Ala  Tyr  Leu  Lys  Gln  Ile  Gly  Lys  Val
225                       230                      235                      240
Ala  Leu  Leu  Asn  Ala  Glu  Glu  Glu  Val  Glu  Leu  Ala  Lys  Arg  Ile  Glu
               245                      250                      255
Ala  Gly  Leu  Tyr  Ala  Thr  Gln  Leu  Met  Thr  Glu  Leu  Ser  Glu  Arg  Gly
               260                      265                      270
Glu  Lys  Leu  Pro  Ala  Ala  Gln  Arg  Arg  Asp  Met  Met  Trp  Ile  Cys  Arg
          275                      280                      285
Asp  Gly  Asp  Arg  Ala  Lys  Asn  His  Leu  Leu  Glu  Ala  Asn  Leu  Arg  Leu
     290                      295                      300
Val  Val  Ser  Leu  Ala  Lys  Arg  Tyr  Thr  Gly  Arg  Gly  Met  Ala  Phe  Leu
305                       310                      315                      320
Asp  Leu  Ile  Gln  Glu  Gly  Asn  Leu  Gly  Leu  Ile  Arg  Ala  Val  Glu  Lys
               325                      330                      335
Phe  Asp  Tyr  Thr  Lys  Gly  Tyr  Lys  Phe  Ser  Thr  Tyr  Ala  Thr  Trp  Trp
               340                      345                      350
Ile  Arg  Gln  Ala  Ile  Thr  Arg  Ala  Met  Ala  Asp  Gln  Ala  Arg  Thr  Ile
```

|   |   |   |   |   | 355 |   |   |   |   | 360 |   |   |   |   | 365 |   |   |
|---|---|---|---|---|---|---|---|---|---|---|---|---|---|---|---|---|---|

Arg Ile Pro Val His Met Val Glu Val Ile Asn Lys Leu Gly Arg Ile
                370                         375                 380

Gln Arg Glu Leu Leu Gln Asp Leu Gly Arg Glu Pro Thr Pro Glu Glu
385                         390                 395                         400

Leu Ala Lys Glu Met Asp Ile Thr Pro Glu Lys Val Leu Glu Ile Gln
                    405                 410                         415

Gln Tyr Ala Arg Glu Pro Ile Ser Leu Asp Gln Thr Ile Gly Asp Glu
                420                     425                     430

Gly Asp Ser Gln Leu Gly Asp Phe Ile Glu Asp Ser Glu Ala Val Val
                435                 440                 445

Ala Val Asp Ala Val Ser Phe Thr Leu Leu Gln Asp Gln Leu Gln Ser
        450                 455                         460

Val Leu Asp Thr Leu Ser Glu Arg Glu Ala Gly Val Val Arg Leu Arg
465                     470                     475                     480

Phe Gly Leu Thr Asp Gly Gln Pro Arg Thr Leu Asp Glu Ile Gly Gln
                    485                     490                     495

Val Tyr Gly Val Thr Arg Glu Arg Ile Arg Gln Ile Glu Ser Lys Thr
                500                     505                     510

Met Ser Lys Leu Arg His Pro Ser Arg Ser Gln Val Leu Arg Asp Tyr
        515                     520                     525

Leu Asp
530

( 2 ) INFORMATION FOR SEQ ID NO:10:

( i ) SEQUENCE CHARACTERISTICS:
( A ) LENGTH: 530 amino acids
( B ) TYPE: amino acid
( C ) STRANDEDNESS: single
( D ) TOPOLOGY: linear ( x i ) SEQUENCE DESCRIPTION: SEQ ID NO:10:

Val Tyr Val Ala Ala Thr Lys Ala Ser Thr Ala Thr Asp Glu Pro Val
1               5                   10                      15

Lys Arg Thr Ala Thr Lys Ser Pro Ala Ala Ser Ala Ser Gly Ala Lys
                20                  25                  30

Thr Gly Ala Lys Arg Thr Ala Ala Lys Ser Ala Ser Gly Ser Pro Pro
            35                  40                  45

Ala Lys Arg Ala Thr Lys Pro Ala Ala Arg Ser Val Lys Pro Ala Ser
        50                  55                  60

Ala Pro Gln Asp Thr Thr Thr Ser Thr Ile Pro Lys Arg Lys Thr Arg
65                  70                  75                      80

Ala Ala Ala Lys Ser Ala Ala Ala Lys Ala Pro Ser Ala Arg Gly His
                85                  90                  95

Ala Thr Lys Pro Arg Ala Pro Lys Asp Ala Gln His Glu Ala Ala Thr
            100                 105                 110

Asp Pro Glu Asp Ala Leu Asp Ser Val Glu Glu Leu Asp Ala Glu Pro
        115                 120                 125

Asp Leu Asp Val Glu Pro Gly Glu Asp Leu Asp Leu Asp Ala Ala Asp
    130                 135                 140

Leu Asn Leu Asp Asp Leu Glu Asp Val Ala Pro Asp Ala Asp Asp
145                 150                 155                 160

Asp Leu Asp Ser Gly Asp Asp Glu Asp His Glu Asp Leu Glu Ala Glu
                165                 170                 175

Ala Ala Val Ala Pro Gly Gln Thr Ala Asp Asp Asp Glu Glu Ile Ala

|  |  |  |  |  |  |  |  |  |  |  |  |  |  |  |
|---|---|---|---|---|---|---|---|---|---|---|---|---|---|---|
| | | | | | 180 | | | | 185 | | | | 190 | |
| Glu | Pro | Thr 195 | Glu | Lys | Asp | Lys | Ala 200 | Ser | Gly | Asp | Phe 205 | Val | Trp | Asp Glu |
| Asp | Glu 210 | Ser | Glu | Ala | Leu | Arg 215 | Gln | Ala | Arg | Lys 220 | Asp | Ala | Glu | Leu Thr |
| Ala 225 | Ser | Ala | Asp | Ser 230 | Val | Arg | Ala | Tyr | Leu 235 | Lys | Gln | Ile | Gly | Lys Val 240 |
| Ala | Leu | Leu | Asn 245 | Ala | Glu | Glu | Val | Glu 250 | Leu | Ala | Lys | Arg | Ile 255 | Glu |
| Ala | Gly | Leu | Tyr 260 | Ala | Thr | Gln | Leu | Met 265 | Thr | Glu | Leu | Ser | Glu 270 | Arg Gly |
| Glu | Lys | Leu 275 | Pro | Ala | Ala | Gln | Arg 280 | Arg | Asp | Met | Met 285 | Trp | Ile | Cys Arg |
| Asp | Gly 290 | Asp | Arg | Ala | Lys | Asn 295 | His | Leu | Leu | Glu 300 | Ala | Asn | Leu | Arg Leu |
| Val 305 | Val | Ser | Leu | Ala | Lys 310 | Arg | Tyr | Thr | Gly | Arg 315 | Gly | Met | Ala | Phe Leu 320 |
| Asp | Leu | Ile | Gln | Glu 325 | Gly | Asn | Leu | Gly | Leu 330 | Ile | Arg | Ala | Val | Glu Lys 335 |
| Phe | Asp | Tyr | Thr 340 | Lys | Gly | Tyr | Lys | Phe 345 | Ser | Thr | Tyr | Ala | Thr 350 | Trp Trp |
| Ile | Arg | Gln 355 | Ala | Ile | Thr | Arg | Ala 360 | Met | Ala | Asp | Gln | Ala 365 | Arg | Thr Ile |
| Arg | Ile 370 | Pro | Val | His | Met | Val 375 | Glu | Val | Ile | Asn 380 | Lys | Leu | Gly | Arg Ile |
| Gln 385 | Arg | Glu | Leu | Leu | Gln 390 | Asp | Leu | Gly | Arg | Glu 395 | Pro | Thr | Pro | Glu Glu 400 |
| Leu | Ala | Lys | Glu | Met 405 | Asp | Ile | Thr | Pro | Glu 410 | Lys | Val | Leu | Glu | Ile Gln 415 |
| Gln | Tyr | Ala | Arg 420 | Glu | Pro | Ile | Ser | Leu 425 | Asp | Gln | Thr | Ile | Gly 430 | Asp Glu |
| Gly | Asp | Ser 435 | Gln | Leu | Gly | Asp | Phe 440 | Ile | Glu | Asp | Ser | Glu 445 | Ala | Val Val |
| Ala | Val 450 | Asp | Ala | Val | Ser | Phe 455 | Thr | Leu | Leu | Gln 460 | Asp | Gln | Leu | Gln Ser |
| Val 465 | Leu | Asp | Thr | Leu | Ser 470 | Glu | Arg | Glu | Ala | Gly 475 | Val | Val | Arg | Leu Arg 480 |
| Phe | Gly | Leu | Thr | Asp 485 | Gly | Gln | Pro | Arg | Thr 490 | Leu | Asp | Glu | Ile | Gly Gln 495 |
| Val | Tyr | Gly | Val 500 | Thr | Arg | Glu | Arg | Ile 505 | Arg | Gln | Ile | Glu | Ser 510 | Lys Thr |
| Met | Ser | Lys 515 | Leu | Arg | His | Pro | Ser 520 | Arg | Ser | Gln | Val | Leu 525 | Arg | Asp Tyr |
| Leu | Asp 530 | | | | | | | | | | | | | |

( 2 ) INFORMATION FOR SEQ ID NO:11:

( i ) SEQUENCE CHARACTERISTICS:
        ( A ) LENGTH: 442 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

Met Val Ser Ala Ala Glu Pro Lys Arg Thr Arg Lys Ser Val Ala Ala

-continued

| | 1 | | | | 5 | | | | | 10 | | | | | 15 | |
|---|---|---|---|---|---|---|---|---|---|---|---|---|---|---|---|---|
| | Lys | Ser | Pro | Ala | Lys | Arg | Thr | Ala | Thr | Lys | Ala | Val | Ala | Ala | Asn | Pro |
| | | | | 20 | | | | 25 | | | | 30 | | | | |
| | Val | Thr | Ser | Arg | Lys | Ala | Thr | Ala | Pro | Ala | Ala | Pro | Ala | Ala | Pro | Ala |
| | | | 35 | | | | | 40 | | | | 45 | | | | |
| | Thr | Glu | Pro | Ala | Ala | Val | Glu | Glu | Ala | Pro | Ala | Lys | Lys | Ala | Ala |
| | 50 | | | | | 55 | | | | 60 | | | | | | |
| | Ala | Lys | Lys | Thr | Thr | Ala | Lys | Lys | Ala | Thr | Ala | Lys | Lys | Thr | Thr | Ala |
| | 65 | | | | 70 | | | | 75 | | | | | | | 80 |
| | Lys | Lys | Ala | Ala | Ala | Lys | Lys | Thr | Thr | Ala | Lys | Lys | Glu | Asp | Gly | Glu |
| | | | | | 85 | | | | 90 | | | | 95 | | | |
| | Leu | Leu | Glu | Asp | Glu | Ala | Thr | Glu | Glu | Pro | Lys | Ala | Ala | Thr | Glu | Glu |
| | | | | 100 | | | | 105 | | | | | 110 | | | |
| | Pro | Glu | Gly | Thr | Glu | Asn | Ala | Gly | Phe | Val | Leu | Ser | Asp | Glu | Asp | Glu |
| | | | 115 | | | | | 120 | | | | 125 | | | | |
| | Asp | Asp | Ala | Pro | Ala | Gln | Gln | Val | Ala | Ala | Ala | Gly | Ala | Thr | Ala | Asp |
| | 130 | | | | | 135 | | | | | 140 | | | | | |
| | Pro | Val | Lys | Asp | Tyr | Leu | Lys | Gln | Ile | Gly | Lys | Val | Pro | Leu | Leu | Asn |
| | 145 | | | | | 150 | | | | 155 | | | | | | 160 |
| | Ala | Glu | Gln | Glu | Val | Glu | Leu | Ala | Lys | Arg | Ile | Glu | Ala | Gly | Leu | Phe |
| | | | | | 165 | | | | 170 | | | | | | 175 | |
| | Ala | Glu | Asp | Lys | Leu | Ala | Asn | Ser | Asp | Lys | Leu | Ala | Pro | Lys | Leu | Lys |
| | | | | 180 | | | | | 185 | | | | 190 | | | |
| | Arg | Glu | Leu | Glu | Ile | Ile | Ala | Glu | Asp | Gly | Arg | Arg | Ala | Lys | Asn | His |
| | | | | 195 | | | | 200 | | | | 205 | | | | |
| | Leu | Leu | Glu | Ala | Asn | Leu | Arg | Leu | Val | Val | Ser | Leu | Ala | Lys | Arg | Tyr |
| | | 210 | | | | | 215 | | | | | 220 | | | | |
| | Thr | Gly | Arg | Gly | Met | Leu | Phe | Leu | Asp | Leu | Ile | Gln | Glu | Gly | Asn | Leu |
| | 225 | | | | 230 | | | | | 235 | | | | | | 240 |
| | Gly | Leu | Ile | Arg | Ala | Val | Glu | Lys | Phe | Asp | Tyr | Thr | Lys | Gly | Tyr | Lys |
| | | | | | 245 | | | | 250 | | | | | 255 | | |
| | Phe | Ser | Thr | Tyr | Ala | Thr | Trp | Trp | Ile | Arg | Gln | Ala | Ile | Thr | Arg | Ala |
| | | | | 260 | | | | | 265 | | | | 270 | | | |
| | Met | Ala | Asp | Gln | Ala | Arg | Thr | Ile | Arg | Ile | Pro | Val | His | Met | Val | Glu |
| | | | 275 | | | | | 280 | | | | | 285 | | | |
| | Val | Ile | Asn | Lys | Leu | Ala | Arg | Val | Gln | Arg | Gln | Met | Leu | Gln | Asp | Leu |
| | | 290 | | | | | 295 | | | | | 300 | | | | |
| | Gly | Arg | Glu | Pro | Thr | Pro | Glu | Glu | Leu | Ala | Lys | Glu | Leu | Asp | Met | Thr |
| | 305 | | | | 310 | | | | | 315 | | | | | | 320 |
| | Pro | Glu | Lys | Val | Ile | Glu | Val | Gln | Lys | Tyr | Gly | Arg | Glu | Pro | Ile | Ser |
| | | | | | 325 | | | | 330 | | | | | 335 | | |
| | Leu | His | Thr | Pro | Leu | Gly | Glu | Asp | Gly | Asp | Ser | Glu | Phe | Gly | Asp | Leu |
| | | | | 340 | | | | | 345 | | | | 350 | | | |
| | Ile | Glu | Asp | Ser | Glu | Ala | Val | Val | Pro | Ala | Asp | Ala | Val | Ser | Phe | Thr |
| | | | | 355 | | | | 360 | | | | | 365 | | | |
| | Leu | Leu | Gln | Glu | Gln | Leu | His | Ser | Val | Leu | Asp | Thr | Leu | Ser | Glu | Arg |
| | | 370 | | | | | 375 | | | | | 380 | | | | |
| | Glu | Ala | Gly | Val | Val | Ser | Met | Arg | Phe | Gly | Leu | Thr | Asp | Gly | Gln | Pro |
| | 385 | | | | | 390 | | | | | 395 | | | | | 400 |
| | Lys | Thr | Leu | Asp | Glu | Ile | Gly | Lys | Val | Tyr | Gly | Val | Thr | Arg | Glu | Arg |
| | | | | | 405 | | | | 410 | | | | | 415 | | |
| | Ile | Arg | Gln | Ile | Glu | Ser | Lys | Thr | Met | Ser | Lys | Leu | Arg | His | Pro | Ser |
| | | | | 420 | | | | | 425 | | | | 430 | | | |

```
        Arg  Ser  Gln  Val  Leu  Arg  Asp  Tyr  Leu  Asp
                  435                      440
```

( 2 ) INFORMATION FOR SEQ ID NO:12:

( i ) SEQUENCE CHARACTERISTICS:
        ( A ) LENGTH: 445 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
Met  Val  Ser  Ala  Ala  Glu  Ser  Pro  Lys  Arg  Ala  Arg  Lys  Ser  Val  Ala
 1              5                        10                       15

Ala  Lys  Ser  Pro  Val  Lys  Arg  Thr  Ala  Thr  Lys  Thr  Val  Ala  Ala  Lys
               20                        25                       30

Thr  Thr  Val  Thr  Arg  Thr  Val  Ala  Ala  Thr  Ala  Ala  Pro  Ala  Val  Glu
               35                        40                       45

Ser  Ala  Asp  Ala  Ala  Asp  Ala  Val  Ala  Ala  Ala  Pro  Ala  Lys  Lys
      50                        55                        60

Thr  Ala  Ala  Lys  Lys  Ala  Thr  Ala  Lys  Lys  Ala  Ala  Lys  Lys  Thr
 65                      70                        75                       80

Thr  Ala  Lys  Lys  Thr  Ala  Ala  Lys  Lys  Ser  Gly  Lys  Gln  Asp  Asp  Glu
                    85                        90                       95

Ile  Leu  Asp  Gly  Asp  Glu  Ala  Ala  Glu  Glu  Val  Lys  Ala  Gly  Lys  Gly
                   100                       105                      110

Glu  Glu  Glu  Glu  Gly  Glu  Gly  Glu  Asn  Lys  Gly  Phe  Val  Leu  Ser  Asp
               115                       120                      125

Asp  Asp  Glu  Asp  Asp  Ala  Pro  Ala  Gln  Gln  Val  Ala  Val  Ala  Gly  Ala
          130                       135                      140

Thr  Ala  Asp  Pro  Val  Lys  Asp  Tyr  Leu  Lys  Gln  Ile  Gly  Lys  Val  Pro
145                       150                       155                     160

Leu  Leu  Asn  Ala  Glu  Gln  Glu  Val  Glu  Leu  Ala  Lys  Arg  Ile  Glu  Ala
                    165                       170                      175

Gly  Leu  Phe  Ala  Glu  Asp  Lys  Leu  Ala  Asn  Ala  Asp  Lys  Leu  Ala  Pro
               180                       185                      190

Lys  Leu  Lys  Arg  Glu  Leu  Glu  Ile  Ile  Ala  Glu  Asp  Gly  Arg  Arg  Ala
          195                       200                      205

Lys  Asn  His  Leu  Leu  Glu  Ala  Asn  Leu  Arg  Leu  Val  Val  Ser  Leu  Ala
210                       215                       220

Lys  Arg  Tyr  Thr  Gly  Arg  Gly  Met  Leu  Phe  Leu  Asp  Leu  Ile  Gln  Glu
225                       230                       235                     240

Gly  Asn  Leu  Gly  Leu  Ile  Arg  Ala  Val  Glu  Lys  Phe  Asp  Tyr  Thr  Lys
                    245                       250                      255

Gly  Tyr  Lys  Phe  Ser  Thr  Tyr  Ala  Thr  Trp  Trp  Ile  Arg  Gln  Ala  Ile
               260                       265                      270

Thr  Arg  Ala  Met  Ala  Asp  Gln  Ala  Arg  Thr  Ile  Arg  Ile  Pro  Val  His
          275                       280                      285

Met  Val  Glu  Val  Ile  Asn  Lys  Leu  Ala  Arg  Val  Gln  Arg  Gln  Met  Leu
     290                       295                      300

Gln  Asp  Leu  Gly  Arg  Glu  Pro  Thr  Pro  Glu  Glu  Leu  Ala  Lys  Glu  Leu
305                       310                       315                     320

Asp  Met  Thr  Pro  Glu  Lys  Val  Ile  Glu  Val  Gln  Lys  Tyr  Gly  Arg  Glu
                    325                       330                      335

Pro  Ile  Ser  Leu  His  Thr  Pro  Leu  Gly  Glu  Asp  Gly  Asp  Ser  Glu  Phe
               340                       345                      350
```

|  |  |  |  |  |  |  |  |  |  |  |  |  |  |  |
|---|---|---|---|---|---|---|---|---|---|---|---|---|---|---|
| Gly | Asp | Leu<br>355 | Ile | Glu | Asp | Ser | Glu<br>360 | Ala | Val | Val | Pro | Ala<br>365 | Asp | Ala | Val |
| Ser | Phe<br>370 | Thr | Leu | Leu | Gln | Glu<br>375 | Gln | Leu | His | Ser | Val<br>380 | Leu | Asp | Thr | Leu |
| Ser<br>385 | Glu | Arg | Glu | Ala | Gly<br>390 | Val | Val | Ser | Met | Arg<br>395 | Phe | Gly | Leu | Thr | Asp<br>400 |
| Gly | Gln | Pro | Lys | Thr<br>405 | Leu | Asp | Glu | Ile | Gly<br>410 | Lys | Val | Tyr | Gly | Val<br>415 | Thr |
| Arg | Glu | Arg | Ile<br>420 | Arg | Gln | Ile | Glu | Ser<br>425 | Lys | Thr | Met | Ser | Lys<br>430 | Leu | Arg |
| His | Pro | Ser<br>435 | Arg | Ser | Gln | Val | Leu<br>440 | Arg | Asp | Tyr | Leu | Asp<br>445 | | | |

( 2 ) INFORMATION FOR SEQ ID NO:13:

( i ) SEQUENCE CHARACTERISTICS:
        ( A ) LENGTH: 2745 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 841..2424

( i x ) FEATURE:
        ( A ) NAME/KEY: misc_difference
        ( B ) LOCATION: replace(937, "")
        ( D ) OTHER INFORMATION: /note= "This position is G or C.
            If it is G the amino acid translation is Ala."

( i x ) FEATURE:
        ( A ) NAME/KEY: misc_difference
        ( B ) LOCATION: replace(2384, "")
        ( D ) OTHER INFORMATION: /note= "This position is A or G.
            If it is A the amino acid translation is His."

( i x ) FEATURE:
        ( A ) NAME/KEY: misc_difference
        ( B ) LOCATION: replace(2591, "")
        ( D ) OTHER INFORMATION: /note= "This position is C or T."

( x i ) SEQUENCE DESCRIPTION: SEQ ID NO:13:

```
GATCAAGCTG CTGACCCCGC AACCGGCCAC TCCGTTGGCG GTCGCCAAAA CCATCGCCGA        60

GGTCGTCAAC GGTTTCGGCT GGCGGGGTCC GCTGGGGGTG ACCTATCCCG GCGTCGTCAC       120

TCACGGCGTC GTCCGGACCG CGGCTAACGT GGACAAGTCC TGGATAGGGA CCAACGCACG       180

CGACACTATC GGCGCCGAGC TGGGCGGTCA GCAGGTCACC ATCCTCAACG ACGCTGATGC       240

CGCCGGGCTG GCCGAGACAC GCTACGGGGC CGGCAAGAAC AACCCTGGCT TAGTGGTACT       300

GCTCACATTC GGAACCGGGA TCGGGTCCGC GGTCATCCAC AACGGGACGT TGATACCCAA       360

CACCGAGTTC GGACATCTTG AGGTCGGCGG CAAGGAAGCG GAGGAAAGGG CCGCCTCCTC       420

GGTAAAGGAA AAGAACGACT GGACCTATCC AAAGTGGGCC AAGCAGGTGA CACGCGTGCT       480

CATCGCCATC GAGAACGCGA TCTGGCCTGA CCTGTTCATC GCCGGCGGCG GCATCAGCCG       540

CAAGGCCGAC AAATGGGTGC CGCTACTGGA AAACCGCACA CCAGTAGTGC CCGCGGCCCT       600

GCAGAACACC GCCGGAATTG TCGGTGCGGC CATGGCCTCT GTCGCAGATA CGACGCACTG       660

AAACTTGCCC GCTCGGGCTG TACTCGTGCG CAGTAAAGTT ACAATGGTCA GCGGCGGCCG       720

CCCGACCGAT AGCGCGCGAG TATTCACGCT GATATCAACG CCGACATTCG ACATAGCAGA       780

CACTTTCGGT TACGCACGCC CAGACCCAAC CGGAAGTGAG TAACGACCGA AGGGGTGTAT       840
```

| GTG | GCA | GCG | ACC | AAA | GCA | AGC | ACG | GCG | ACC | GAT | GAG | CCG | GTA | AAA | CGC | 888 |
|---|---|---|---|---|---|---|---|---|---|---|---|---|---|---|---|---|
| Val | Ala | Ala | Thr | Lys | Ala | Ser | Thr | Ala | Thr | Asp | Glu | Pro | Val | Lys | Arg | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 535 |     |     |     |     | 540 |     |     |     |     | 545 |     |      |
| ACC | GCC | ACC | AAG | TCG | CCC | GCG | GCT | TCC | GCG | TCC | GGG | GCC | AAG | ACC | GGC | 936  |
| Thr | Ala | Thr | Lys | Ser | Pro | Ala | Ala | Ser | Ala | Ser | Gly | Ala | Lys | Thr | Gly |      |
|     |     |     | 550 |     |     |     |     | 555 |     |     |     |     | 560 |     |     |      |
| CCC | AAG | CGA | ACA | GCG | GCG | AAG | TCC | GCT | AGT | GGC | TCC | CCA | CCC | GCG | AAG | 984  |
| Pro | Lys | Arg | Thr | Ala | Ala | Lys | Ser | Ala | Ser | Gly | Ser | Pro | Pro | Ala | Lys |      |
|     |     | 565 |     |     |     | 570 |     |     |     |     | 575 |     |     |     |     |      |
| CGG | GCT | ACC | AAG | CCC | GCG | GCC | CGG | TCC | GTC | AAG | CCC | GCC | TCG | GCA | CCC | 1032 |
| Arg | Ala | Thr | Lys | Pro | Ala | Ala | Arg | Ser | Val | Lys | Pro | Ala | Ser | Ala | Pro |      |
|     | 580 |     |     |     |     | 585 |     |     |     |     | 590 |     |     |     |     |      |
| CAG | GAC | ACT | ACG | ACC | AGC | ACC | ATC | CCG | AAA | AGG | AAG | ACC | CGC | GCC | GCG | 1080 |
| Gln | Asp | Thr | Thr | Thr | Ser | Thr | Ile | Pro | Lys | Arg | Lys | Thr | Arg | Ala | Ala |      |
| 595 |     |     |     |     | 600 |     |     |     |     | 605 |     |     |     |     | 610 |      |
| GCC | AAA | TCC | GCC | GCC | GCG | AAG | GCA | CCG | TCG | GCC | CGC | GGC | CAC | GCG | ACC | 1128 |
| Ala | Lys | Ser | Ala | Ala | Ala | Lys | Ala | Pro | Ser | Ala | Arg | Gly | His | Ala | Thr |      |
|     |     |     |     | 615 |     |     |     |     | 620 |     |     |     |     | 625 |     |      |
| AAG | CCA | CGG | GCG | CCC | AAG | GAT | GCC | CAG | CAC | GAA | GCC | GCA | ACG | GAT | CCC | 1176 |
| Lys | Pro | Arg | Ala | Pro | Lys | Asp | Ala | Gln | His | Glu | Ala | Ala | Thr | Asp | Pro |      |
|     |     |     | 630 |     |     |     |     | 635 |     |     |     |     | 640 |     |     |      |
| GAG | GAC | GCC | CTG | GAC | TCC | GTC | GAG | GAG | CTC | GAC | GCT | GAA | CCA | GAC | CTC | 1224 |
| Glu | Asp | Ala | Leu | Asp | Ser | Val | Glu | Glu | Leu | Asp | Ala | Glu | Pro | Asp | Leu |      |
|     |     | 645 |     |     |     |     | 650 |     |     |     |     | 655 |     |     |     |      |
| GAC | GTC | GAG | CCC | GGC | GAG | GAC | CTC | GAC | CTT | GAC | GCC | GCC | GAC | CTC | AAC | 1272 |
| Asp | Val | Glu | Pro | Gly | Glu | Asp | Leu | Asp | Leu | Asp | Ala | Ala | Asp | Leu | Asn |      |
|     | 660 |     |     |     |     | 665 |     |     |     |     | 670 |     |     |     |     |      |
| CTC | GAT | GAC | CTC | GAG | GAC | GAC | GTG | GCG | CCG | GAC | GCC | GAC | GAC | GAC | CTC | 1320 |
| Leu | Asp | Asp | Leu | Glu | Asp | Asp | Val | Ala | Pro | Asp | Ala | Asp | Asp | Asp | Leu |      |
| 675 |     |     |     |     | 680 |     |     |     |     | 685 |     |     |     |     | 690 |      |
| GAC | TCG | GGC | GAC | GAC | GAA | GAC | CAC | GAA | GAC | CTC | GAA | GCT | GAG | GCG | GCC | 1368 |
| Asp | Ser | Gly | Asp | Asp | Glu | Asp | His | Glu | Asp | Leu | Glu | Ala | Glu | Ala | Ala |      |
|     |     |     |     | 695 |     |     |     |     | 700 |     |     |     |     | 705 |     |      |
| GTC | GCG | CCC | GGC | CAG | ACC | GCC | GAT | GAC | GAC | GAG | GAG | ATC | GCT | GAA | CCC | 1416 |
| Val | Ala | Pro | Gly | Gln | Thr | Ala | Asp | Asp | Asp | Glu | Glu | Ile | Ala | Glu | Pro |      |
|     |     |     | 710 |     |     |     |     | 715 |     |     |     |     | 720 |     |     |      |
| ACC | GAA | AAG | GAC | AAG | GCC | TCC | GGT | GAT | TTC | GTC | TGG | GAT | GAA | GAC | GAG | 1464 |
| Thr | Glu | Lys | Asp | Lys | Ala | Ser | Gly | Asp | Phe | Val | Trp | Asp | Glu | Asp | Glu |      |
|     |     | 725 |     |     |     |     | 730 |     |     |     |     | 735 |     |     |     |      |
| TCG | GAG | GCC | CTG | CGT | CAA | GCA | CGC | AAG | GAC | GCC | GAA | CTC | ACC | GCA | TCC | 1512 |
| Ser | Glu | Ala | Leu | Arg | Gln | Ala | Arg | Lys | Asp | Ala | Glu | Leu | Thr | Ala | Ser |      |
|     | 740 |     |     |     |     | 745 |     |     |     |     | 750 |     |     |     |     |      |
| GCC | GAC | TCG | GTT | CGC | GCC | TAC | CTC | AAA | CAG | ATC | GGC | AAG | GTA | GCG | CTG | 1560 |
| Ala | Asp | Ser | Val | Arg | Ala | Tyr | Leu | Lys | Gln | Ile | Gly | Lys | Val | Ala | Leu |      |
| 755 |     |     |     |     | 760 |     |     |     |     | 765 |     |     |     |     | 770 |      |
| CTC | AAC | GCC | GAG | GAA | GAG | GTC | GAG | CTA | GCC | AAG | CGG | ATC | GAG | GCT | GGC | 1608 |
| Leu | Asn | Ala | Glu | Glu | Glu | Val | Glu | Leu | Ala | Lys | Arg | Ile | Glu | Ala | Gly |      |
|     |     |     |     | 775 |     |     |     |     | 780 |     |     |     |     | 785 |     |      |
| CTG | TAC | GCC | ACG | CAG | CTG | ATG | ACC | GAG | CTT | AGC | GAG | CGC | GGC | GAA | AAG | 1656 |
| Leu | Tyr | Ala | Thr | Gln | Leu | Met | Thr | Glu | Leu | Ser | Glu | Arg | Gly | Glu | Lys |      |
|     |     |     | 790 |     |     |     |     | 795 |     |     |     |     | 800 |     |     |      |
| CTG | CCT | GCC | GCC | CAG | CGC | CGC | GAC | ATG | ATG | TGG | ATC | TGC | CGC | GAC | GGC | 1704 |
| Leu | Pro | Ala | Ala | Gln | Arg | Arg | Asp | Met | Met | Trp | Ile | Cys | Arg | Asp | Gly |      |
|     |     | 805 |     |     |     |     | 810 |     |     |     |     | 815 |     |     |     |      |
| GAT | CGC | GCG | AAA | AAC | CAT | CTG | CTG | GAA | GCC | AAC | CTG | CGC | CTG | GTG | GTT | 1752 |
| Asp | Arg | Ala | Lys | Asn | His | Leu | Leu | Glu | Ala | Asn | Leu | Arg | Leu | Val | Val |      |
|     | 820 |     |     |     |     | 825 |     |     |     |     | 830 |     |     |     |     |      |
| TCG | CTA | GCC | AAG | CGC | TAC | ACC | GGC | CGG | GGC | ATG | GCG | TTT | CTC | GAC | CTG | 1800 |
| Ser | Leu | Ala | Lys | Arg | Tyr | Thr | Gly | Arg | Gly | Met | Ala | Phe | Leu | Asp | Leu |      |
| 835 |     |     |     |     | 840 |     |     |     |     | 845 |     |     |     |     | 850 |      |
| ATC | CAG | GAA | GGC | AAC | CTG | GGG | CTG | ATC | CGC | GCG | GTG | GAG | AAG | TTC | GAC | 1848 |
| Ile | Gln | Glu | Gly | Asn | Leu | Gly | Leu | Ile | Arg | Ala | Val | Glu | Lys | Phe | Asp |      |

| | | | | | | | | | | | | | | | | |
|---|---|---|---|---|---|---|---|---|---|---|---|---|---|---|---|---|
| | | | | 855 | | | | | 860 | | | | | 865 | | |
| TAC | ACC | AAG | GGG | TAC | AAG | TTC | TCC | ACC | TAC | GCT | ACG | TGG | TGG | ATT | CGC | 1896 |
| Tyr | Thr | Lys | Gly 870 | Tyr | Lys | Phe | Ser | Thr 875 | Tyr | Ala | Thr | Trp | Trp 880 | Ile | Arg | |
| CAG | GCC | ATC | ACC | CGC | GCC | ATG | GCC | GAC | CAG | GCC | CGC | ACC | ATC | CGC | ATC | 1944 |
| Gln | Ala | Ile 885 | Thr | Arg | Ala | Met | Ala 890 | Asp | Gln | Ala | Arg | Thr 895 | Ile | Arg | Ile | |
| CCG | GTG | CAC | ATG | GTC | GAG | GTG | ATC | AAC | AAG | CTG | GGC | CGC | ATT | CAA | CGC | 1992 |
| Pro | Val 900 | His | Met | Val | Glu | Val 905 | Ile | Asn | Lys | Leu | Gly 910 | Arg | Ile | Gln | Arg | |
| GAG | CTG | CTG | CAG | GAC | CTG | GGC | CGC | GAG | CCC | ACG | CCC | GAG | GAG | CTG | GCC | 2040 |
| Glu 915 | Leu | Leu | Gln | Asp | Leu 920 | Gly | Arg | Glu | Pro | Thr 925 | Pro | Glu | Glu | Leu | Ala 930 | |
| AAA | GAG | ATG | GAC | ATC | ACC | CCG | GAG | AAG | GTG | CTG | GAA | ATC | CAG | CAA | TAC | 2088 |
| Lys | Glu | Met | Asp | Ile 935 | Thr | Pro | Glu | Lys | Val 940 | Leu | Glu | Ile | Gln | Gln 945 | Tyr | |
| GCC | CGC | GAG | CCG | ATC | TCG | TTG | GAC | CAG | ACC | ATC | GGC | GAC | GAG | GGC | GAC | 2136 |
| Ala | Arg | Glu | Pro 950 | Ile | Ser | Leu | Asp | Gln | Thr 955 | Ile | Gly | Asp | Glu | Gly 960 | Asp | |
| AGC | CAG | CTT | GGC | GAT | TTC | ATC | GAA | GAC | AGC | GAG | GCG | GTG | GTG | GCC | GTC | 2184 |
| Ser | Gln | Leu 965 | Gly | Asp | Phe | Ile | Glu 970 | Asp | Ser | Glu | Ala | Val 975 | Val | Ala | Val | |
| GAC | GCG | GTG | TCC | TTC | ACT | TTG | CTG | CAG | GAT | CAA | CTG | CAG | TCG | GTG | CTG | 2232 |
| Asp | Ala 980 | Val | Ser | Phe | Thr | Leu 985 | Leu | Gln | Asp | Gln | Leu 990 | Gln | Ser | Val | Leu | |
| GAC | ACG | CTC | TCC | GAG | CGT | GAG | GCG | GGC | GTG | GTG | CGG | CTA | CGC | TTC | GGC | 2280 |
| Asp | Thr 995 | Leu | Ser | Glu | Arg 1000 | Glu | Ala | Gly | Val | Val 1005 | Arg | Leu | Arg | Phe | Gly 1010 | |
| CTT | ACC | GAC | GGC | CAG | CCG | CGC | ACC | CTT | GAC | GAG | ATC | GGC | CAG | GTC | TAC | 2328 |
| Leu | Thr | Asp | Gly 1015 | Gln | Pro | Arg | Thr | Leu 1020 | Asp | Glu | Ile | Gly | Gln 1025 | Val | Tyr | |
| GGC | GTG | ACC | CGG | GAA | CGC | ATC | CGC | CAG | ATC | GAA | TCC | AAG | ACT | ATG | TCG | 2376 |
| Gly | Val | Thr | Arg 1030 | Glu | Arg | Ile | Arg 1035 | Gln | Ile | Glu | Ser | Lys 1040 | Thr | Met | Ser | |
| AAG | TTG | CGC | CAT | CCG | AGC | CGC | TCA | CAG | GTC | CTG | CGC | GAC | TAC | CTG | GAC | 2424 |
| Lys | Leu | Arg 1045 | His | Pro | Ser | Arg | Ser 1050 | Gln | Val | Leu | Arg | Asp 1055 | Tyr | Leu | Asp | |

| | | | | |
|---|---|---|---|---|
| TGAGAGCGCC | CGCCGAGGCG | ACCAACGTAG | CGGGCCCCCA | TGTCAGCTAG CCGCACCATG | 2484 |
| GTCTCGTCCG | GATCGGAGTT | CGAATCAGCC | GTCGGCTACT | CGCGCGCGGT ACGCATCGGG | 2544 |
| CCACTCGTGG | TGGTGGCCGG | AACGACCGGC | AGCGGCGATG | ATATCGTCGC TCAGACGCGA | 2604 |
| GACGCTCTGC | GCCGCATCGA | GATTGCGCTC | GGACAGGCCG | GCGCAACTCT GGCCGACGTG | 2664 |
| GTCCGTACCC | GCATCTATGT | GACCGATATT | TCCCGCTGGC | GCGAGGTCGG CGAAGTGCAT | 2724 |
| GCACAGGCTT | TCGGCAAGAT | C | | | 2745 |

( 2 ) INFORMATION FOR SEQ ID NO:14:

( i ) SEQUENCE CHARACTERISTICS:
        ( A ) LENGTH: 528 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | |
|---|---|---|---|---|---|---|---|---|---|---|---|---|---|---|
| Val | Ala | Ala | Thr | Lys | Ala | Ser | Thr | Ala | Thr | Asp | Glu | Pro | Val | Lys | Arg |
| 1 | | | | 5 | | | | | 10 | | | | | 15 | |
| Thr | Ala | Thr | Lys | Ser | Pro | Ala | Ala | Ser | Ala | Ser | Gly | Ala | Lys | Thr | Gly |
| | | | 20 | | | | | 25 | | | | | 30 | | |

```
Pro Lys Arg Thr Ala Ala Lys Ser Ala Ser Gly Ser Pro Pro Ala Lys
         35                  40                  45

Arg Ala Thr Lys Pro Ala Ala Arg Ser Val Lys Pro Ala Ser Ala Pro
     50                  55                  60

Gln Asp Thr Thr Thr Ser Thr Ile Pro Lys Arg Lys Thr Arg Ala Ala
 65                      70                  75                  80

Ala Lys Ser Ala Ala Ala Lys Ala Pro Ser Ala Arg Gly His Ala Thr
                     85                  90                      95

Lys Pro Arg Ala Pro Lys Asp Ala Gln His Glu Ala Ala Thr Asp Pro
             100                 105                 110

Glu Asp Ala Leu Asp Ser Val Glu Glu Leu Asp Ala Glu Pro Asp Leu
             115                 120                 125

Asp Val Glu Pro Gly Glu Asp Leu Asp Leu Asp Ala Ala Asp Leu Asn
 130                     135                 140

Leu Asp Asp Leu Glu Asp Asp Val Ala Pro Asp Ala Asp Asp Asp Leu
 145                     150                 155                 160

Asp Ser Gly Asp Asp Glu Asp His Glu Asp Leu Glu Ala Glu Ala Ala
                 165                 170                 175

Val Ala Pro Gly Gln Thr Ala Asp Asp Glu Glu Ile Ala Glu Pro
             180                 185                 190

Thr Glu Lys Asp Lys Ala Ser Gly Asp Phe Val Trp Asp Glu Asp Glu
         195                 200                 205

Ser Glu Ala Leu Arg Gln Ala Arg Lys Asp Ala Glu Leu Thr Ala Ser
 210                     215                 220

Ala Asp Ser Val Arg Ala Tyr Leu Lys Gln Ile Gly Lys Val Ala Leu
 225                     230                 235                 240

Leu Asn Ala Glu Glu Glu Val Glu Leu Ala Lys Arg Ile Glu Ala Gly
                 245                 250                 255

Leu Tyr Ala Thr Gln Leu Met Thr Glu Leu Ser Glu Arg Gly Glu Lys
             260                 265                 270

Leu Pro Ala Ala Gln Arg Arg Asp Met Met Trp Ile Cys Arg Asp Gly
         275                 280                 285

Asp Arg Ala Lys Asn His Leu Leu Glu Ala Asn Leu Arg Leu Val Val
 290                     295                 300

Ser Leu Ala Lys Arg Tyr Thr Gly Arg Gly Met Ala Phe Leu Asp Leu
 305                     310                 315                 320

Ile Gln Glu Gly Asn Leu Gly Leu Ile Arg Ala Val Glu Lys Phe Asp
                 325                 330                 335

Tyr Thr Lys Gly Tyr Lys Phe Ser Thr Tyr Ala Thr Trp Trp Ile Arg
             340                 345                 350

Gln Ala Ile Thr Arg Ala Met Ala Asp Gln Ala Arg Thr Ile Arg Ile
         355                 360                 365

Pro Val His Met Val Glu Val Ile Asn Lys Leu Gly Arg Ile Gln Arg
 370                     375                 380

Glu Leu Leu Gln Asp Leu Gly Arg Glu Pro Thr Pro Glu Glu Leu Ala
 385                     390                 395                 400

Lys Glu Met Asp Ile Thr Pro Glu Lys Val Leu Glu Ile Gln Gln Tyr
             405                 410                 415

Ala Arg Glu Pro Ile Ser Leu Asp Gln Thr Ile Gly Asp Glu Gly Asp
             420                 425                 430

Ser Gln Leu Gly Asp Phe Ile Glu Asp Ser Glu Ala Val Val Ala Val
         435                 440                 445

Asp Ala Val Ser Phe Thr Leu Leu Gln Asp Gln Leu Gln Ser Val Leu
 450                     455                 460
```

| | | | | | | | | | | | | | | | |
|---|---|---|---|---|---|---|---|---|---|---|---|---|---|---|---|
| Asp<br>465 | Thr | Leu | Ser | Glu | Arg<br>470 | Glu | Ala | Gly | Val | Val<br>475 | Arg | Leu | Arg | Phe | Gly<br>480 |
| Leu | Thr | Asp | Gly | Gln<br>485 | Pro | Arg | Thr | Leu | Asp<br>490 | Glu | Ile | Gly | Gln | Val<br>495 | Tyr |
| Gly | Val | Thr | Arg<br>500 | Glu | Arg | Ile | Arg | Gln<br>505 | Ile | Glu | Ser | Lys | Thr<br>510 | Met | Ser |
| Lys | Leu | Arg<br>515 | His | Pro | Ser | Arg | Ser<br>520 | Gln | Val | Leu | Arg | Asp<br>525 | Tyr | Leu | Asp |

We claim:

1. A method for identifying a DNA sequence or sequences associated with virulence determinants in *M. tuberculosis* and *M. bovis* and substantially similar DNA sequences in other tuberculosis complex strains and in strains of other slow-growing mycobacterial species comprising the steps of:

a) preparing a genomic DNA library of the slow-growing mycobacterial species;

b) constructing an integrating shuttle vector containing genomic inserts prepared in step a);

c) transforming via homologous recombination using the integrating shuttle vector of step b) a population of avirulent organisms;

d) isolating the recombinants;

e) inoculating a subject with an adequate inoculum of the recombinants in order to select virulent recombinants;

f) isolating the virulent recombinants; and g) identifying the DNA inserts which confer virulence.

2. A method according to claim 1 wherein the subject inoculated is a mouse.

3. A method according to claim 1 wherein the subject inoculated is a guinea pig.

* * * * *